US007138253B2

(12) United States Patent
Szostak et al.

(10) Patent No.: US 7,138,253 B2
(45) Date of Patent: Nov. 21, 2006

(54) STREPTAVIDIN-BINDING PEPTIDES AND USES THEREOF

(75) Inventors: Jack W. Szostak, Boston, MA (US); David S. Wilson, Hayward, CA (US); Anthony D. Keefe, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/975,582

(22) Filed: Oct. 28, 2004

(65) Prior Publication Data

US 2005/0191722 A1 Sep. 1, 2005

Related U.S. Application Data

(62) Division of application No. 10/004,381, filed on Oct. 31, 2001, now Pat. No. 6,841,359.

(60) Provisional application No. 60/244,541, filed on Oct. 31, 2000.

(51) Int. Cl.
*C12P 21/06* (2006.01)
(52) U.S. Cl. .................................................. 435/69.1
(58) Field of Classification Search ................ 530/350; 514/12; 435/69.1
See application file for complete search history.

(56) References Cited

U.S. PATENT DOCUMENTS

| 5,506,121 A | 4/1996 | Skerra et al. |
| 5,821,047 A | 10/1998 | Garrard et al. |
| 6,103,493 A | 8/2000 | Skerra et al. |
| 6,326,157 B1 | 12/2001 | Nolan et al. |

FOREIGN PATENT DOCUMENTS

WO     WO 98/31700     7/1998

OTHER PUBLICATIONS

Bayer et al., "Postsecretory Modifications Of Streptavidin," *Biochem. J.* 259(2):369-376 (1989).
Caparon et al., "Analysis of Novel Streptavidin-Binding Peptides, Identified Using a Phage Display Library, Shows That Amino Acids External to a Perfectly Conserved Consensus Sequence and to the Presented Peptides Contribute to Binding," *Molecular Diversity* 1(4):241-246 (1995).
Cho et al., "Constructing High Complexity Synthetic Libraries of Long ORFs Using *In Vitro* Selection," *J. Mol. Biol.* 297:309-319 (2000).
Clackson and Wells "*In Vitro* Selection From Protein and Peptide Libraries," *TIBTECH.* 12:173-184 (1994).
Devlin et al., "Random Peptide Libraries: A Source of Specific Protein Binding Molecules," *Science* 249(4967):404-406 (1990).
Giebel et al., "Screening of Cyclic Peptide Phage Libraries Identifies Ligands That Bind Streptavidin With High Affinities," *Biochemistry* 34(47):15430-15435 (1995).

Haeuptle et al., "Binding Sites for Lactogenic and Somatogenic Hormones From Rabbit Mammary Gland and Liver," *J. Biol. Chem.* 258(1):305-314 (1983).
Katz et al., "Topochemical Catalysis Achieved by Structure-Based Ligand Design," *J. Biol. Chem.* 270(52):31210-31218 (1995).
Katz and Cass, "In Crystals of Complexes of Streptavidin With Peptide Ligands Containing the HPQ Sequence the $pK_a$ of the Peptide Histidine is Less Than 3.0," *J. Biol. Chem.* 272(20):13220-13228 (1997).
Katz, B.A., "Structural and Mechanistic Determinants of Affinity and Specificity of Ligands Discovered or Engineered by Phage Display," *Annu. Rev. Biophys. Biomol. Struct.* 26:27-45 (1997).
Katz, B.A., "Streptavidin-Binding and -Dimerizing Ligands Discovered by Phage Display, Topochemistry, and Structure-Based Design," *Biomol. Eng.* 16(1-4):57-65 (1999).
Katz, B.A., "Binding to Protein Targets of Peptidic Leads Discovered by Phage Display: Crystal Structures of Streptavidin-Bound Linear and Cyclic Peptide Ligands Containing the HPQ Sequence," *Biochemistry* 34(47):15421-15429 (1995).
Kay et al., "An M13 Phage Library Displaying Random 38-Amino-Acid Peptides as a Source of Novel Sequences With Affinity to Selected Targets," *Gene* 128(1):59-65 (1993).
Keefe and Szostak, "ATP-Binding Proteins Selected From a Random-Sequence Polypeptide Library," *The Protein Society, Fourteenth Symposium, Program and Abstracts*, 9(Suppl. 1):19 & 84 (No. 184-T), San Diego, CA (2000).
Lam et al., "A New Type of Synthetic Peptide Library for Identifying Ligand-Binding Activity," *Nature* 354(6348):82-84 (1991).
Liu et al., "Optimized Synthesis of RNA-Protein Fusions for *In Vitro* Protein Selection," *Methods Enzymol.* 318:268-293 (2000).
McCafferty et al., "Phage Antibodies: Filamentous Phage Displaying Antibody Variable Domains," *Nature* 348(6301):552-554 (1990).
McLafferty et al., "M13 Bacteriophage Displaying Disulfide-Constrained Microproteins," *Gene* 128(1):29-36 (1993).
Ostergaard et al., "Novel Avidin and Streptavidin Binding Sequences Found in Synthetic Peptide Libraries," *FEBS Letters* 362(3):306-308 (1995).
Roberts and Szostak, "RNA-Peptide Fusions for the *In Vitro* Selection of Peptides and Proteins,"*Proc. Natl. Acad. Sci. USA* 94:12297-12302 (1997).
Roberts, R.W. "Totally *In Vitro* Protein Selection Using mRNA-Protein Fusions and Ribosome Display," *Curr. Opin. Chem. Biol.* 3:268-273 (1999).
Schmidt and Skerra, "The Random Peptide Library-Assisted Engineering of a C-Terminal Affinity Peptide, Useful for the Detection and Purification of a Functional Ig Fv Fragment," *Protein Eng* 6(1):109-122 (1993).

(Continued)

*Primary Examiner*—Karen Cochrane Carlson
*Assistant Examiner*—Agnes Rooke
(74) *Attorney, Agent, or Firm*—Clark & Elbing LLP

(57) ABSTRACT

The invention provides peptides with high affinity for streptavidin. These peptides may be expressed as part of fusion proteins to facilitate the detection, quantitation, and purification of proteins of interest.

25 Claims, 17 Drawing Sheets

OTHER PUBLICATIONS

Schmidt et al., "Molecular Interaction Between the Strep-Tag Affinity Peptide and its Cognate Target, Streptavidin," *J. Mol. Biol.* 255:753-766 (1996).

Scott and Smith, "Searching for Peptide Ligands With an Epitope Library," *Science* 249(4967):386-390 (1990).

Szostak, J.W., "Evolution of Novel Proteins From Random-Sequence Libraries" 2000 (Abstract).

Weber et al., "Crystal Structure and Ligand-Binding Studies of a Screened Peptide Complexed With Streptavidin," *Biochemistry* 31(39):9350-9354 (1992).

Wilson et al., "The Use of mRNA Display to Select High-Affinity Protein-Binding Peptides," *PNAS* 98(7):3750-3755 (2001).

Zang et al., "Tight-Binding Streptavidin Ligands From a Cyclic Peptide Library," *Bioorg. Med. Chem. Lett.* 8(17):2327-2332 (1998).

SEQUENCE LISTING

<160> NUMBER OF SEQ ID NOS: 41

<210> SEQ ID NO 1
<211> LENGTH: 101
<212> TYPE: PRT
<213> ORGANISM: Artificial Sequence
<220> FEATURE:
<223> OTHER INFORMATION: selected peptide

<400> SEQUENCE: 1

Met Asp Glu Lys Thr His Cys Thr Ile Ser Met Asn Gly Ala Val Pro
 1               5                  10                  15

Leu Val Pro His His His Pro Gln Gly Asp Pro Leu Arg Leu Leu His
            20                  25                  30

Arg Pro Gln Pro Ala Leu Leu Val Arg His Pro Gln Gly Asp Leu Val
        35                  40                  45

Ala Leu Val Glu His His Glu Gly Val Asp Arg Gly Leu Val Ala Leu
    50                  55                  60

Pro Glu Leu His Ala Glu Glu Leu Gly Glu Pro Val Gly Asp Leu Val
65                  70                  75                  80

Gln Gly Pro Val Glu Gln Val Gln Gly Val Val Asp Ala Leu Val Trp
                85                  90                  95

Arg Leu Pro Pro Ser
            100

<210> SEQ ID NO 2
<211> LENGTH: 101
<212> TYPE: PRT
<213> ORGANISM: Artificial Sequence
<220> FEATURE:
<223> OTHER INFORMATION: selected peptide

<400> SEQUENCE: 2

Met Asp Glu Lys Thr His Cys Phe His Pro Gly Asp His Leu Val Arg
 1               5                  10                  15

Leu Val Glu Glu Leu Gln Ala Leu Ala Glu Gly Leu Gln Arg Gln Gly
            20                  25                  30

Gly Arg Gln Pro His Arg Leu Pro Arg Arg Pro His His Leu Gln
        35                  40                  45

Leu Leu Leu Asp Glu Ala His Pro Gln Ala Gly Pro Leu Arg Glu Arg
    50                  55                  60

```
Ala His Gln Val Asp Gly Arg Leu Leu Leu Gln His His Pro Gln Gly
 65                  70                  75                  80

Asp Arg Leu Leu Gln Gln Pro Gln Asp His Pro Leu Glu Leu Val Trp
                 85                  90                  95

Arg Leu Pro Pro Ser
            100

<210> SEQ ID NO 3
<211> LENGTH: 101
<212> TYPE: PRT
<213> ORGANISM: Artificial Sequence
<220> FEATURE:
<223> OTHER INFORMATION: selected peptide

<400> SEQUENCE: 3

Met Thr Arg Arg Pro Thr Ala Ser Ser Ser Cys Val Arg His Leu
 1               5                  10                  15

Leu Leu Arg Gln Gly Glu His Gly His Gln Ala Leu Glu Asp Arg Asp
                 20                  25                  30

Lys Ala Arg His Val Arg Leu Val Glu Gly Asp Val Glu Val Leu Gly
             35                  40                  45

Gly Leu Asp Arg Leu Ala Arg Ala Arg His Glu Ala Leu His Pro Gln
         50                  55                  60

Ala Gly Leu Val His Leu Pro Leu His Gly Gly Asp Leu Gly Gly His
 65                  70                  75                  80

Leu Arg Leu Val Leu Glu Ala His Pro Gln Gly Asp Arg Leu Gly Leu
                 85                  90                  95

Ala Val His His His
            100

<210> SEQ ID NO 4
<211> LENGTH: 102
<212> TYPE: PRT
<213> ORGANISM: Artificial Sequence
<220> FEATURE:
<223> OTHER INFORMATION: selected peptide

<400> SEQUENCE: 4

Met Asp Glu Lys Thr His Trp Gly Ile Ser Thr Trp Arg Gly Glu Pro
 1               5                  10                  15

Leu Leu His His Pro Gln Ala Gly Arg Leu Pro Leu Asp Arg Arg Arg
                 20                  25                  30

Ala Arg His Arg Arg Ile Leu Gly Ala Glu Pro Gly Gly Val Asp His
             35                  40                  45

Gly Leu Arg Leu Glu Leu Leu Asp Asp His Arg Pro Leu Val Pro Asp
         50                  55                  60

His His Pro Gln Arg Gly Pro Leu Gln Arg Gly Asp Leu Pro Gln Val
 65                  70                  75                  80

Val Pro Leu Val Arg Leu Arg His Ala His Val Leu Gly Leu Gly Leu
                 85                  90                  95

Ala Ala Ala Thr Ile Thr
            100

<210> SEQ ID NO 5
<211> LENGTH: 102
<212> TYPE: PRT
<213> ORGANISM: Artificial Sequence
<220> FEATURE:
<223> OTHER INFORMATION: selected peptide
```

```
<400> SEQUENCE: 5

Met Asp Glu Lys Thr His Trp Val Asn Val Tyr His Pro Gln Gly Asp
 1               5                  10                  15

Leu Leu Val Arg Gly His Gly His Asp Val Glu Ala Leu His Asp Gln
            20                  25                  30

Gly Leu His Gln Leu Asp Leu Val Gly Pro Pro Glu Val Val
        35                  40                  45

Arg Ala Leu Arg Gly Glu Val Leu Gly Gly Leu Arg Arg Leu Val Pro
    50                  55                  60

Leu Asp His Pro Gln Gly Glu Ala Leu Asp Gln Ala Arg Gln Arg Pro
65                  70                  75                  80

Gln His Leu Leu Glu Leu His His Arg Ala Leu Pro Pro Ala Leu Val
                85                  90                  95

Trp Arg Leu Pro Pro Ser
            100

<210> SEQ ID NO 6
<211> LENGTH: 102
<212> TYPE: PRT
<213> ORGANISM: Artificial Sequence
<220> FEATURE:
<223> OTHER INFORMATION: selected peptide

<400> SEQUENCE: 6

Met Asp Glu Lys Thr His Trp Leu Asn Asn Phe Glu Glu Leu Leu Ala
 1               5                  10                  15

Arg Leu Asp Gly Leu Arg Glu Gly Glu Asp His Pro Leu Val Leu Arg
            20                  25                  30

His His Pro Gln Gly Asp Gly Leu Leu Asp Gln Pro Leu Gly Arg His
        35                  40                  45

Arg Ala Leu Asp Gly Glu Val Arg Gly Asp Arg Pro Leu Asp Gln
    50                  55                  60

Gly Gly Glu Glu Asp Leu Gly Ala Leu Val Asp Asp Gly Glu Val
65                  70                  75                  80

Leu Asp Gly Leu Val His Val Gly Val His Val His Asp Pro Leu Val
                85                  90                  95

Cys Gly Cys His His His
            100

<210> SEQ ID NO 7
<211> LENGTH: 101
<212> TYPE: PRT
<213> ORGANISM: Artificial Sequence
<220> FEATURE:
<223> OTHER INFORMATION: selected peptide

<400> SEQUENCE: 7

Met Asp Glu Lys Thr His Trp Phe Gly Thr Leu Asn Ser Phe Pro Thr
 1               5                  10                  15

His Trp Met Ser Ala Val Gly Asn Gly Lys Ile Asp Cys Ser Phe Asn
            20                  25                  30

Met Asn Leu Ser Leu Asn His Trp Leu Ser Ser Gly His Pro Asp Gly
        35                  40                  45

Ala Leu Asp Asp Gln Leu His Pro Gln Gly Asp Ala Leu Val Gly Arg
    50                  55                  60

Asp Asp Gly Val Val Gln Ala Leu Arg Leu Glu Gly Gln His Gln His
65                  70                  75                  80
```

```
Arg Arg Leu Ala Gln Arg Arg Ala Asp Arg His Arg Gln Leu Val Trp
            85                  90                  95

Arg Leu Pro Pro Ser
            100

<210> SEQ ID NO 8
<211> LENGTH: 102
<212> TYPE: PRT
<213> ORGANISM: Artificial Sequence
<220> FEATURE:
<223> OTHER INFORMATION: selected peptide

<400> SEQUENCE: 8

Met Asp Glu Lys Thr His Cys Thr Ile Glu Leu Asn Phe Ser Phe Thr
  1               5                  10                  15

His Trp Lys Leu His His Pro Gln Gly Asp Ala Leu Leu Asp Asp
             20                  25                  30

Gly Val Arg Pro His His Pro Leu Ala Asp Glu Gly Gly Gly Leu Asp
             35                  40                  45

Gln Gly Leu Gly His Arg Arg Gly Val Val Ala Glu Arg Leu Ala Arg
         50                  55                  60

Arg Asp Pro Glu Val Leu Glu Gly Leu Val Glu Arg His Arg Gly Leu
 65                  70                  75                  80

Val Pro Arg Leu Arg His Gly Gly Glu Arg His Ala Glu Pro Leu Val
                 85                  90                  95

Trp Arg Leu Pro Pro Ser
            100

<210> SEQ ID NO 9
<211> LENGTH: 102
<212> TYPE: PRT
<213> ORGANISM: Artificial Sequence
<220> FEATURE:
<223> OTHER INFORMATION: selected peptide

<400> SEQUENCE: 9

Met Asp Glu Lys Thr His Cys Asn Thr Gly Leu Tyr Asp Gly Ala Ala
  1               5                  10                  15

Asp Cys Phe Asn Glu Leu Asn Lys Asp Val Ala Pro Leu Val Glu Gly
             20                  25                  30

Arg His Asp Leu Val Glu Gly Leu Leu Glu Arg His Pro Gln Gly
             35                  40                  45

Asp Pro Leu Val Ala His Arg Gln Leu Val His Pro Leu Leu Gly
         50                  55                  60

Arg Gly Glu Arg His Arg Arg Ala Leu Val Pro Gln Gln Glu His Gln
 65                  70                  75                  80

Pro His Arg Leu Gln Pro Val Val Asp Leu Gly Arg Arg Leu Val
                 85                  90                  95

Trp Arg Leu Pro Pro Ser
            100

<210> SEQ ID NO 10
<211> LENGTH: 103
<212> TYPE: PRT
<213> ORGANISM: Artificial Sequence
<220> FEATURE:
<223> OTHER INFORMATION: selected peptide

<400> SEQUENCE: 10

Met Asp Glu Lys Thr His Trp His Glu Arg Ala Gln Glu Leu Val Gly
```

```
                1               5                  10                 15
Gly Leu Leu Leu His Asp His Pro Gln Arg Leu Leu Glu Pro Arg
                20                 25                 30

Gly Pro Arg Pro Leu Arg Gly Leu Val His Glu Arg Gly His Gln Pro
                35                 40                 45

Gln Pro Leu Ala Gly Arg Val Glu Glu Ala Asp Gly Gly Leu Leu Arg
        50                 55                 60

Asp Gly Gly Gly Glu Leu Glu Pro Leu Val Arg Glu Gly Glu Asp His
65                 70                 75                 80

Leu Glu Pro Leu Asp Asp Glu Leu Asp Ala Gly Pro Arg Gly Leu Val
                85                 90                 95

Trp Arg Leu Pro His His His
                100

<210> SEQ ID NO 11
<211> LENGTH: 102
<212> TYPE: PRT
<213> ORGANISM: Artificial Sequence
<220> FEATURE:
<223> OTHER INFORMATION: selected peptide

<400> SEQUENCE: 11

Met Asp Glu Lys Thr His Trp His Glu Arg Val His His Leu Ala Asp
1               5                  10                 15

Gly Leu Glu Gln His Pro Gln Gly Gln Arg Arg Pro Leu Val Glu Arg
                20                 25                 30

His Arg Gln Val Pro Arg Gly Leu Val Arg Glu Leu Gln His Glu Gly
                35                 40                 45

Leu Pro Leu Glu His Pro Ala Gly Val His Val Ile Arg Leu His Gln
        50                 55                 60

Gly Asp Arg Asp Val Asp Gly Leu Val Asp Gly His Gly Arg Asp
65                 70                 75                 80

Val Arg Gly Leu Glu Arg Glu Val Gly Asp Gly Pro His Arg Leu Val
                85                 90                 95

Trp Arg Leu Pro Pro Ser
                100

<210> SEQ ID NO 12
<211> LENGTH: 101
<212> TYPE: PRT
<213> ORGANISM: Artificial Sequence
<220> FEATURE:
<223> OTHER INFORMATION: selected peptide

<400> SEQUENCE: 12

Met Asp Lys Asp Pro Leu Leu Glu Glu Leu Glu Leu Arg Glu Arg
1               5                  10                 15

Leu Val His His Pro Gln Gly Gly Leu Leu Pro Leu Arg Gly Gln Val
                20                 25                 30

Gly His Asp Ala Glu Arg Leu Gly Ala Glu Val Asp Asp Leu Arg Gly
                35                 40                 45

Gly Leu Leu Asp Glu Pro Gln Arg Ala Val Ala Gly Leu His His Val
        50                 55                 60

Pro His Arg Val Gly Gln Arg Leu Val His Val Arg Glu Leu Asp
65                 70                 75                 80

Glu Gly Leu Leu Asp Gln Arg Asp Asp Leu Arg Gln Arg Leu Val Trp
                85                 90                 95
```

```
Arg Leu Pro Pro Ser
            100

<210> SEQ ID NO 13
<211> LENGTH: 102
<212> TYPE: PRT
<213> ORGANISM: Artificial Sequence
<220> FEATURE:
<223> OTHER INFORMATION: selected peptide

<400> SEQUENCE: 13

Met Glu Arg Glu Asp Pro Leu Asp Glu Gln Leu Arg Glu Leu Arg Glu
 1               5                  10                  15

Ala Leu Val Asp His Pro Gln Gly Gly Ala Gln Ala Leu His Arg His
            20                  25                  30

Asp Gly Gly Glu His Val Pro Leu Arg Arg Val Gln His Arg Leu Gln
        35                  40                  45

Pro Gly Leu Gln His His Leu Glu Pro Gln Pro Leu Gly Leu Leu Gly
    50                  55                  60

Glu Leu Gln Ala Arg Leu Gln Pro Leu Ala Gly Glu His Glu Gly Asp
65                  70                  75                  80

Gly Ala Gly Leu Gln Arg Val Pro Gly His Gln Gly Arg Arg Leu Val
                85                  90                  95

Trp Arg Leu Pro Pro Ser
            100

<210> SEQ ID NO 14
<211> LENGTH: 101
<212> TYPE: PRT
<213> ORGANISM: Artificial Sequence
<220> FEATURE:
<223> OTHER INFORMATION: selected peptide

<400> SEQUENCE: 14

Met Asp Glu Lys Thr His Arg Thr Leu Ser Val Ser Leu Ser Phe Asn
 1               5                  10                  15

Asp Trp Leu Gly Gln Thr Lys Ala Cys Trp Arg Leu Val Glu Gly Leu
            20                  25                  30

His Gly His Pro Gln Gly Leu Val Arg Glu His Glu Val Asp Val Leu
        35                  40                  45

Pro Leu Ala Glu Glu Val Gln Gln Val Val Gly Gly Leu Ala Asp Gly
    50                  55                  60

Val Glu Gln Pro Gly Gly Gly Leu Leu His Arg Ala Gln Arg Val Asp
65                  70                  75                  80

His Pro Leu Pro Asp His Ala Gly Gln Val Leu Gly Arg Leu Val Trp
                85                  90                  95

Arg Leu Pro Pro Ser
            100

<210> SEQ ID NO 15
<211> LENGTH: 101
<212> TYPE: PRT
<213> ORGANISM: Artificial Sequence
<220> FEATURE:
<223> OTHER INFORMATION: selected peptide

<400> SEQUENCE: 15

Met Asp Glu Lys Thr His Trp Leu Glu Asp Leu Lys Gly Val Leu Lys
 1               5                  10                  15

Asp Cys Leu Lys Asp Leu Met Asp Phe Thr Lys Asp Cys Arg Ser Pro
```

-continued

```
                 20                  25                  30

Arg Val Gln Pro Gln Pro Leu Leu His His Asp Arg Gly Glu Pro Val
             35                  40                  45

Pro Leu Leu Arg Glu Ala Gly Arg Asp Leu Gly Gly Leu Gly Pro Arg
         50                  55                  60

Ala Pro Arg Gln Ala Arg Pro Leu His His Gly Arg His Asp Leu His
 65                  70                  75                  80

Glu Pro Leu Val Leu Gln Asp His Pro Gln Gly Gly Pro Leu Val Cys
                 85                  90                  95

Gly Cys His His His
            100

<210> SEQ ID NO 16
<211> LENGTH: 102
<212> TYPE: PRT
<213> ORGANISM: Artificial Sequence
<220> FEATURE:
<223> OTHER INFORMATION: selected peptide

<400> SEQUENCE: 16

Met Asp Glu Lys Thr His Trp Val Leu Gln Leu His Pro Gln Gly Asp
 1               5                  10                  15

Arg Leu Gly Pro Arg His Gly Gly Asp Asp Val Arg Leu Val Gly Gln
             20                  25                  30

Gly Glu Gly Val Leu Glu Gly Leu Asp Gly Arg Pro Arg Arg Arg Arg
         35                  40                  45

His Arg Leu Pro Arg Glu Asp Glu His Arg Val Arg Ala Leu Val Asp
 50                  55                  60

Gln Val Arg Asp Leu Ala Glu Arg Leu Val Glu Glu Val Asp Gly Gly
 65                  70                  75                  80

Val Glu Ala Leu Arg His Leu Gly Leu Pro Gln Asp Glu Pro Arg Ser
                 85                  90                  95

Gly Gly Cys His His His
            100

<210> SEQ ID NO 17
<211> LENGTH: 102
<212> TYPE: PRT
<213> ORGANISM: Artificial Sequence
<220> FEATURE:
<223> OTHER INFORMATION: selected peptide

<400> SEQUENCE: 17

Met Asp Glu Lys Thr His Trp Val Gly Asp Leu Gln Glu Pro Leu Gly
 1               5                  10                  15

Pro Leu His Gly Gly Val Gly Glu Val Pro Gly Gly Leu Val Leu Arg
             20                  25                  30

His His Pro Gln Arg Asp Arg Leu Val Asp Gly Val Gly Pro His Gly
         35                  40                  45

Arg Ala Leu Ala Arg Arg Pro His Arg Val Val Glu Gly Leu His His
 50                  55                  60

Leu Leu Gln Arg Gly Gly Glu Arg Leu Pro Pro Asp Gly Pro Arg Gln
 65                  70                  75                  80

Leu Gly Leu Leu Gly Gly Glu Leu Asp Arg Ala Asp Pro Ala Leu Val
                 85                  90                  95

Trp Arg Leu Pro Pro Ser
            100
```

-continued

```
<210> SEQ ID NO 18
<211> LENGTH: 101
<212> TYPE: PRT
<213> ORGANISM: Artificial Sequence
<220> FEATURE:
<223> OTHER INFORMATION: selected peptide

<400> SEQUENCE: 18

Met Asp Glu Lys Thr His Cys Ala Val Asn Val Asn Val Gly Leu Thr
 1               5                  10                  15

His Trp Cys His Arg Val Ala His Leu Gln Pro Leu Asp Pro His Pro
             20                  25                  30

Gln Gly Asp His Leu Arg Leu Glu Pro Leu Gly His Ala Leu Val Asp
         35                  40                  45

Pro Leu Val Gln Gly Val Glu Val Val Arg Pro Leu Gln Leu Asp
     50                  55                  60

Val Gly Val Gln Arg Val Ala Leu Val Glu Gln Val Ala Glu Val Gly
 65                  70                  75                  80

Glu Gly Leu Asp His Glu Ala Gly Gln Ala His Gly Ala Leu Val Trp
                 85                  90                  95

Arg Leu Pro Pro Ser
            100

<210> SEQ ID NO 19
<211> LENGTH: 101
<212> TYPE: PRT
<213> ORGANISM: Artificial Sequence
<220> FEATURE:
<223> OTHER INFORMATION: selected peptide

<400> SEQUENCE: 19

Met Asp Glu Lys Thr Thr Gly Trp Arg Gly Gly His Val Val Glu Gly
 1               5                  10                  15

Leu Ala Gly Glu Leu Glu Gln Leu Arg Ala Arg Leu Glu His His Pro
             20                  25                  30

Gln Gly Gln Arg Glu Pro Leu Val Gln Glu Val Glu Asp Val Asp Glu
         35                  40                  45

Gly Leu Val Gln Asp Leu His Gly Val Val Ala Gly Leu Leu Asp Pro
     50                  55                  60

Val Glu Lys Leu Leu Thr Asp Trp Phe Lys Lys Phe Lys Asn Val Ser
 65                  70                  75                  80

Lys Asp Cys Lys Met Thr Phe Tyr Leu Glu Met Tyr Asp Trp Ser Gly
                 85                  90                  95

Gly Cys His His His
            100

<210> SEQ ID NO 20
<211> LENGTH: 102
<212> TYPE: PRT
<213> ORGANISM: Artificial Sequence
<220> FEATURE:
<223> OTHER INFORMATION: selected peptide

<400> SEQUENCE: 20

Met Asn Glu Lys Thr His Cys Lys Leu Asn Phe Lys Val Asn Ile Ala
 1               5                  10                  15

Asp Trp Leu Ala Glu Phe His Gly Gly Gln Gly Leu Leu Gly Arg
             20                  25                  30

Arg Asp Gly Val Val Gln Arg Leu Val Asp Gly Val Gln Glu Arg Val
```

```
              35                  40                  45
Glu Arg Leu Asp Arg Asp Pro Gly Leu Gly Asp Leu Arg Leu Glu Leu
         50                  55                  60

His His Arg Asp His Arg Leu Arg Leu Gly Gly Glu His Leu Leu Arg
 65                  70                  75                  80

Asp His Pro Leu Glu Pro Asp Asp His Leu Val Val Gly Gly Leu Val
                 85                  90                  95

Trp Arg Leu Pro Pro Ser
            100
```

<210> SEQ ID NO 21
<211> LENGTH: 101
<212> TYPE: PRT
<213> ORGANISM: Artificial Sequence
<220> FEATURE:
<223> OTHER INFORMATION: selected peptide

<400> SEQUENCE: 21

```
Met Asp Glu Lys Thr Thr Gly Trp Arg Gly Gly His Val Val Glu Gly
  1               5                  10                  15

Leu Ala Gly Glu Leu Glu Gln Leu Arg Ala Arg Leu Glu His His Pro
             20                  25                  30

Gln Gly Gln Arg Glu Pro Leu Val Gln Glu Val Glu Asp Val Asp Glu
         35                  40                  45

Gly Leu Val Gln Asp Leu His Gly Val Val Ala Gly Leu Leu Asp Pro
     50                  55                  60

Val Glu Lys Leu Leu Thr Asp Trp Phe Lys Lys Phe Lys Asn Val Ser
 65                  70                  75                  80

Lys Asp Cys Lys Met Thr Phe Tyr Leu Glu Met Tyr Asp Trp Ser Gly
                 85                  90                  95

Gly Cys Lys Leu Gly
            100
```

<210> SEQ ID NO 22
<211> LENGTH: 89
<212> TYPE: PRT
<213> ORGANISM: Artificial Sequence
<220> FEATURE:
<223> OTHER INFORMATION: selected peptide

<400> SEQUENCE: 22

```
Met Asp Glu Lys Thr Thr Gly Trp Arg Gly Gly His Val Val Glu Gly
  1               5                  10                  15

Leu Ala Gly Glu Leu Glu Gln Leu Arg Ala Arg Leu Glu His His Pro
             20                  25                  30

Gln Gly Gln Arg Glu Pro Leu Val Gln Glu Val Glu Asp Val Asp Glu
         35                  40                  45

Gly Leu Val Gln Asp Leu His Gly Val Val Ala Gly Leu Leu Asp Pro
     50                  55                  60

Val Glu Lys Leu Leu Thr Asp Trp Phe Lys Lys Phe Lys Asn Val Ser
 65                  70                  75                  80

Met Met Ser Gly Gly Cys Lys Leu Gly
                 85
```

<210> SEQ ID NO 23
<211> LENGTH: 75
<212> TYPE: PRT
<213> ORGANISM: Artificial Sequence
<220> FEATURE:

-continued

<223> OTHER INFORMATION: selected peptide

<400> SEQUENCE: 23

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro Leu Val Gln Glu Val Glu Asp Val Asp Glu
        35                  40                  45

Gly Leu Val Gln Asp Leu His Gly Val Val Ala Gly Leu Leu Asp Pro
    50                  55                  60

Val Glu Met Met Ser Gly Gly Cys Lys Leu Gly
65                  70                  75

<210> SEQ ID NO 24
<211> LENGTH: 61
<212> TYPE: PRT
<213> ORGANISM: Artificial Sequence
<220> FEATURE:
<223> OTHER INFORMATION: selected peptide

<400> SEQUENCE: 24

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro Leu Val Gln Glu Val Glu Asp Val Asp Glu
        35                  40                  45

Gly Leu Val Gln Met Met Ser Gly Gly Cys Lys Leu Gly
    50                  55                  60

<210> SEQ ID NO 25
<211> LENGTH: 47
<212> TYPE: PRT
<213> ORGANISM: Artificial Sequence
<220> FEATURE:
<223> OTHER INFORMATION: selected peptide

<400> SEQUENCE: 25

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro Met Met Ser Gly Gly Cys Lys Leu Gly
        35                  40                  45

<210> SEQ ID NO 26
<211> LENGTH: 47
<212> TYPE: PRT
<213> ORGANISM: Artificial Sequence
<220> FEATURE:
<223> OTHER INFORMATION: selected peptide

<400> SEQUENCE: 26

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Gly
            20                  25                  30

Ala Gly Gln Arg Glu Pro Met Met Ser Gly Gly Cys Lys Leu Gly
        35                  40                  45

<210> SEQ ID NO 27
<211> LENGTH: 39
<212> TYPE: PRT
<213> ORGANISM: Artificial Sequence
<220> FEATURE:
<223> OTHER INFORMATION: selected peptide

<400> SEQUENCE: 27

Met Asp Gly His Val Val Glu Gly Leu Ala Gly Glu Leu Glu Gln Leu
1               5                   10                  15

Arg Ala Arg Leu Glu His His Pro Gln Gly Gln Arg Glu Pro Met Met
            20                  25                  30

Ser Gly Gly Cys Lys Leu Gly
        35

<210> SEQ ID NO 28
<211> LENGTH: 89
<212> TYPE: PRT
<213> ORGANISM: Artificial Sequence
<220> FEATURE:
<223> OTHER INFORMATION: selected peptide

<400> SEQUENCE: 28

Met Asp Glu Gly Leu Ala Gly Glu Leu Glu Gln Leu Arg Ala Arg Leu
1               5                   10                  15

Glu His His Pro Gln Gly Gln Arg Glu Pro Leu Val Gln Glu Val Glu
            20                  25                  30

Asp Val Asp Glu Gly Leu Val Gln Asp Leu His Gly Val Val Ala Gly
            35                  40                  45

Leu Leu Asp Pro Val Glu Lys Leu Leu Thr Asp Trp Phe Lys Lys Phe
50                  55                  60

Lys Asn Val Ser Lys Asp Cys Lys Met Thr Phe Tyr Leu Glu Met Tyr
65                  70                  75                  80

Asp Trp Ser Gly Gly Cys Lys Leu Gly
                85

<210> SEQ ID NO 29
<211> LENGTH: 29
<212> TYPE: PRT
<213> ORGANISM: Artificial Sequence
<220> FEATURE:
<223> OTHER INFORMATION: selected peptide

<400> SEQUENCE: 29

Met Glu Leu Glu Gln Leu Arg Ala Arg Leu Glu His His Pro Gln Gly
1               5                   10                  15

Gln Arg Glu Pro Met Met Ser Gly Gly Cys Lys Leu Gly
            20                  25

<210> SEQ ID NO 30
<211> LENGTH: 35
<212> TYPE: DNA
<213> ORGANISM: Artificial Sequence
<220> FEATURE:
<223> OTHER INFORMATION: primer

<400> SEQUENCE: 30
atagccggtg ccaagcttgc agccgccaga ccagt                          35

<210> SEQ ID NO 31
<211> LENGTH: 35
<212> TYPE: DNA

```
<213> ORGANISM: Artificial Sequence
<220> FEATURE:
<223> OTHER INFORMATION: primer

<400> SEQUENCE: 31 acugguugg cggcugcaag cuuggcaccg gcuau                         35

<210> SEQ ID NO 32
<211> LENGTH: 14
<212> TYPE: PRT
<213> ORGANISM: Artificial Sequence
<220> FEATURE:
<223> OTHER INFORMATION: selected peptide

<400> SEQUENCE: 32

Trp Ser Gly Gly Cys His His His His His Ser Ser Ala
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: designed peptide

<400> SEQUENCE: 33

Trp Ser Gly Gly Cys Lys Leu Gly Thr Gly Tyr
 1               5                  10

<210> SEQ ID NO 34
<211> LENGTH: 44
<212> TYPE: PRT
<213> ORGANISM: Artificial Sequence
<220> FEATURE:
<223> OTHER INFORMATION: designed peptide

<400> SEQUENCE: 34

Met Asp Glu Ala His Pro Gln Ala Gly Pro Val Asp Gln Ala Asp Ala
 1               5                  10                  15

Arg Leu Val Gln Gln Gly Ala Leu Gln His His Pro Gln Gly Asp Arg
             20                  25                  30

Met Met Ser Gly Gly Cys Lys Leu Gly Thr Gly Tyr
         35                  40

<210> SEQ ID NO 35
<211> LENGTH: 38
<212> TYPE: PRT
<213> ORGANISM: Artificial Sequence
<220> FEATURE:
<223> OTHER INFORMATION: selected peptide

<400> SEQUENCE: 35

Met Asp Glu Lys Thr Thr Gly Trp Arg Gly Gly His Val Val Glu Gly
 1               5                  10                  15

Leu Ala Gly Glu Leu Glu Gln Leu Arg Ala Arg Leu Glu His His Pro
             20                  25                  30

Gln Gly Gln Arg Glu Pro
         35

<210> SEQ ID NO 36
<211> LENGTH: 9
<212> TYPE: PRT
<213> ORGANISM: Artificial Sequence
<220> FEATURE:
<223> OTHER INFORMATION: designed peptide
```

-continued

```
<400> SEQUENCE: 36

Met Met Ser Gly Gly Cys Lys Leu Gly
  1               5

<210> SEQ ID NO 37
<211> LENGTH: 6688
<212> TYPE: DNA
<213> ORGANISM: Artificial Sequence
<220> FEATURE:
<223> OTHER INFORMATION: plasmid

<400> SEQUENCE: 37
atccggatat agttcctcct ttcagcaaaa aacccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagctttt     180
agtcgtcatg tccatgatag gtgtcgtccc cgatatcaat gctattgtta aagcaggtct     240
tacacatgtt atagatcctc aaatgcttgt tcttcacctt ccagttccgg ggagccacct     300
tgcatttcac acaagggtcc atgctacctc ggggtaccaa gaattcgtga tgatggtgat     360
ggtgaccgga tcctggttca cgttgacctt gtgggtgatg ctccagtcgt gcacgaagtt     420
gttcaagttc cccagccagt ccttcaacaa cgtgtccacc tcgccaacca gtggtcttct     480
cgtccatccc tgagccgcta cctcctgagc tcgaattagt ctgcgcgtct ttcagggctt     540
catcgacagt ctgacgaccg ctggcggcgt tgatcaccgc agtacgcacg gcataccaga     600
aagcggacat ctgcgggatg ttcggcatga tttcaccttt ctgggcgttt tccattgtgg     660
cggcaatacg tggatctttc gccaactctt cctcgtaaga cttcagcgct acggcaccca     720
gcggtttgtc tttattaacc gcttccagac cttcatcagt cagcagatag ttttcgagga     780
actcttttgc cagctctttg ttcggactgg cggcgttaat acctgcgctc agcacgccaa     840
cgaacggttt ggatggttga cccttgaagg tcggcagtac cgttacacca taattcactt     900
tgctggtgtc gatgttggac catgcccacg ggccgttgat ggtcatcgct gtttcgcctt     960
tattaaaggc agcttctgcg atggagtaat cggtgtctgc attcatgtgt ttgttttaa    1020
tcaggtcaac caggaaggtc agacccgctt tcgcgccagc gttatccacg cccacgtctt    1080
taatgtcgta cttgccgttt tcatacttga acgcataacc cccgtcagca gcaatcagcg    1140
gccaggtgaa gtacggttct tgcaggttga acatcagcgc gctcttacct ttcgctttca    1200
gttctttatc cagcgccggg atctcttccc aggtttttgg cgggttcggc agcagatctt    1260
tgttataaat cagcgataac gcttcaacag cgatcgggta agcaatcagc ttgccgttgt    1320
aacgtacggc atcccaggta aacgatacca gcttgtcctg aacgctttg tccggggtga    1380
tttcagccaa caggccagat tgagcgtagc caccaaagcg gtcgtgtgcc cagaagataa    1440
tgtcagggcc atcgccagtt gccgcaacct gtgggaattt ctcttccagt ttatccggat    1500
gctcaacggt gactttaatt ccggtatctt tctcgaattt cttaccgact tcagcgagac    1560
cgttatagcc tttatcgccg ttaatccaga ttaccagttt accttcttcg attcccatgg    1620
tatatctcct tcttaaagtt aaacaaaatt atttctagag gggaattgtt atccgctcac    1680
aattccccta tagtgagtcg tattaatttc gcgggatcga gatctcgatc ctctacgccg    1740
gacgcatcgt ggccggcatc accggcgcca caggtgcggt tgctggcgcc tatatcgccg    1800
acatcaccga tggggaagat cgggctcgcc acttcgggct catgagcgct tgtttcggcg    1860
tgggtatggt ggcaggcccc gtggccgggg gactgttggg cgccatctcc ttgcatgcac    1920
```

-continued

```
cattccttgc ggcggcggtg ctcaacggcc tcaacctact actgggctgc ttcctaatgc    1980
aggagtcgca taagggagag cgtcgagatc ccggacacca tcgaatggcg caaaaccttt    2040
cgcggtatgg catgatagcg cccggaagag agtcaattca gggtggtgaa tgtgaaacca    2100
gtaacgttat acgatgtcgc agagtatgcc ggtgtctctt atcagaccgt ttcccgcgtg    2160
gtgaaccagg ccagccacgt ttctgcgaaa acgcgggaaa aagtggaagc ggcgatggcg    2220
gagctgaatt acattcccaa ccgcgtggca caacaactgg cgggcaaaca gtcgttgctg    2280
attggcgttg ccacctccag tctggccctg cacgcgccgt cgcaaattgt cgcggcgatt    2340
aaatctcgcg ccgatcaact gggtgccagc gtggtggtgt cgatggtaga acgaagcggc    2400
gtcgaagcct gtaaagcggc ggtgcacaat cttctcgcgc aacgcgtcag tgggctgatc    2460
attaactatc cgctggatga ccaggatgcc attgctgtgg aagctgcctg cactaatgtt    2520
ccggcgttat ttcttgatgt ctctgaccag acacccatca acagtattat tttctcccat    2580
gaagacggta cgcgactggg cgtggagcat ctggtcgcat gggtcacca gcaaatcgcg    2640
ctgttagcgg gcccattaag ttctgtctcg gcgcgtctgc gtctggctgg ctggcataaa    2700
tatctcactc gcaatcaaat tcagccgata gcggaacggg aaggcgactg gagtgccatg    2760
tccggttttc aacaaaccat gcaaatgctg aatgagggca tcgttcccac tgcgatgctg    2820
gttgccaacg atcagatggc gctgggcgca atgcgcgcca ttaccgagtc cgggctgcgc    2880
gttggtgcgg atatctcggt agtgggatac gacgataccg aagacagctc atgttatatc    2940
ccgccgttaa ccaccatcaa acaggatttt cgcctgctgg ggcaaaccag cgtggaccgc    3000
ttgctgcaac tctctcaggg ccaggcggtg aagggcaatc agctgttgcc cgtctcactg    3060
gtgaaaagaa aaaccaccct ggcgcccaat acgcaaaccg cctctccccg cgcgttggcc    3120
gattcattaa tgcagctggc acgacaggtt tcccgactgg aaagcgggca gtgagcgcaa    3180
cgcaattaat gtaagttagc tcactcatta ggcaccggga tctcgaccga tgcccttgag    3240
agccttcaac ccagtcagct ccttccggtg ggcgcgggc atgactatcg tcgccgcact    3300
tatgactgtc ttctttatca tgcaactcgt aggacaggtg ccggcagcgc tctgggtcat    3360
tttcggcgag gaccgctttc gctggagcgc gacgatgatc ggcctgtcgc ttgcggtatt    3420
cggaatcttg cacgccctcg ctcaagcctt cgtcactggt cccgccacca acgtttcgg    3480
cgagaagcag gccattatcg ccggcatggc ggcccacgg gtgcgcatga tcgtgctcct    3540
gtcgttgagg acccggctag gctggcgggg ttgccttact ggttagcaga atgaatcacc    3600
gatacgcgag cgaacgtgaa gcgactgctg ctgcaaaacg tctgcgacct gagcaacaac    3660
atgaatggtc ttcggtttcc gtgtttcgta aagtctggaa acgcggaagt cagcgccctg    3720
caccattatg ttccggatct gcatcgcagg atgctgctgg ctaccctgtg aacacctac    3780
atctgtatta cgaagcgct ggcattgacc ctgagtgatt tttctctggt cccgccgcat    3840
ccataccgcc agttgtttac cctcacaacg ttccagtaac cgggcatgtt catcatcagt    3900
aacccgtatc gtgagcatcc tctctcgttt catcggtatc attaccccca tgaacagaaa    3960
tcccccttac acggaggcat cagtgaccaa acaggaaaaa accgccctta acatggcccg    4020
ctttatcaga agccagacat taacgcttct ggagaaactc aacgagctgg acgcggatga    4080
acaggcagac atctgtgaat cgcttcacga ccacgctgat gagctttacc gcagctgcct    4140
cgcgcgtttc ggtgatgacg gtgaaaacct ctgacacatg cagctcccgg agacggtcac    4200
agcttgtctg taagcggatg ccgggagcag acaagcccgt cagggcgcgt cagcgggtgt    4260
```

```
tggcgggtgt cggggcgcag ccatgaccca gtcacgtagc gatagcggag tgtatactgg    4320
cttaactatg cggcatcaga gcagattgta ctgagagtgc accatatatg cggtgtgaaa    4380
taccgcacag atgcgtaagg agaaaatacc gcatcaggcg ctcttccgct tcctcgctca    4440
ctgactcgct gcgctcggtc gttcggctgc ggcgagcggt atcagctcac tcaaaggcgg    4500
taatacggtt atccacagaa tcaggggata acgcaggaaa gaacatgtga gcaaaaggcc    4560
agcaaaaggc caggaaccgt aaaaaggccg cgttgctggc gtttttccat aggctccgcc    4620
cccctgacga gcatcacaaa aatcgacgct caagtcagag gtggcgaaac ccgacaggac    4680
tataaagata ccaggcgttt ccccctggaa gctccctcgt gcgctctcct gttccgaccc    4740
tgccgcttac cggatacctg tccgcctttc tcccttcggg aagcgtggcg ctttctcata    4800
gctcacgctg taggtatctc agttcggtgt aggtcgttcg ctccaagctg ggctgtgtgc    4860
acgaacccc cgttcagccc gaccgctgcg ccttatccgg taactatcgt cttgagtcca    4920
acccggtaag acacgactta tcgccactgg cagcagccac tggtaacagg attagcagag    4980
cgaggtatgt aggcggtgct acagagttct tgaagtggtg gcctaactac ggctacacta    5040
gaaggacagt atttggtatc tgcgctctgc tgaagccagt taccttcgga aaaagagttg    5100
gtagctcttg atccggcaaa caaaccaccg ctggtagcgg tggttttttt gtttgcaagc    5160
agcagattac gcgcagaaaa aaaggatctc aagaagatcc tttgatcttt tctacggggt    5220
ctgacgctca gtggaacgaa aactcacgtt aagggatttt ggtcatgaac aataaaactg    5280
tctgcttaca taaacagtaa tacaaggggg gttatgagcc atattcaacg ggaaacgtct    5340
tgctctaggc cgcgattaaa ttccaacatg gatgctgatt tatatgggta taaatgggct    5400
cgcgataatg tcgggcaatc aggtgcgaca atctatcgat tgtatgggaa gcccgatgcg    5460
ccagagttgt ttctgaaaca tggcaaaggt agcgttgcca atgatgttac agatgagatg    5520
gtcagactaa actggctgac ggaatttatg cctcttccga ccatcaagca ttttatccgt    5580
actcctgatg atgcatggtt actcaccact gcgatccccg ggaaaacagc attccaggta    5640
ttagaagaat atcctgattc aggtgaaaat attgttgatg cgctggcagt gttcctgcgc    5700
cggttgcatt cgattcctgt ttgtaattgt ccttttaaca gcgatcgcgt atttcgtctc    5760
gctcaggcgc aatcacgaat gaataacggt ttggttgatg cgagtgattt tgatgacgag    5820
cgtaatggct ggcctgttga acaagtctgg aaagaaatgc ataaactttt gccattctca    5880
ccggattcag tcgtcactca tggtgatttc tcacttgata accttatttt tgacgagggg    5940
aaattaatag gttgtattga tgttggacga gtcggaatcg cagaccgata ccaggatctt    6000
gccatcctat ggaactgcct cggtgagttt ctccttcat acagaaacg gcttttttcaa    6060
aaatatggta ttgataatcc tgatatgaat aaattgcagt ttcatttgat gctcgatgag    6120
tttttctaag aattaattca tgagcggata catatttgaa tgtatttaga aaaataaaca    6180
aataggggtt ccgcgcacat ttccccgaaa agtgccacct gaaattgtaa acgttaatat    6240
tttgttaaaa ttcgcgttaa atttttgtta aatcagctca ttttttaacc aataggccga    6300
aatcggcaaa atcccttata aatcaaaaga atagaccgag atagggttga gtgttgttcc    6360
agtttggaac aagagtccac tattaaagaa cgtggactcc aacgtcaaag ggcgaaaaac    6420
cgtctatcag ggcgatggcc cactacgtga accatcaccc taatcaagtt ttttggggtc    6480
gaggtgccgt aaagcactaa atcggaaccc taaagggagc cccgatttag agcttgacg    6540
gggaagccg cgaacgtgg cgagaaagga agggaagaaa gcgaaaggag cgggcgctag    6600
ggcgctggca agtgtagcgg tcacgctgcg cgtaaccacc acacccgccg cgcttaatgc    6660
```

```
<210> SEQ ID NO 38
<211> LENGTH: 479
<212> TYPE: PRT
<213> ORGANISM: Artificial Sequence
<220> FEATURE:
<223> OTHER INFORMATION: Designed protein

<400> SEQUENCE: 38
```

| | | | | | | | | | | | | | | |
|---|---|---|---|---|---|---|---|---|---|---|---|---|---|---|
| Met | Gly | Ile | Glu | Glu | Gly | Lys | Leu | Val | Ile | Trp | Ile | Asn | Gly | Asp | Lys |
| 1 | | | | 5 | | | | | 10 | | | | | 15 | |
| Gly | Tyr | Asn | Gly | Leu | Ala | Glu | Val | Gly | Lys | Lys | Phe | Glu | Lys | Asp | Thr |
| | | | 20 | | | | | 25 | | | | | 30 | | |
| Gly | Ile | Lys | Val | Thr | Val | Glu | His | Pro | Asp | Lys | Leu | Glu | Glu | Lys | Phe |
| | | | 35 | | | | | 40 | | | | | 45 | | |
| Pro | Gln | Val | Ala | Ala | Thr | Gly | Asp | Gly | Pro | Asp | Ile | Ile | Phe | Trp | Ala |
| | 50 | | | | | 55 | | | | | 60 | | | | |
| His | Asp | Arg | Phe | Gly | Gly | Tyr | Ala | Gln | Ser | Gly | Leu | Leu | Ala | Glu | Ile |
| 65 | | | | | 70 | | | | | 75 | | | | | 80 |
| Thr | Pro | Asp | Lys | Ala | Phe | Gln | Asp | Lys | Leu | Tyr | Pro | Phe | Thr | Trp | Asp |
| | | | | 85 | | | | | 90 | | | | | 95 | |
| Ala | Val | Arg | Tyr | Asn | Gly | Lys | Leu | Ile | Ala | Tyr | Pro | Ile | Ala | Val | Glu |
| | | | 100 | | | | | 105 | | | | | 110 | | |
| Ala | Leu | Ser | Leu | Ile | Tyr | Asn | Lys | Asp | Leu | Leu | Pro | Asn | Pro | Pro | Lys |
| | | | 115 | | | | | 120 | | | | | 125 | | |
| Thr | Trp | Glu | Glu | Ile | Pro | Ala | Leu | Asp | Lys | Glu | Leu | Lys | Ala | Lys | Gly |
| | 130 | | | | | 135 | | | | | 140 | | | | |
| Lys | Ser | Ala | Leu | Met | Phe | Asn | Leu | Gln | Glu | Pro | Tyr | Phe | Thr | Trp | Pro |
| 145 | | | | | 150 | | | | | 155 | | | | | 160 |
| Leu | Ile | Ala | Ala | Asp | Gly | Gly | Tyr | Ala | Phe | Lys | Tyr | Glu | Asn | Gly | Lys |
| | | | | 165 | | | | | 170 | | | | | 175 | |
| Tyr | Asp | Ile | Lys | Asp | Val | Gly | Val | Asp | Asn | Ala | Gly | Ala | Lys | Ala | Gly |
| | | | 180 | | | | | 185 | | | | | 190 | | |
| Leu | Thr | Phe | Leu | Val | Asp | Leu | Ile | Lys | Asn | Lys | His | Met | Asn | Ala | Asp |
| | | | 195 | | | | | 200 | | | | | 205 | | |
| Thr | Asp | Tyr | Ser | Ile | Ala | Glu | Ala | Ala | Phe | Asn | Lys | Gly | Glu | Thr | Ala |
| | 210 | | | | | 215 | | | | | 220 | | | | |
| Met | Thr | Ile | Asn | Gly | Pro | Trp | Ala | Trp | Ser | Asn | Ile | Asp | Thr | Ser | Lys |
| 225 | | | | | 230 | | | | | 235 | | | | | 240 |
| Val | Asn | Tyr | Gly | Val | Thr | Val | Leu | Pro | Thr | Phe | Lys | Gly | Gln | Pro | Ser |
| | | | | 245 | | | | | 250 | | | | | 255 | |
| Lys | Pro | Phe | Val | Gly | Val | Leu | Ser | Ala | Gly | Ile | Asn | Ala | Ala | Ser | Pro |
| | | | 260 | | | | | 265 | | | | | 270 | | |
| Asn | Lys | Glu | Leu | Ala | Lys | Glu | Phe | Leu | Glu | Asn | Tyr | Leu | Leu | Thr | Asp |
| | | | 275 | | | | | 280 | | | | | 285 | | |
| Glu | Gly | Leu | Glu | Ala | Val | Asn | Lys | Asp | Lys | Pro | Leu | Gly | Ala | Val | Ala |
| | 290 | | | | | 295 | | | | | 300 | | | | |
| Leu | Lys | Ser | Tyr | Glu | Glu | Leu | Ala | Lys | Asp | Pro | Arg | Ile | Ala | Ala |
| 305 | | | | | 310 | | | | | 315 | | | | | 320 |
| Thr | Met | Glu | Asn | Ala | Gln | Lys | Gly | Glu | Ile | Met | Pro | Asn | Ile | Pro | Gln |
| | | | | 325 | | | | | 330 | | | | | 335 | |
| Met | Ser | Ala | Phe | Trp | Tyr | Ala | Val | Arg | Thr | Ala | Val | Ile | Asn | Ala | Ala |
| | | | 340 | | | | | 345 | | | | | 350 | | |

-continued

Ser Gly Arg Gln Thr Val Asp Glu Ala Leu Lys Asp Ala Gln Thr Asn
        355                 360                 365
Ser Ser Ser Gly Gly Ser Gly Ser Gly Met Asp Glu Lys Thr Thr Gly
    370                 375                 380
Trp Arg Gly Gly His Val Val Glu Gly Leu Ala Gly Glu Leu Glu Gln
385                 390                 395                 400
Leu Arg Ala Arg Leu Glu His His Pro Gln Gly Gln Arg Glu Pro Gly
                405                 410                 415
Ser Gly His His His His His Glu Phe Leu Val Pro Arg Gly Ser
        420                 425                 430
Met Asp Pro Cys Val Lys Cys Lys Val Ala Pro Arg Asn Trp Lys Val
        435                 440                 445
Lys Asn Lys His Leu Arg Ile Tyr Asn Met Cys Lys Thr Cys Phe Asn
    450                 455                 460
Asn Ser Ile Asp Ile Gly Asp Asp Thr Tyr His Gly His Asp Asp
465                 470                 475

<210> SEQ ID NO 39
<211> LENGTH: 47
<212> TYPE: PRT
<213> ORGANISM: Artificial Sequence
<220> FEATURE:
<223> OTHER INFORMATION: Selected peptide

<400> SEQUENCE: 39

Met Asp Pro Cys Val Lys Cys Lys Val Ala Pro Arg Asn Trp Lys Val
1               5                   10                  15
Lys Asn Lys His Leu Arg Ile Tyr Asn Met Cys Lys Thr Cys Phe Asn
            20                  25                  30
Asn Ser Ile Asp Ile Gly Asp Asp Thr Tyr His Gly His Asp Asp
        35                  40                  45

<210> SEQ ID NO 40
<211> LENGTH: 6544
<212> TYPE: DNA
<213> ORGANISM: Artificial Sequence
<220> FEATURE:
<223> OTHER INFORMATION: plasmid

<400> SEQUENCE: 40
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttca     180
gctgcgaagc ttattagaat tcgtgatgat ggtgatggtg accggatcct ggttcacgtt     240
gaccttgtgg gtgatgctcc agtcgtgcac gaagttgttc aagttcccca gccagtcctt     300
caacaacgtg tccacctcgc caaccagtgg tcttctcgtc catccctgag ccgctacctc     360
ctgagctcga attagtctgc gcgtctttca gggcttcatc gacagtctga cgaccgctgg     420
cggcgttgat caccgcagta cgcacggcat accagaaagc ggacatctgc gggatgttcg     480
gcatgatttc acctttctgg gcgttttcca ttgtggcggc aatacgtgga tctttcgcca     540
actcttcctc gtaagacttc agcgctacgg cacccagcgg tttgtcttta ttaaccgctt     600
ccagaccttc atcagtcagc agatagtttt cgaggaactc ttttgccagc tctttgttcg     660
gactggcggc gttaatacct gcgctcagca cgccaacgaa cggtttggat ggttgaccct     720
tgaaggtcgg cagtaccgtt acaccataat tcactttgct ggtgtcgatg ttggaccatg     780

```
cccacgggcc gttgatggtc atcgctgttt cgcctttatt aaaggcagct tctgcgatgg   840
agtaatcggt gtctgcattc atgtgtttgt ttttaatcag gtcaaccagg aaggtcagac   900
ccgctttcgc gccagcgtta tccacgccca cgtctttaat gtcgtacttg ccgttttcat   960
acttgaacgc ataacccccg tcagcagcaa tcagcggcca ggtgaagtac ggttcttgca  1020
ggttgaacat cagcgcgctc ttacctttcg ctttcagttc tttatccagc gccgggatct  1080
cttcccaggt ttttggcggg ttcggcagca gatctttgtt ataaatcagc gataacgctt  1140
caacagcgat cgggtaagca atcagcttgc cgttgtaacg tacggcatcc caggtaaacg  1200
gatacagctt gtcctggaac gctttgtccg ggtgatttc agccaacagg ccagattgag  1260
cgtagccacc aaagcggtcg tgtgcccaga agataatgtc agggccatcg ccagttgccg  1320
caacctgtgg gaatttctct tccagtttat ccggatgctc aacggtgact ttaattccgg  1380
tatctttctc gaatttctta ccgacttcag cgagaccgtt atagccttta tcgccgttaa  1440
tccagattac cagtttacct tcttcgattc ccatggtata tctccttctt aaagttaaac  1500
aaaattattt ctagagggga attgttatcc gctcacaatt ccctatagt gagtcgtatt  1560 aatttcgcgg gatcgagatc tcgatcctct acgccgacg catcgtggcc ggcatcaccg  1620
gcgccacagg tgcggttgct ggcgcctata tcgccgacat caccgatggg gaagatcggg  1680
ctcgccactt cgggctcatg agcgcttgtt tcggcgtggg tatggtggca ggccccgtgg  1740
ccgggggact gttgggcgcc atctccttgc atgcaccatt ccttgcggcg gcggtgctca  1800
acggcctcaa cctactactg gctgcttcc taatgcagga gtcgcataag ggagagcgtc  1860
gagatcccgg acaccatcga atggcgcaaa acctttcgcg gtatggcatg atagcgcccg  1920
gaagagagtc aattcagggt ggtgaatgtg aaaccagtaa cgttatacga tgtcgcagag  1980
tatgccggtg tctcttatca gaccgtttcc cgcgtggtga accaggccag ccacgtttct  2040 gcgaaacgc gggaaaaagt ggaagcggcg atggcggagc tgaattacat tcccaaccgc  2100
gtggcacaac aactggcggg caaacagtcg ttgctgattg gcgttgccac ctccagtctg  2160
gccctgcacg cgccgtcgca aattgtcgcg gcgattaaat ctcgcgccga tcaactgggt  2220
gccagcgtgg tggtgtcgat ggtagaacga agcggcgtcg aagcctgtaa agcggcggtg  2280
cacaatcttc tcgcgcaacg cgtcagtggg ctgatcatta actatccgct ggatgaccag  2340
gatgccattg ctgtggaagc tgcctgcact aatgttccgg cgttatttct tgatgtctct  2400
gaccagacac ccatcaacag tattattttc tcccatgaag acggtacgcg actgggcgtg  2460
gagcatctgg tcgcattggg tcaccagcaa atcgcgctgt tagcgggccc attaagttct  2520
gtctcggcgc gtctgcgtct ggctggctgg cataaatatc tcactcgcaa tcaaattcag  2580
ccgatagcgg aacgggaagg cgactggagt gccatgtccg gttttcaaca aaccatgcaa  2640
atgctgaatg agggcatcgt tcccactgcg atgctggttg ccaacgatca gatggcgctg  2700
ggcgcaatgc gcgccattac cgagtccggg ctgcgcgttg gtgcggatat ctcggtagtg  2760
ggatacgacg ataccgaaga cagctcatgt tatatcccgc cgttaaccac catcaaacag  2820
gattttcgcc tgctggggca aaccagcgtg gaccgcttgc tgcaactctc tcagggccag  2880
gcggtgaagg gcaatcagct gttgcccgtc tcactggtga aaagaaaaac caccctggcg  2940
cccaatacgc aaaccgcctc tccccgcgcg ttggccgatt cattaatgca gctggcacga  3000
caggtttccc gactggaaag cgggcagtga gcgcaacgca attaatgtaa gttagctcac  3060
tcattaggca ccgggatctc gaccgatgcc cttgagagcc ttcaacccag tcagctcctt  3120
ccggtgggcg cggggcatga ctatcgtcgc cgcacttatg actgtcttct ttatcatgca  3180
```

```
actcgtagga caggtgccgg cagcgctctg ggtcattttc ggcgaggacc gctttcgctg    3240
gagcgcgacg atgatcggcc tgtcgcttgc ggtattcgga atcttgcacg ccctcgctca    3300
agccttcgtc actggtcccg ccaccaaacg tttcggcgag aagcaggcca ttatcgccgg    3360
catggcggcc ccacgggtgc gcatgatcgt gctcctgtcg ttgaggaccc ggctaggctg    3420
gcggggttgc cttactggtt agcagaatga atcaccgata cgcgagcgaa cgtgaagcga    3480
ctgctgctgc aaaacgtctg cgacctgagc aacaacatga atggtcttcg gtttccgtgt    3540
ttcgtaaagt ctggaaacgc ggaagtcagc gccctgcacc attatgttcc ggatctgcat    3600
cgcaggatgc tgctggctac cctgtggaac acctacatct gtattaacga agcgctggca    3660
ttgaccctga gtgatttttc tctggtcccg ccgcatccat accgccagtt gtttaccctc    3720
acaacgttcc agtaaccggg catgttcatc atcagtaacc cgtatcgtga gcatcctctc    3780
tcgtttcatc ggtatcatta cccccatgaa cagaaatccc ccttacacgg aggcatcagt    3840
gaccaaacag gaaaaaaccg cccttaacat ggcccgcttt atcagaagcc agacattaac    3900
gcttctggag aaactcaacg agctggacgc ggatgaacag gcagacatct gtgaatcgct    3960
tcacgaccac gctgatgagc tttaccgcag ctgcctcgcg cgtttcggtg atgacggtga    4020
aaacctctga cacatgcagc tcccggagac ggtcacagct tgtctgtaag cggatgccgg    4080
gagcagacaa gcccgtcagg gcgcgtcagc gggtgttggc gggtgtcggg gcgcagccat    4140
gacccagtca cgtagcgata gcggagtgta tactggctta actatgcggc atcagagcag    4200
attgtactga gagtgcacca tatatgcggt gtgaaatacc gcacagatgc gtaaggagaa    4260
aataccgcat caggcgctct tccgcttcct cgctcactga ctcgctgcgc tcggtcgttc    4320
ggctgcggcg agcggtatca gctcactcaa aggcggtaat acggttatcc acagaatcag    4380
gggataacgc aggaaagaac atgtgagcaa aaggccagca aaaggccagg aaccgtaaaa    4440
aggccgcgtt gctggcgttt ttccataggc tccgccccc tgacgagcat cacaaaaatc    4500
gacgctcaag tcagaggtgg cgaaacccga caggactata agataccag gcgtttcccc    4560 ctggaagctc cctcgtgcgc tctcctgttc cgaccctgcc gcttaccgga tacctgtccg    4620
cctttctccc ttcgggaagc gtggcgcttt ctcatagctc acgctgtagg tatctcagtt    4680
cggtgtaggt cgttcgctcc aagctgggct gtgtgcacga accccccgtt cagcccgacc    4740
gctgcgcctt atccggtaac tatcgtcttg agtccaaccc ggtaagacac gacttatcgc    4800
cactggcagc agccactggt aacaggatta gcagagcgag gtatgtaggc ggtgctacag    4860
agttcttgaa gtggtggcct aactacggct acactagaag gacagtattt ggtatctgcg    4920
ctctgctgaa gccagttacc ttcggaaaaa gagttggtag ctcttgatcc ggcaaacaaa    4980
ccaccgctgg tagcggtggt ttttttgttt gcaagcagca gattacgcgc agaaaaaaag    5040
gatctcaaga agatcctttg atcttttcta cggggtctga cgctcagtgg aacgaaaact    5100
cacgttaagg gattttggtc atgaacaata aaactgtctg cttacataaa cagtaataca    5160 agggtgtta tgagccatat tcaacgggaa acgtcttgct ctaggccgcg attaaattcc    5220
aacatggatg ctgatttata tgggtataaa tgggctcgcg ataatgtcgg gcaatcaggt    5280
gcgacaatct atcgattgta tgggaagccc gatgcgccag agttgtttct gaaacatggc    5340
aaaggtagcg ttgccaatga tgttacagat gagatggtca gactaaactg gctgacggaa    5400
tttatgcctc ttccgaccat caagcatttt atccgtactc ctgatgatgc atggttactc    5460
accactgcga tccccgggaa aacagcattc caggtattag aagaatatcc tgattcaggt    5520
```

-continued

```
gaaaatattg ttgatgcgct ggcagtgttc ctgcgccggt tgcattcgat tcctgtttgt   5580
aattgtcctt ttaacagcga tcgcgtattt cgtctcgctc aggcgcaatc acgaatgaat   5640
aacggtttgg ttgatgcgag tgattttgat gacgagcgta atggctggcc tgttgaacaa   5700
gtctggaaag aaatgcataa acttttgcca ttctcaccgg attcagtcgt cactcatggt   5760
gatttctcac ttgataacct tatttttgac gagggaaat taataggttg tattgatgtt   5820
ggacgagtcg gaatcgcaga ccgataccag gatcttgcca tcctatggaa ctgcctcggt   5880
gagttttctc cttcattaca gaaacggctt tttcaaaaat atggtattga taatcctgat   5940
atgaataaat tgcagtttca tttgatgctc gatgagtttt tctaagaatt aattcatgag   6000
cggatacata tttgaatgta tttagaaaaa taaacaaata ggggttccgc gcacatttcc   6060
ccgaaaagtg ccacctgaaa ttgtaaacgt taatattttg ttaaaattcg cgttaaattt   6120
ttgttaaatc agctcatttt ttaaccaata ggccgaaatc ggcaaaatcc cttataaatc   6180
aaaagaatag accgagatag ggttgagtgt tgttccagtt tggaacaaga gtccactatt   6240
aaagaacgtg gactccaacg tcaaagggcg aaaaaccgtc tatcagggcg atggcccact   6300
acgtgaacca tcaccctaat caagttttt gggtcgagg tgccgtaaag cactaaatcg   6360
gaaccctaaa gggagccccc gatttagagc ttgacgggga agccggcga acgtggcgag   6420 aaaggaaggg aagaaagcga aaggagcggg cgctagggcg ctggcaagtg tagcggtcac   6480
gctgcgcgta accaccacac ccgccgcgct taatgcgccg ctacagggcg cgtcccattc   6540
gcca                                                                6544
```

<210> SEQ ID NO 41
<211> LENGTH: 426
<212> TYPE: PRT
<213> ORGANISM: Artificial Sequence
<220> FEATURE:
<223> OTHER INFORMATION: designed protein

<400> SEQUENCE: 41

```
Met Gly Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175
```

-continued

```
Tyr Asp Ile Lys Asp Val Gly Val Asp Asn Ala Gly Ala Lys Ala Gly
            180             185                 190
Leu Thr Phe Leu Val Asp Leu Ile Lys Asn Lys His Met Asn Ala Asp
        195                 200             205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245             250                 255
Lys Pro Phe Val Gly Val Leu Ser Ala Gly Ile Asn Ala Ala Ser Pro
            260             265                 270
Asn Lys Glu Leu Ala Lys Glu Phe Leu Glu Asn Tyr Leu Leu Thr Asp
        275                 280             285
Glu Gly Leu Glu Ala Val Asn Lys Asp Lys Pro Leu Gly Ala Val Ala
    290                 295                 300
Leu Lys Ser Tyr Glu Glu Glu Leu Ala Lys Asp Pro Arg Ile Ala Ala
305             310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
            355                 360                 365
Ser Ser Ser Gly Gly Ser Gly Ser Gly Met Asp Glu Lys Thr Thr Gly
    370                 375                 380
Trp Arg Gly Gly His Val Val Glu Gly Leu Ala Gly Glu Leu Glu Gln
385                 390                 395                 400
Leu Arg Ala Arg Leu Glu His His Pro Gln Gly Gln Arg Glu Pro Gly
                405                 410                 415
Ser Gly His His His His His His Glu Phe
            420             425
```

US 7,138,253 B2

STREPTAVIDIN-BINDING PEPTIDES AND USES THEREOF

CROSS-REFERENCE TO RELATED APPLICATIONS

This application is a divisional of U.S. application Ser. No. 10/004,381, filed Oct. 31, 2001 now U.S. Pat. No. 6,841,359, which claims benefit from U.S. Provisional Application No. 60/244,541, filed Oct. 31, 2000, hereby incorporated by reference.

STATEMENT AS TO FEDERALLY SPONSORED RESEARCH

This invention was funded by grant number R01GM53936 from the National Institutes of Health and grant number NCC-2-1069 from NASA. The government may have certain rights in the invention.

BACKGROUND OF THE INVENTION

In general, the invention features novel compounds and methods for purifying or detecting proteins of interest.

Determining the enzymatic activity, binding specificity, or three-dimensional structure of a protein often requires the purification of the protein from a complex mixture of other components, such as compounds present in a cell lysate or in vitro translation extract. With the number of known proteins increasing dramatically as a result of whole genome sequencing projects, it has become crucial to find alternatives to traditional, time-consuming monoclonal antibody production for generating affinity reagents for the detection and purification of proteins. In addition, purifying a novel protein using traditional column chromatography methods often requires much trial and error to develop a purification protocol that results in the recovery of the protein in high yield and purity.

Thus, purification methods are needed that may be generally applied to proteins of interest, that utilize inexpensive reagents, and that result in highly purified protein without requiring multiple chromatography steps.

SUMMARY OF THE INVENTION

The purpose of the present invention is to provide improved reagents for the purification, detection, or quantitation of proteins of interest. In particular, the high affinity, streptavidin-binding peptides of the present invention may be used as affinity tags for the purification of fusion proteins containing proteins of interest.

Accordingly, in a first aspect, the invention provides a peptide which binds streptavidin with a dissociation constant less than 10 μM (that is, binds streptavidin more tightly than a $K_D$ of 10 μM) and which is not disulfide bonded or cyclized. Preferably, the dissociation constant is equal to or less than 5 μM, 1 μM, 100 nM, 50 nM, 25 nM, 10 nM, or even 5 nM. In one preferred embodiment, the dissociation constant is less than 10 μM, 5 μM, 1 μM, 100 nM, 50 nM, or 25 nM; and greater than 0.01 nM, 0.1 nM, 1 nM, 5 nM, or 10 nM. In another preferred embodiment, the value of the dissociation constant is contained in one of the following ranges: 5 μM to 1 μM, 1 μM to 100 nM, 100 nM to 50 nM, 50 nM to 25 nM, 25 nM to 10 nM, 10 nM to 5 nM, 5 nM to 1 nM, or 5 nM to 0.1 nM, inclusive.

In a related aspect, the invention provides a peptide which binds streptavidin with a dissociation constant less than 10 μM. The amino acid sequence of the peptide does not contain an HPQ, HPM, HPN, or HQP motif. Preferably, the dissociation constant is equal to or less than 5 μM, 1 μM, 100 nM, 50 nM, 25 nM, 10 nM, or 5 nM. In one preferred embodiment, the dissociation constant is less than 10 μM, 5 μM, 1 μM, 100 nM, 50 nM, or 25 nM; and greater than 0.01 nM, 0.1 nM, 1 nM, 5 nM, or 10 nM. In another preferred embodiment, the value of the dissociation constant is contained in one of the following ranges: 5 μM to 1 μM, 1 μM to 100 nM, 100 nM to 50 nM, 50 nM to 25 nM, 25 nM to 10 nM, 10 nM to 5 nM, 5 nM to 1 nM, or 5 nM to 0.1 nM, inclusive.

In another related aspect, the invention provides a peptide which binds streptavidin with a dissociation constant less than 23 nM, 10 nM, or 5 nM. In one preferred embodiment, the peptide is disulfide bonded or cyclized. In another preferred embodiment, the dissociation constant is less than 23 nM, 10 nM, or 5 nM; and greater than 0.01 nM, 0.1 nM, or 1 nM. In another preferred embodiment, the value of the dissociation constant is contained in one of the following ranges: 20 nM to 10 nM, 10 nM to 5 nM, 5 nM to 1 nM, or 5 nM to 0.1 nM, inclusive.

In other related aspects, the invention provides nucleic acids encoding the peptides of the present invention, and vectors that include such nucleic acids.

In addition, standard gene fusion techniques may be used to generate fusion nucleic acids that encode fusion proteins which include a peptide of the present invention and a protein of interest. The fusion proteins may be purified, detected, or quantified based on the high affinity of the peptides for streptavidin.

Accordingly, in one such aspect, the invention provides a fusion protein including a protein of interest covalently linked to one of the following peptides: (a) a peptide which binds streptavidin with a dissociation constant less than 10 μM and which is not disulfide bonded or cyclized, (b) a peptide which binds streptavidin with a dissociation constant less than 10 μM and which does not contain an HPQ, HPM, HPN, or HQP motif, or (c) a peptide which binds streptavidin with a dissociation constant less than 23 nM. In preferred embodiments, the peptide is attached to the amino-terminus or the carboxy-terminus of the protein of interest, or the peptide is positioned between the amino and carboxy-termini of the protein of interest. Preferably, the peptide is linked to the protein of interest by a linker which includes a protease-sensitive site.

In related aspects, the invention provides nucleic acids encoding the fusion proteins of the present invention, and vectors that include these fusion nucleic acids.

In addition, the invention provides a method of producing a fusion protein of the present invention. This method includes transfecting a vector having a nucleic acid sequence encoding the fusion protein into a suitable host cell and culturing the host cell under conditions appropriate for expression of the fusion protein.

The fusion proteins described herein may be used in methods for purifying proteins of interest from samples. Such a method involves expressing the protein of interest as a fusion protein covalently linked to one of the following peptides: (a) a peptide which binds streptavidin with a dissociation constant less than 10 μM and which is not disulfide bonded or cyclized, (b) a peptide which binds streptavidin with a dissociation constant less than 10 μM and which does not contain an HPQ, HPM, HPN, or HQP motif, or (c) a peptide which binds streptavidin with a dissociation constant less than 23 nM. A sample containing the fusion protein is contacted with streptavidin under conditions that allow complex formation between the fusion protein and streptavidin. The complex is isolated, and the fusion protein is recovered from the complex, thereby purifying the protein of interest from the sample. In one preferred embodiment, the protein of interest is recovered from the fusion protein by cleaving the streptavidin-binding peptide from the fusion protein.

In yet another aspect, the invention provides a method of detecting the presence of a fusion protein of the present invention in a sample. This method includes (a) contacting the sample with streptavidin or a streptavidin-containing compound under conditions that allow complex formation between the fusion protein and either streptavidin or the streptavidin-containing compound; (b) isolating the complex, and (c) detecting the presence of streptavidin or the streptavidin-containing compound in the complex or following recovery from the complex. The presence of streptavidin or the streptavidin-containing compound indicates the presence of the fusion protein in the sample. Preferably, step (c) also involves measuring the amount of streptavidin or the streptavidin-containing compound in the complex or following recovery from the complex. The amount of fusion protein in the sample is correlated with, and may be calculated from, the measured amount of streptavidin. For example, for a fusion protein containing a peptide that binds one molecule of streptavidin per molecule of peptide, the amount of fusion protein in the sample is predicted to be approximately the same as the amount of streptavidin measured. In one preferred embodiment, the amount of streptavidin is determined using Western or ELISA analysis with an antibody that reacts with streptavidin or that reacts with a compound that is covalently linked to streptavidin. In another preferred embodiment, streptavidin is covalently linked to an enzyme, radiolabel, fluorescent label, or other detectable group, and the amount of streptavidin is determined using standard techniques based on a characteristic of the detectable group such as its enzyme activity, radioactivity, or fluorescence.

In another aspect, the invention features a method of determining the affinity of a compound of interest for a target molecule. The method includes incubating a solution having a compound of interest with a detectable group and a free target molecule under conditions that allow complex formation between the compound of interest and the free target molecule. The solution is contacted with a target molecule immobilized on a solid support under conditions that allow complex formation between the compound of interest and the immobilized target molecule, and the compound of interest bound to the immobilized target molecule is then separated from the compound of interest not bound to the immobilized target molecule. To determine the affinity, either the amount of the compound of interest that is bound to the immobilized target or the amount of the compound of interest not bound to the target molecule is then measured. In yet another preferred embodiment, the steps of this method are repeated one or more times with a different concentration of free target molecule. In other preferred embodiments, both the amount of the compound of interest bound to the immobilized target molecule and the amount of the compound of interest not bound to the immobilized target molecule are measured. In another embodiment, only the amount of the compound of interest that is not bound to the immobilized target molecule is measured. In another embodiment, the target is immobilized on a solid support such as a microtiter plate, a bead, or the matrix of a spin-filter column. In another embodiment, the compound of interest that is bound to the immobilized target molecule is separated from the coumpound of interest that is not bound to the immobilized target molecule by centrifugation, for example, by spin-filtration or ultracentrifugation. In still other preferred embodiments, the target is a small molecule such as streptavidin, a streptavidin fusion protein, streptavidin covalently bound to an enzyme (e.g. horseradish peroxidase or alkaline phosphatase), or a ligand. The compound of interest may be a peptide that binds streptavidin, or may be a fusion protein that includes a peptide that binds streptavidin and a protein of interest. In other embodiments, the compound of interest may be labeled with a detectable group, such as a radiolabel, a fluorescent molecule, or an enzyme.

In preferred embodiments of various aspects of the invention, the amino acid sequence of the peptide includes at least 10, 25, 50, 75, or 100 consecutive amino acids or consists of between 5 and 150, 10 and 100, 20 and 75, or 30 and 50 amino acids, inclusive, of any one of SEQ ID Nos. 1–29 or 35. Preferably, the amino acid sequence of the peptides includes an LPQ, QPQ, EPQ, HPA, HPD, or HPL motif. In other preferred embodiments, the amino acid sequence includes any one of SEQ ID Nos. 1–29 or 35. In still other preferred embodiments, the peptide has an amino acid sequence that is at least 20, 30, 40, 50, 60, 70, 80, 90, 95, or 100% identical to any one of SEQ ID Nos. 1–29 or 35.

It is also contemplated that the affinity of the peptides of the present invention for streptavidin may be increased by incorporating disulfide bonds into, or cyclizing, the peptides. By constraining the peptides, the amount of disorder inherent in the peptides (i.e., entropy) decreases, and thus binding of these peptides to streptavidin may require less energy. It is also contemplated that the three-dimensional structure of peptides of the invention bound to streptavidin may be experimentally determined or modeled based on the known crystal structure of streptavidin and used to determine possible modifications to the peptides that may further improve their affinity for streptavidin.

As used herein, by "nucleic acid" is meant a sequence of two or more covalently bonded naturally-occurring or modified deoxyribonucleotides or ribonucleotides.

By "peptide" is meant a sequence of two or more covalently bonded naturally-occurring or modified amino acids. The terms "peptide" and "protein" are used interchangeably herein.

By "covalently linked" is meant covalently bonded or connected through a series of covalent bonds. A group that is covalently linked to a protein may be attached to the amino-terminus, carboxy-terminus, between the amino- and carboxy-termini, or to a side chain of an amino acid in the protein.

By "streptavidin" is meant any streptavidin molecule or fragment thereof or any protein that has an amino acid sequence that is at least 80, 90, 95, or 100% identical to a streptavidin molecule or fragment thereof (see, for example, Haeuptle et al. J. Biol. Chem. 258: 305, 1983). A preferred fragment of streptavidin is "core" streptavidin, which is a proteolytic cleavage product of streptavidin (Bayer et al. Biochem. J. 259,369–376, 1989). Preferably, a streptavidin molecule or fragment thereof is capable of binding biotin or any other streptavidin-binding molecule. Streptavidin or a streptavidin fragment may be modified chemically or through gene fusion technology or protein synthesis so that it is covalently linked to an enzyme, radiolabel, fluorescent label, or other detectable group. These detectable groups may be used to determine the presence or location of a streptavidin-bound fusion protein in a cell or sample or to quantify the amount of a streptavidin-bound fusion protein, using standard methods.

By a "streptavidin-containing compound" is meant any compound that includes streptavidin covalently bound to another molecule. These compounds may, for example, be conjugated to streptavidin through gene fusion technology or protein synthesis and may, for example, be covalently linked to an enzyme, such as horseradish peroxidase or alkaline phosphatase, a fluorescent group, a radiolabel, or any other detectable group.

By "free target molecule" is meant a target molecule that is not bound to a solid support.

By "cyclized" is meant nonlinear. A peptide may be cyclized by the formation of a covalent bond between the N-terminal amino group of the peptide or the side-chain of a residue and the C-terminal carboxyl group or the side-chain of a residue. For example, a peptide lactam may be formed by the cyclization between the N-terminal amino group or an amino group of an amino acid side-chain and the C-terminal carboxyl group or a carboxyl or amide containing side-chain. Other possible cyclizations include the formation of a thioether by the reaction of a thiol group in a cysteine side-chain with the N-terminal amino group, C-terminal carboxyl group, or the side-chain of another amino acid. A disulfide bond may also be formed between two cysteine residues. As used herein, a "non-cyclized peptide" is a linear peptide that does not have any of the above cyclizations.

By "dissociation constant" is meant the dissociation constant for binding streptavidin as measured using the electrophoretic mobility shift assay described herein. By "less than" a particular dissociation constant is meant capable of binding streptavidin more tightly than the strength of binding represented by a particular dissociation constant.

By "purifying" is meant separating a compound, for example, a protein, from other components that naturally accompany it. Typically, a protein is substantially pure when it is at least 50%, by weight, free from proteins and naturally-occurring organic molecules with which it is naturally associated. Preferably, the protein is at least 75%, more preferably, at least 90%, and most preferably, at least 99%, by weight, pure. In other preferred embodiments, the protein is at least 2, 5, 10, 25, 50, or 100 times as pure as the starting material. Purity may be assayed by any appropriate method, such as polyacrylamide gel electrophoresis, column chromatography, optical density, HPLC analysis, western analysis, or ELISA (see, for example, Ausubel et al., Current Protocols in Molecular Biology, John Wiley & Sons, New York, 2000).

By "recovered from the complex" is meant physically separated from the complex of streptavidin and the fusion protein. For example the streptavidin-bound fusion protein may be incubated under conditions that reduce the affinity of the fusion protein for streptavidin (i.e., at low or high salt concentrations or at low or high pH values) or incubated in the presence of molecules that compete with the fusion protein for binding streptavidin. Preferably, either the fusion protein or the streptavidin that has been released from the complex is isolated using standard procedures, such as column chromatography, polyacrylamide gel electrophoresis, HPLC, or western analysis.

The present invention provides a number of advantages related to the detection and purification of proteins of interest. For example, because the present methods do not require the generation of an antibody or other affinity reagent that is specific for each protein of interest, these methods may be universally applied to any protein. In addition, if desired, the streptavidin-binding peptide may be connected to the protein of interest through a protease cleavable linker, allowing removal of the peptide after purification of the fusion protein.

Using the methods described herein, purification of a fusion protein based on its affinity for streptavidin has allowed the isolation of the fusion protein in significantly higher purity than that obtained using a hexahistidine affinity tag or maltose-binding protein affinity tag. Moreover, streptavidin is an inexpensive reagent that may be purchased unmodified or covalently labeled with a detectable group (such as FITC-streptavidin or alkaline phosphatase-conjugated streptavidin) or with a chromatography matrix (such as streptavidin-agarose). The availability of these reagents simplifies methods for detecting and purifying the fusion proteins of the present invention.

In addition, the streptavidin binding peptide-tag are particularly useful when intermediate amounts of protein (~10–500 µg) need to be produced and purified in a high throughput manner. For example, highly parallel purification protocols may be performed in 96-well plates using streptavidin-derivatized magnetic beads and streptavidin binding peptide-tagged proteins expressed in E. coli or in coupled in vitro transcription/translation reactions. This facilitates purification, for example, for proteomics applications in which thousands of purified proteins need to be generated and purified in parallel.

Other features and advantages of the invention will be apparent from the following detailed description and from the claims.

BRIEF DESCRIPTION OF THE DRAWINGS

FIG. 8A is an illustration of an mRNA display template terminating in puromycin in which the tobacco mosaic virus translation enhancer sequence (TMV), the initiating methionine codon (AUG), and the sections of the open reading frame encoding the two protein affinity tags (FLAG and $His_6$) are labeled. FIG. 8B is an illustration of an mRNA display template that is free of frameshifts and premature stop codons and thus encodes a full-length protein containing both affinity tags. FIG. 8C illustrates an mRNA display template that has initiated internally and displays the corresponding truncated protein lacking the N-terminal FLAG tag. FIG. 8D shows an mRNA display template that has a deletion in its open reading frame and thus displays the corresponding frameshifted protein lacking the C-terminal $His_6$ tag. FIG. 8E illustrates the reverse transcription of the mRNA display template from FIG. 8B that was purified based on the presence of both protein affinity tags in the encoded protein. FIG. 8F shows the cleavage sites for Type IIS restriction enzymes which are encoded in each cassette. Ligation of pre-selected cassettes which have been cleaved with these enzymes yields the full-length DNA library.

DETAILED DESCRIPTION

The present methods stem from the discovery of peptides that have unusually high affinities for streptavidin ($K_D$ of less than 10 µM). These peptides were selected from a library of randomized, non-constrained peptides using the mRNA display method. The high affinity of the selected peptides was particularly surprising, given the fact that non-constrained linear peptide libraries generally do not yield high affinity ligands to proteins, except in cases where the protein normally functions in peptide recognition (Clackton et al., Trends Biotech 12:173–184 (1994); Katz, Annu. Rev. Biophys. Biomol. Struct. 26:27–45, 1997). Many other peptides with high affinity for streptavidin may be isolated using the mRNA display method or any other selection method, such as ribosome display (Roberts, Curr. Opin. Chem. Biol. 3(3):268–73, 1999), or phage display (U.S. Pat. No. 5,821,047).

Figure 1:
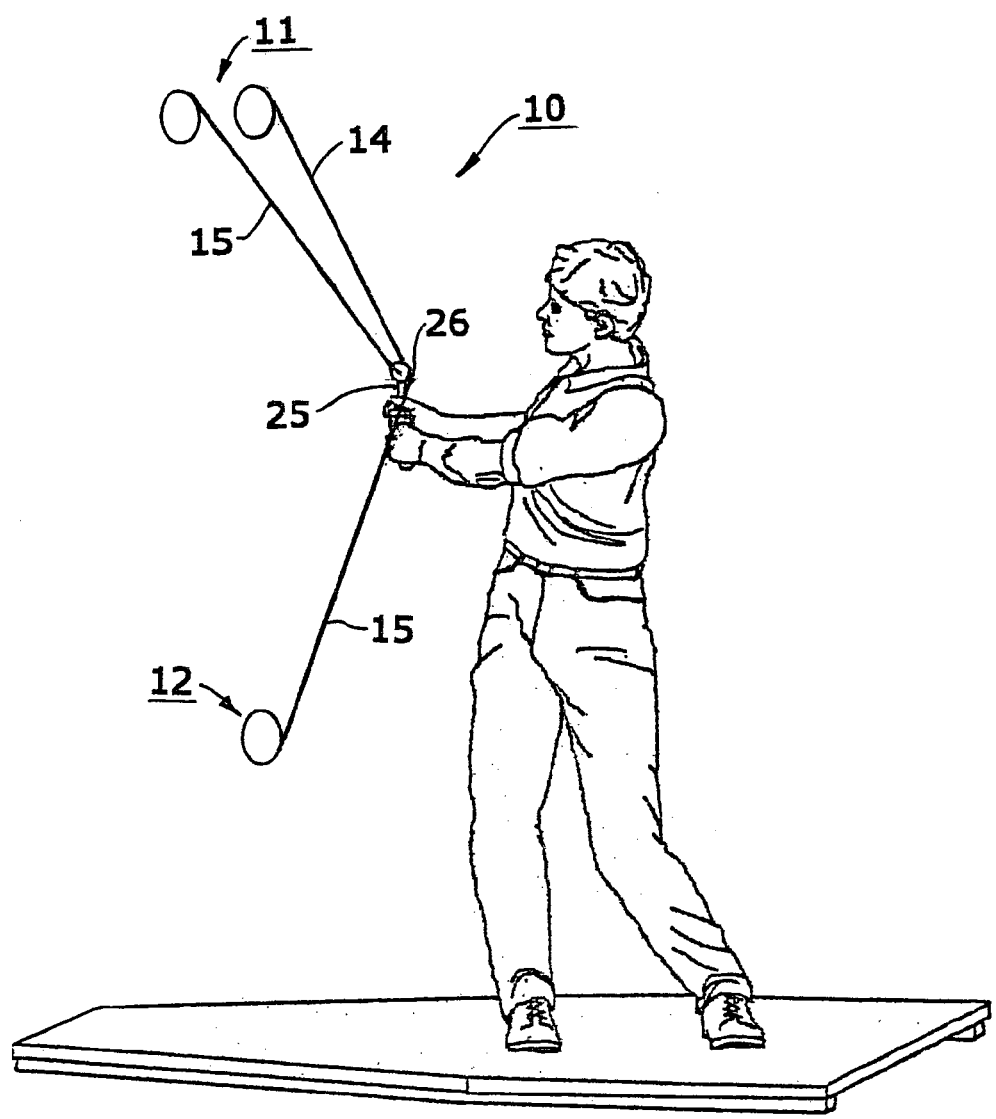
FIG. 1A is a schematic illustration of an in vitro selection process according to the invention, showing the structure of the library and the selection scheme. Members of the DNA library have, from the 5' to 3' end, a T7 RNA polymerase promoter (T7), a tobacco mosaic virus translation enhancer (TMV), a start codon (ATG), 88 random amino acids, a hexahistidine tag (H6), and a 3' constant region (Const).
FIG. 1B is a picture of an SDS-PAGE gel of samples from the library at different stages of preparation. The first lane shows the result of translating the mRNA display template with $^{35}$S-methionine. Most of the counts represent free peptide (free pep), but a significant amount of mRNA-peptide covalent fusions are also present (mRNA-pep). There is also another band that is independent of added template (NS, non-specific), and some counts remain in the gel well. The band corresponding to the mRNA-peptide can be shifted to a position slightly higher than that for the free peptide by the addition of RNase A. The remaining lanes show the result of successive oligo-dT and Ni-NTA purifications, and finally reverse transcription (RT).
Figure 2:
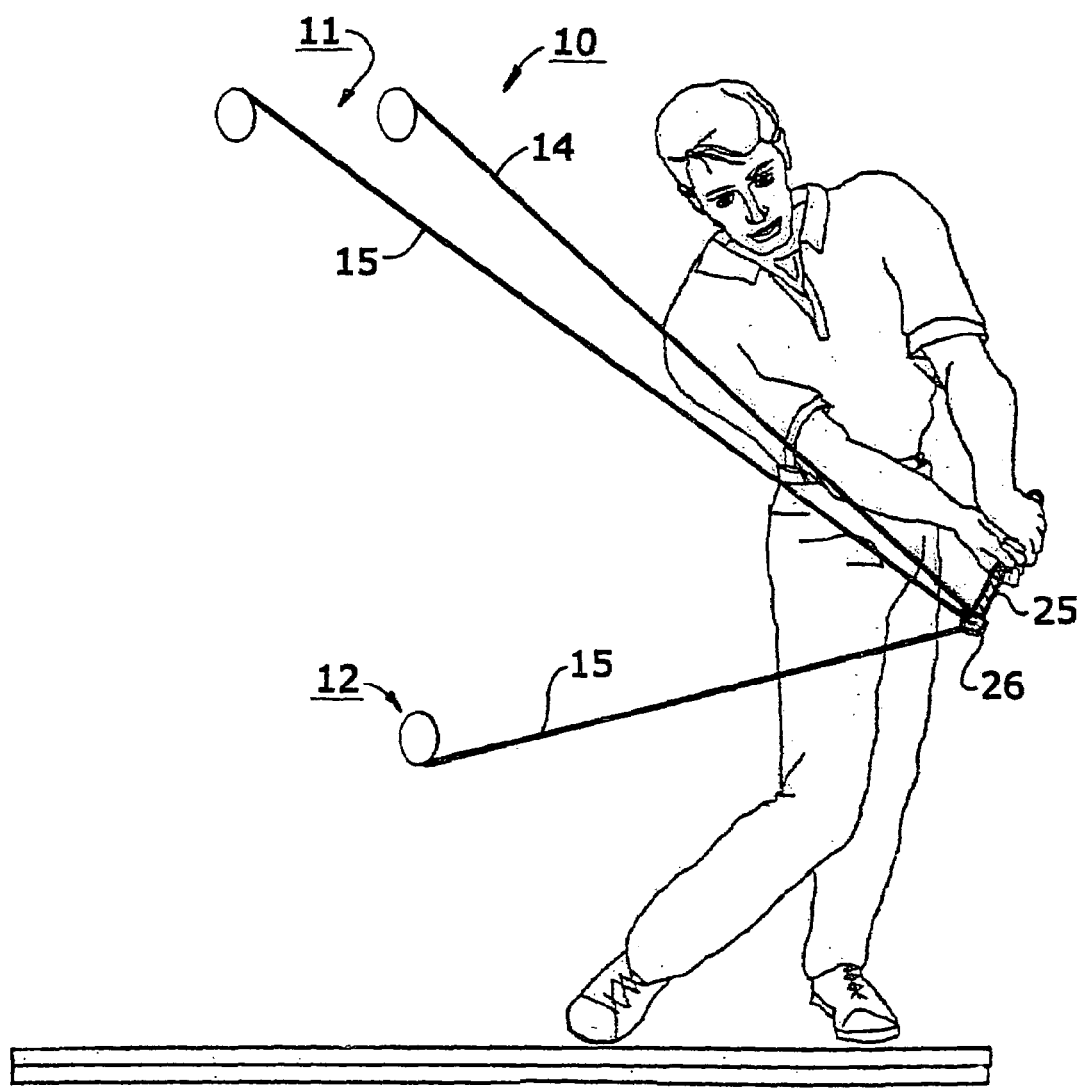
FIG. 2A is a bar graph showing the fraction of $^{35}$S counts from the displayed peptides that bound to streptavidin and eluted with biotin, at each round of selection.
FIG. 2B is a graph showing the elution profile for the peptide library generated from the output of the seventh round of selection in FIG. 2A. The first fraction represents the flow-through. Biotin was added at the point indicated. The plot compares the binding of the intact, reverse-transcribed, displayed peptides (mRNA-pep), the same sample treated with RNase A, and the RNase-treated sample applied to a streptavidin column pre-saturated with biotin (excess biotin was washed away prior to exposing the library to the matrix).
Figure 3:
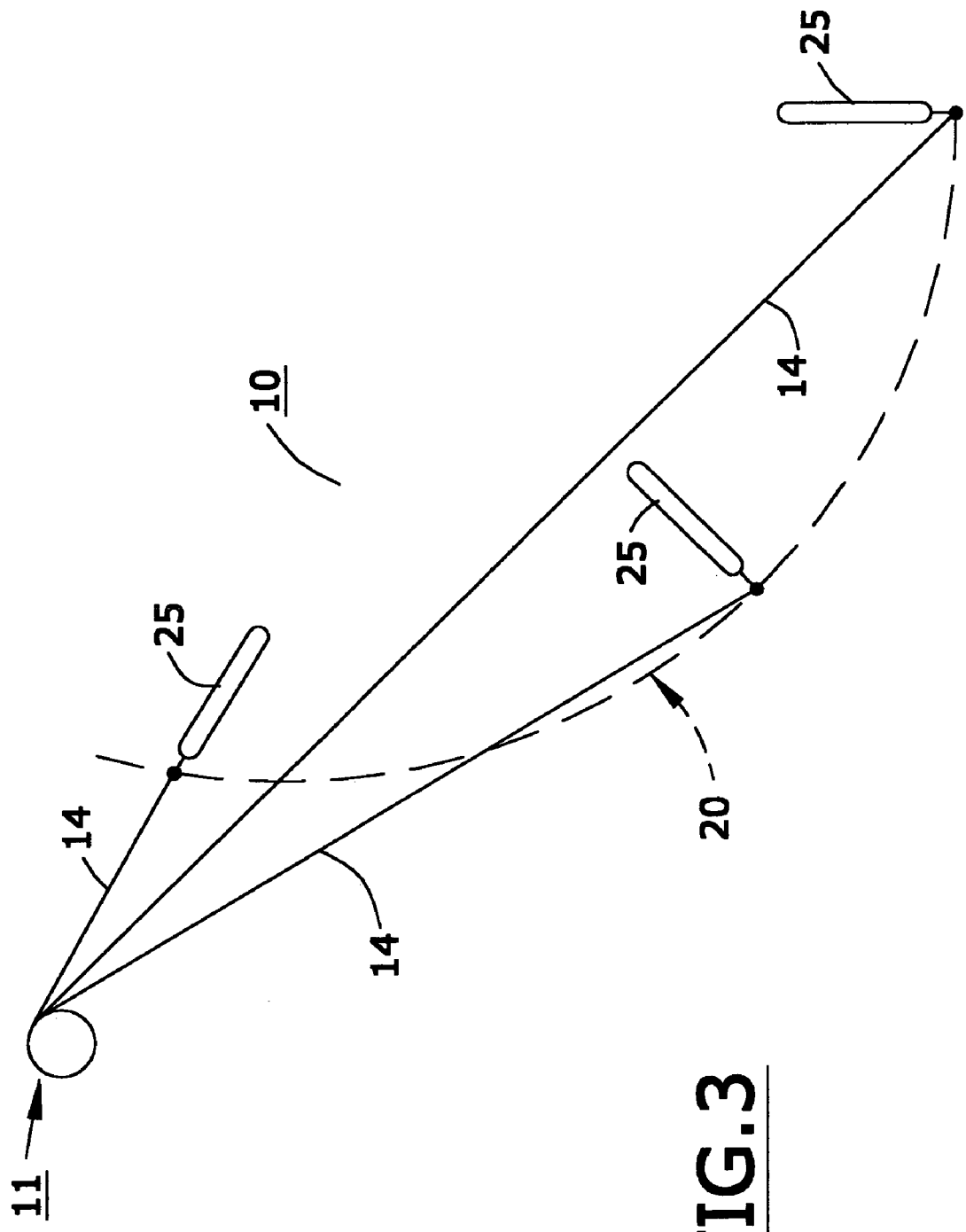
FIG. 3 is a list of the sequences of 20 clones from the seventh round of selection (SEQ ID Nos.: 1–20). The "#" column indicates the number of times each sequence was observed. The HPQ sequence is in bold type. Non-random sequences at the termini are underlined. The six C-terminal-most residues are not shown.
Figure 4:
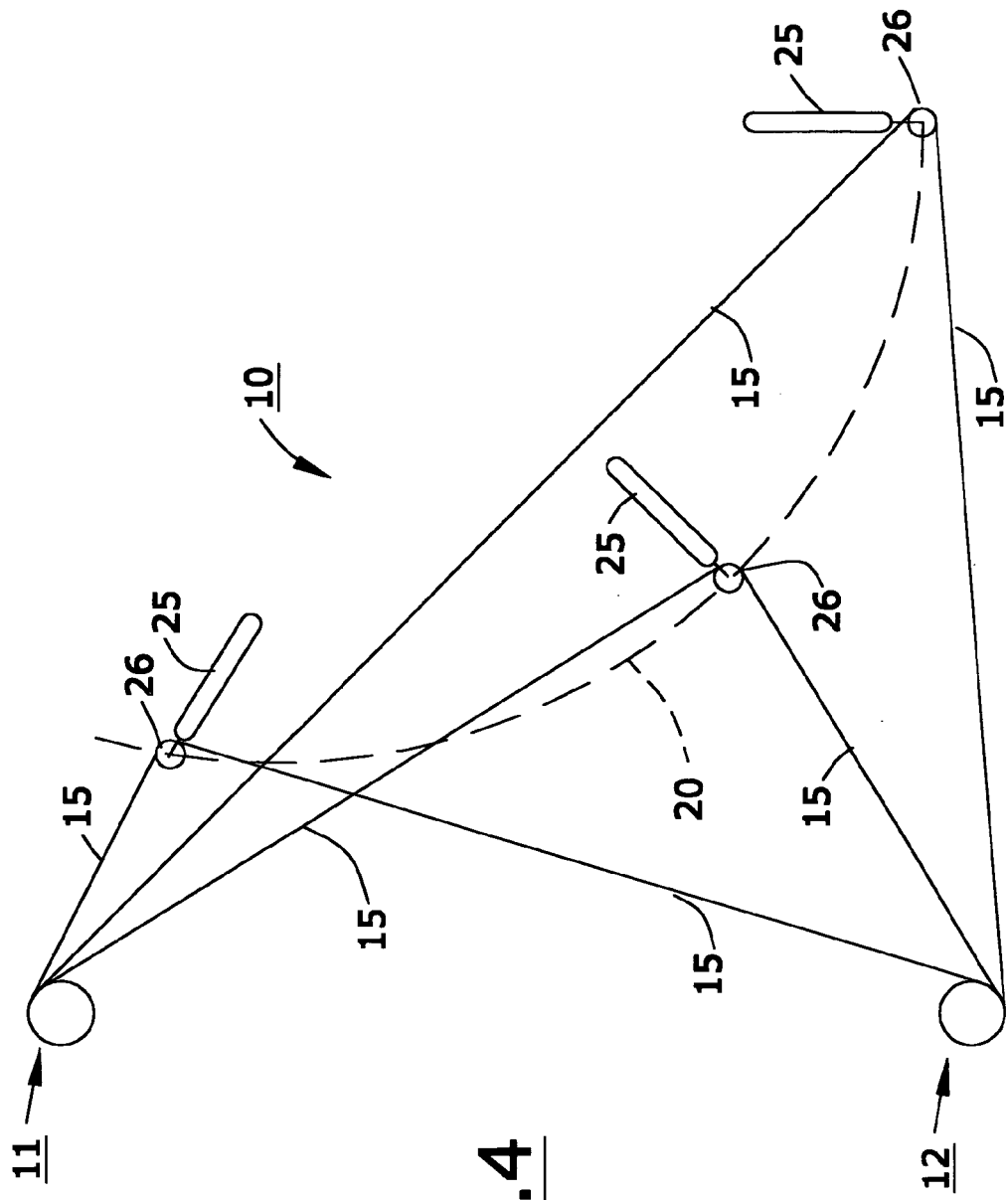
FIG. 4A is a picture of a native gel showing an electrophoretic mobility shift (EMSA) analysis demonstrating the binding of four different DNA-tagged peptides to streptavidin. The migration of each clone is shown in the absence (−) and presence (+) of 1 µM streptavidin. Some of the clones show multiple bands, presumably representing different conformations. The arrows show the position of the gel well, which often contains a fraction of the counts.
FIG. 4B is a picture of a native gel showing the titration of the full-length clone SB19 with streptavidin. The streptavidin concentration in each lane, from left to right, is: 3.8, 6.6, 10, 15, 23, 35, and 61 nM.
FIG. 4C is a curve fit of the data shown in FIG. 4B (the fraction of peptide bound could not be accurately determined for the point with the lowest concentration of streptavidin). Assuming that the peptide is homogeneous and 100% active, the data from this experiment give a $K_D$ of 10 nM for the binding of peptide SB19 to streptavidin.

The binding characteristics of exemplary selected streptavidin-binding peptides are described in Table 1, and the sequences of these peptides are listed in FIG. 3. The first column of Table 1 lists the peptide name (SB1-SB20). For comparison, a non-selected sequence with two HPQ motifs spaced by 19 residues (called "non-selected") is listed in row one. SB19-C4 is a truncation mutant of peptide SB19, described below. The peptides are grouped according to the number of HPQ and similar tripeptide motifs they possess. The second column shows the number of tripeptide motifs in each peptide, and the number of amino acid residues separating them. The third column represents the percentage of peptide binding and specifically eluting from a streptavidin column. This percentage ranged from 8.3% to as high as 88% for the selected peptides, compared to only 0.16% for the control, non-selected peptide with two HPQ motifs.

The fourth column shows the $K_D$, when known, for the interaction between streptavidin and the peptides, as measured in the EMSA assay described herein. The standard deviation in the $K_D$ is shown in the fifth column, based on the number of independent measurements (n, shown in parentheses). The dissociation constant ranged from 110 nM for peptide SB5 to 4.8 nM for peptides SB2.

TABLE 1

| Peptide | Structure | % binding and eluting | $K_D$ (nM) | Standard deviation (n) |
|---|---|---|---|---|
| Non-selected | HPQ 19 HPQ | 0.16 | | |
| *Two HPQ motifs* | | | | |
| SB1 | HPQ 19 HPQ | 86 | 50 | 5.7 (4) |
| SB2 | HPQ 19 HPQ | 48 | 4.8 | 0.91 (8) |
| SB3 | HPQ 23 HPQ | 20 | | |
| SB4 | HPQ 43 HPQ | 49 | | |
| SB5 | HPQ 52 HPQ | 72 | 110 | 22 (6) |
| *One HPQ and one similar tripeptide motif* | | | | |
| SB6 | HPL 4 HPQ | 49 | | |
| SB7 | HPD 7 HPQ | 28 | | |
| SB8 | HPQ 12 HPL | 27 | | |
| SB9 | HPQ 12 HP | 64 | | |
| SB10 | HPQ 21 QPQ | 15 | | |
| SB11 | HPQ 28 HPA | 68 | | |
| SB12 | HPQ 30 EPQ | 73 | | |
| SB13 | HPQ 32 EPQ | 64 | | |
| SB14 | HPQ 43 HPL | 11 | | |
| SB15 | QPQ 50 HPQ | 44 | 92 | 16 (4) |
| SB16 | HPQ 74 LPQ | 50 | | |

TABLE 1-continued

| Peptide | Structure | % binding and eluting | $K_D$ (nM) | Standard deviation (n) |
|---|---|---|---|---|
| *One HPQ motif* | | | | |
| SB17 | | 8.3 | | |
| SB18 | | 58 | | |
| SB19 | | 85 | 10 | 1.8 (10) |
| SB19 - C4 | | 88 | 4.9 | 0.88 (10) |
| *No HPQ motif* | | | | |
| SB20 | HPL | 34 | | |

Figure 5A:
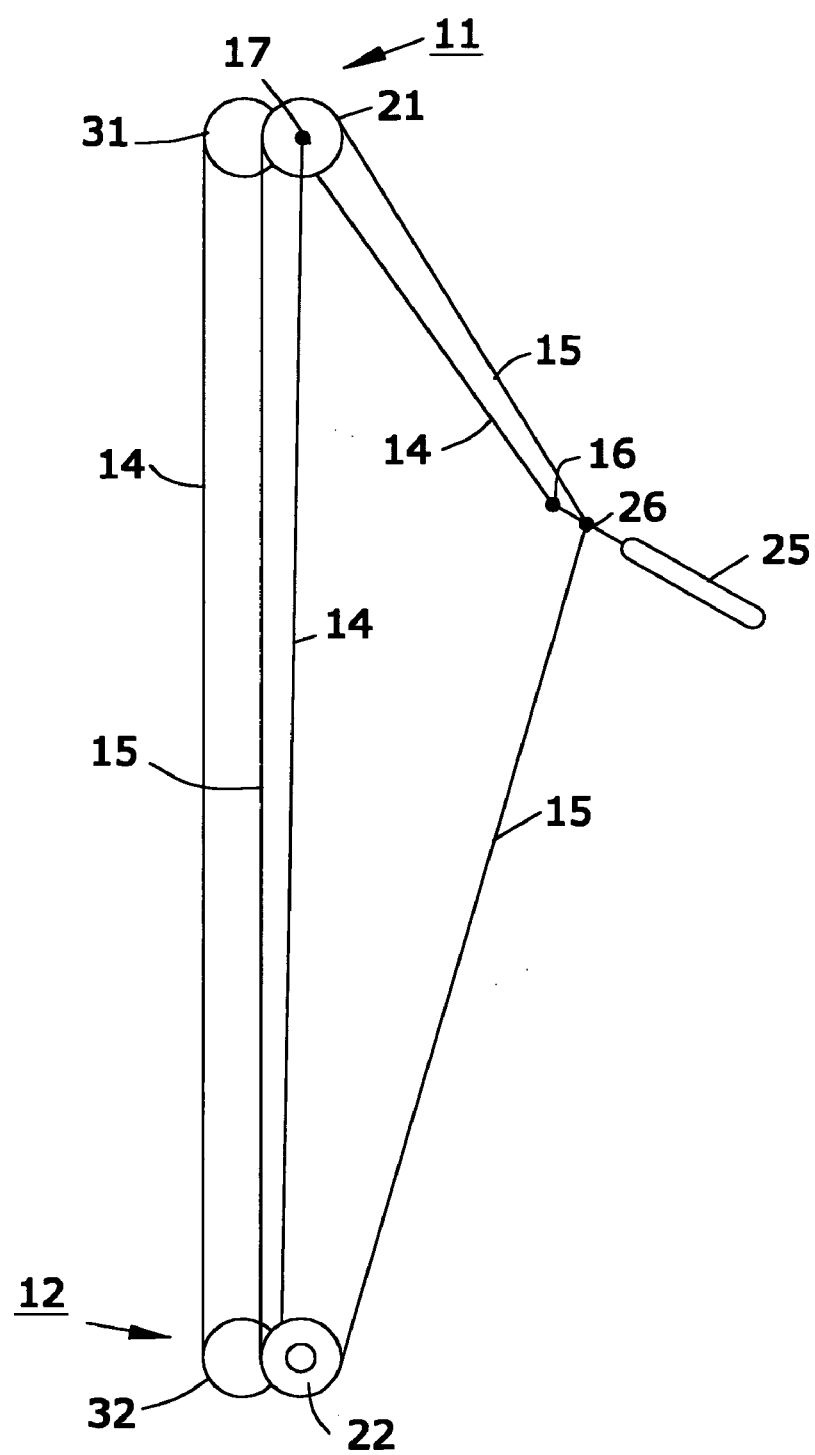
FIG. 5 is a list of the sequences of truncation mutants of peptide SB19 (SEQ ID Nos.: 21–29). The full-length (FL), C-terminal deleted (C1–C4), N-terminal deleted (N1–N3), and point mutated (M1) peptide sequences are shown. The "% binding" refers to the performance of these peptides in the streptavidin column-binding assay.
Figure 5B:
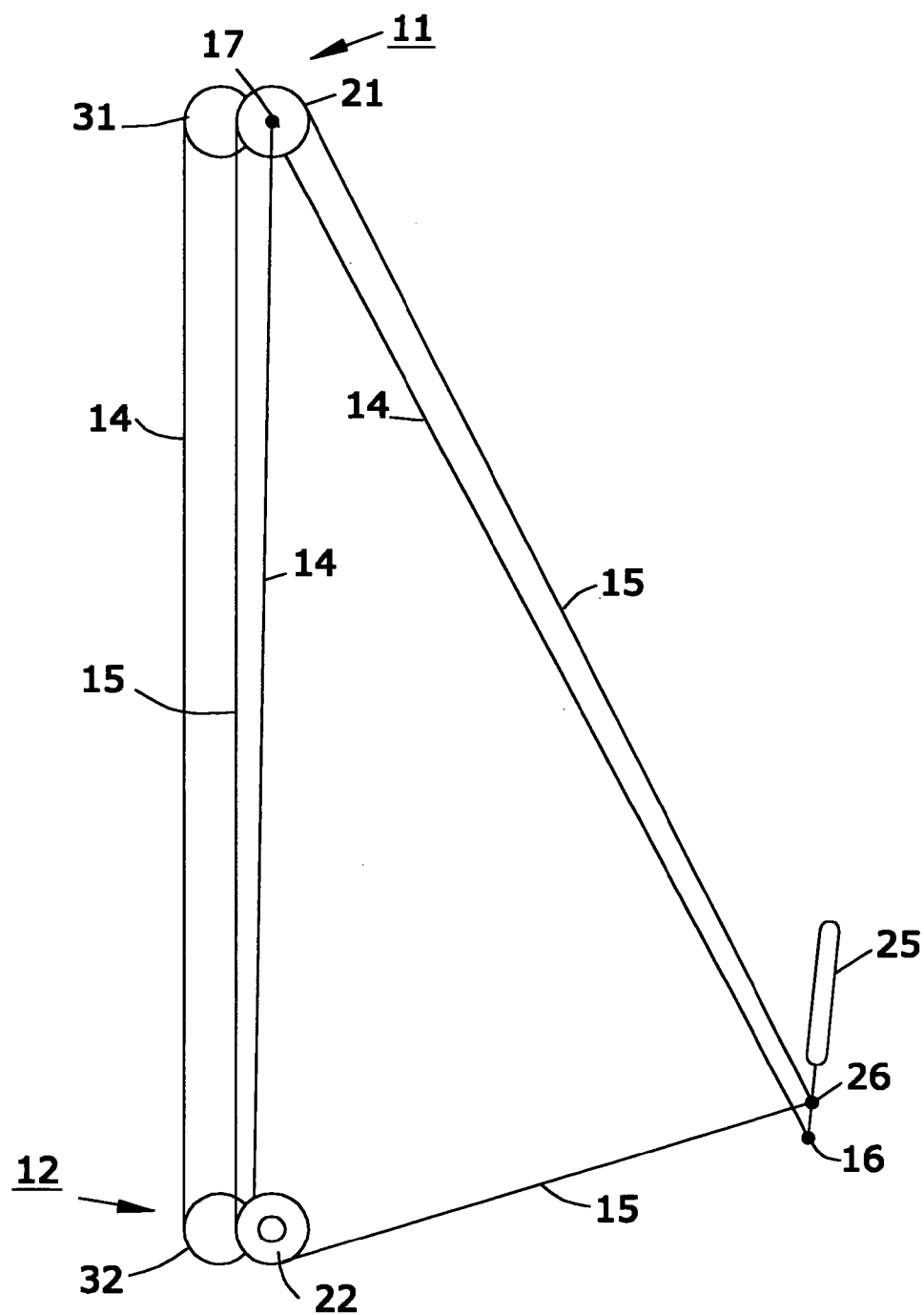

To further characterize the binding of the selected peptides to streptavidin, truncation mutants for peptide SB19 were constructed to determine which regions were necessary for high affinity streptavidin-binding (FIG. 5). Deletion of up to 56 residues had no observable effect on the binding strength. For example, peptide SB19-C4 retained only the first 38 residues from the selected construct (plus the C-terminal sequence MMSGGCKLG, SEQ ID No.: 36) and had a dissociation constant of 4.9 nM for streptavidin (Table 1). In contrast, N-terminal truncation mutations (N1–N3) resulted in a lower percentage of the encoded peptide specifically eluting from the streptavidin column (0.058 to 69% for the truncation mutants compared to 85% for full length SB19). These results suggested that the determinants for binding streptavidin were spread throughout the N-terminal 38 residues of the SB19 peptide.

High affinity streptavidin-binding peptides, such as those shown in Table 1, have a number of uses. For example, these peptides may be used for protein purification by expressing a protein of interest as a fusion protein joined to one or more of the streptavidin-binding peptides of the invention. In one such purification method, a sample containing the fusion protein is incubated with immobilized streptavidin. Proteins with no or weak affinity for streptavidin are washed away, and the fusion protein is then selectively eluted from the streptavidin matrix by addition of biotin, a biotin analog, another streptavidin-binding peptide, or any compound that competes with the fusion protein for binding to the matrix. Alternatively, the fusion protein may be eluted from the matrix by increasing or decreasing the pH of the buffer applied to the matrix.

As described in detail below, this general protocol was used in a one-step purification of a fusion protein containing a streptavidin-binding peptide from an *E. coli* extract, resulting in a high yield of very pure protein. This fusion protein contained the first 38 amino acids of the SB19-C4 peptide, which due to its small size was not expected to affect the three-dimensional structure or activity of the covalently-linked protein of interest. Purification of fusion proteins containing other streptavidin-binding peptides of the present invention may be performed similarly.

In addition, various modifications of the above purification protocol would be apparent to one skilled in the art (see, for example, Ausubel et al., supra), and such modifications are included in the invention. In particular, use of the streptavidin-binding peptides as affinity tags is desirable for high throughput protein production and purification. For example, purification of fusion proteins in a multi-well format may be conducted using magnetic streptavidin beads that are washed and eluted robotically. The methods of the present invention may also be adapted to purify fusion proteins from in vitro translation mixtures or from other extracts, such as those from prokaryotic, yeast, insect, or mammalian cells, using standard techniques. If necessary, avidin may be added to the extract to bind any free biotin in the extract before contacting a sample from the extract with streptavidin. Allowing any free biotin to bind avidin may prevent biotin from competing with the streptavidin-binding peptides for binding to streptavidin.

If desired, the presence of a fusion protein of the invention in a sample may be detected by incubating the fusion protein with streptavidin.(i.e., unlabeled streptavidin or streptavidin that is labeled with a detectable group) under conditions that allow streptavidin to bind the fusion protein. Preferably, the unbound streptavidin is separated from the streptavidin-bound fusion protein. Then, the streptavidin that is bound to the fusion protein is detected. Alternatively, the streptavidin bound to the fusion protein is physically separated from the fusion protein and then detected, using standard methods. For example, to detect streptavidin that is bound to the fusion protein or that has been separated from the fusion protein, Western or ELISA analysis may be performed using an antibody that reacts with streptavidin or that reacts with a compound that is covalently linked to streptavidin. If streptavidin is covalently linked to an enzyme, radiolabel, fluorescent label, or other detectable group, the amount of streptavidin may be determined using standard techniques based on a characteristic of the detectable group such as its enzyme activity, radioactivity, or fluorescence (see, for example, Ausubel et al., supra). Alternatively, streptavidin may be contacted with a streptavidin-binding compound that is covalently linked to an enzyme, radiolabel, fluorescent label, or other detectable group, and the detectable group may be assayed as described herein.

We have also developed an improved method to generate synthetic DNA libraries encoding full-length proteins, which may be used in a variety of selection methods to isolate proteins with desired binding affinities or activities. The generation of libraries of proteins containing a desired number of amino acids is often limited by the number of internal initiation events that result in truncated proteins and the number of frameshifts that result in either premature stop codons or the removal of desired stop codons. For example, during solid phase DNA synthesis, insertions and deletions which cause frameshifts may occur due to imperfect coupling and capping efficiencies. In addition, the random regions in DNA templates may encode stop codons, resulting in premature truncation of the encoded protein. To address these problems, we have developed a method in which small DNA cassettes are synthesized, and an in vitro selection using the mRNA display technology is performed to enrich the library of DNA cassettes for sequences encoding two protein affinity tags. These DNA cassettes lack frameshifts and premature stop codons. The selected DNA cassettes are then cleaved with restriction enzymes and ligated to generate the full-length DNA library (FIGS. 8A–8F) (Cho et al., J. Mol. Biol. 297:309–319, 2000).

Figure 8:
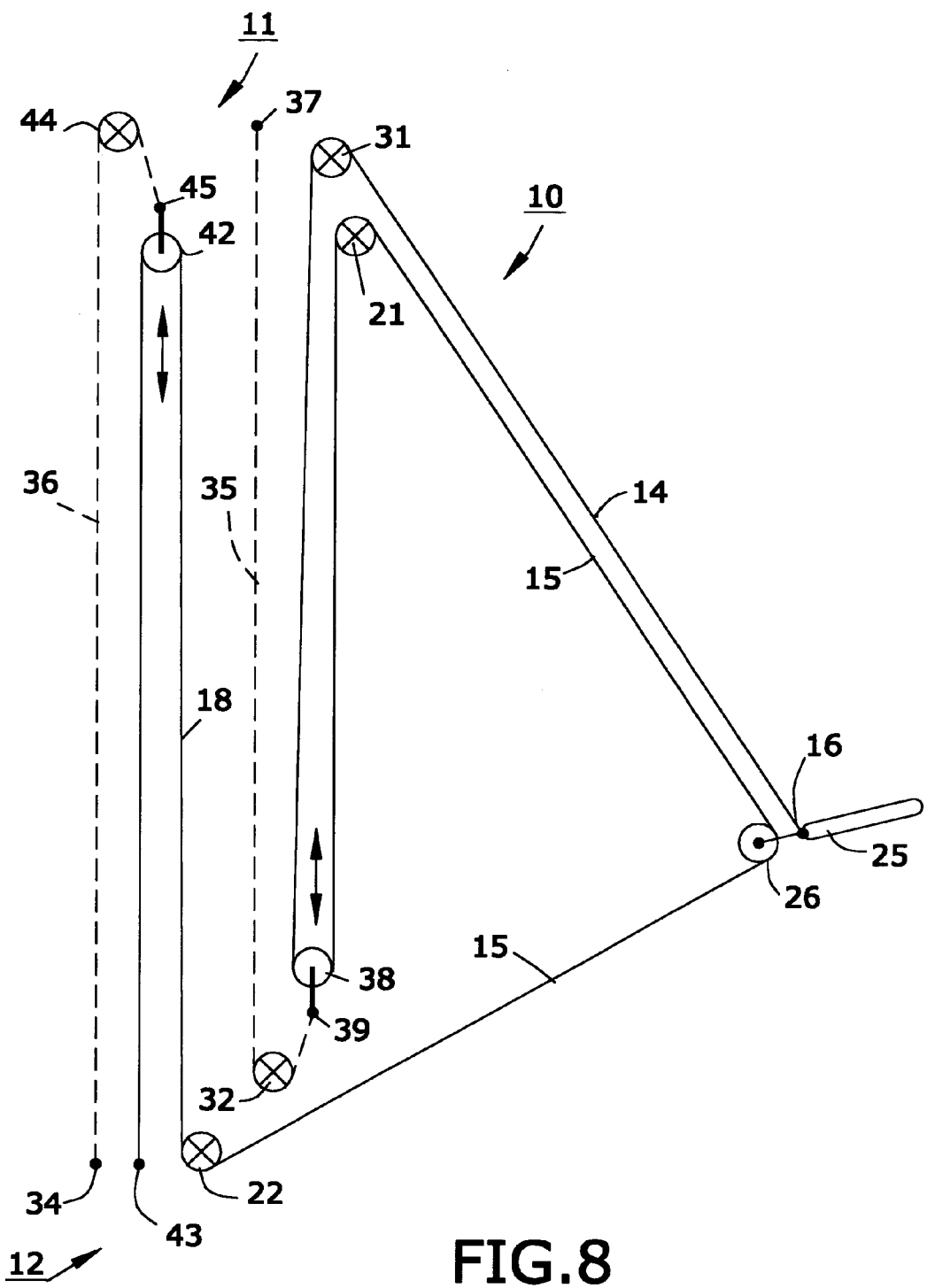
FIGS. 8A–8F are schematic illustrations of the pre-selection method.

In one preferred embodiment of this method, mRNA display templates that contain a translation enhancer sequence operably-linked to an open reading frame and that terminate in puromycin are generated as described previously (Cho et al., supra). The open reading frame encodes two different protein affinity tags, such as a FLAG tag and a hexahistidine tag. Preferably, one of the tags is located at the amino-terminus of the encoded peptide, and the other tag is located at the carboxy-terminus. The mRNA display templates are in vitro translated to generate mRNA displayed peptides (Cho et al., supra). mRNA displayed peptides encoded by templates that do not contain frameshifts or premature stop codons should contain both affinity tags. In contrast, templates that contain frameshifts or premature stop codons encode peptides without the C-terminal affinity tag (FIG. 8D). Additionally, mRNA display templates that initiate internally produce peptides without the N-terminal affinity tag (FIG. 8C). The library of mRNA displayed peptides is enriched for peptides containing both affinity tags by purification of the mRNA displayed peptides based on the presence of these tags (see, for example, Ausubel et al., supra). For example, the mRNA displayed peptides may be applied to a matrix designed to bind peptides containing one of the affinity tags, and the mRNA display peptides without the affinity tag are washed away. The mRNA display peptides containing the affinity tag are then eluted and applied to a second matrix designed to bind the other affinity tag. The mRNA display peptides recovered from this purification step are enriched for members containing both affinity tags and thus for full-length peptides. These mRNA displayed peptides are reversed transcribed to generate double-stranded DNA. The amplified DNA is then cleaved by restriction enzymes. Preferably, this restriction digestion removes the sequences encoding the affinity tags from the DNA cassettes. The cleaved DNA cassettes are then ligated to generate the full-length DNA templates.

The experiments described above were carried out as follows.

Generation of a Streptavidin-Binding Peptide Library

The mRNA display method for selecting peptides or proteins of interest takes advantage of the translation-terminating antibiotic puromycin, which functions by entering the A site of ribosomes and forming a covalent bond with the nascent peptide. By covalently attaching puromycin to the 3' end of an mRNA, a covalent link between a polypeptide and its encoding message can be achieved in situ during in vitro translation (Roberts et al., Curr. Opin. Struct. Biol. 9:521–529, 1999; Liu et al., Methods Enzymol. 318:268–293, 2000). These mRNA-peptide fusions can then by purified and subjected to in vitro selection, yielding the isolation of novel peptide ligands.

Figure 1A:
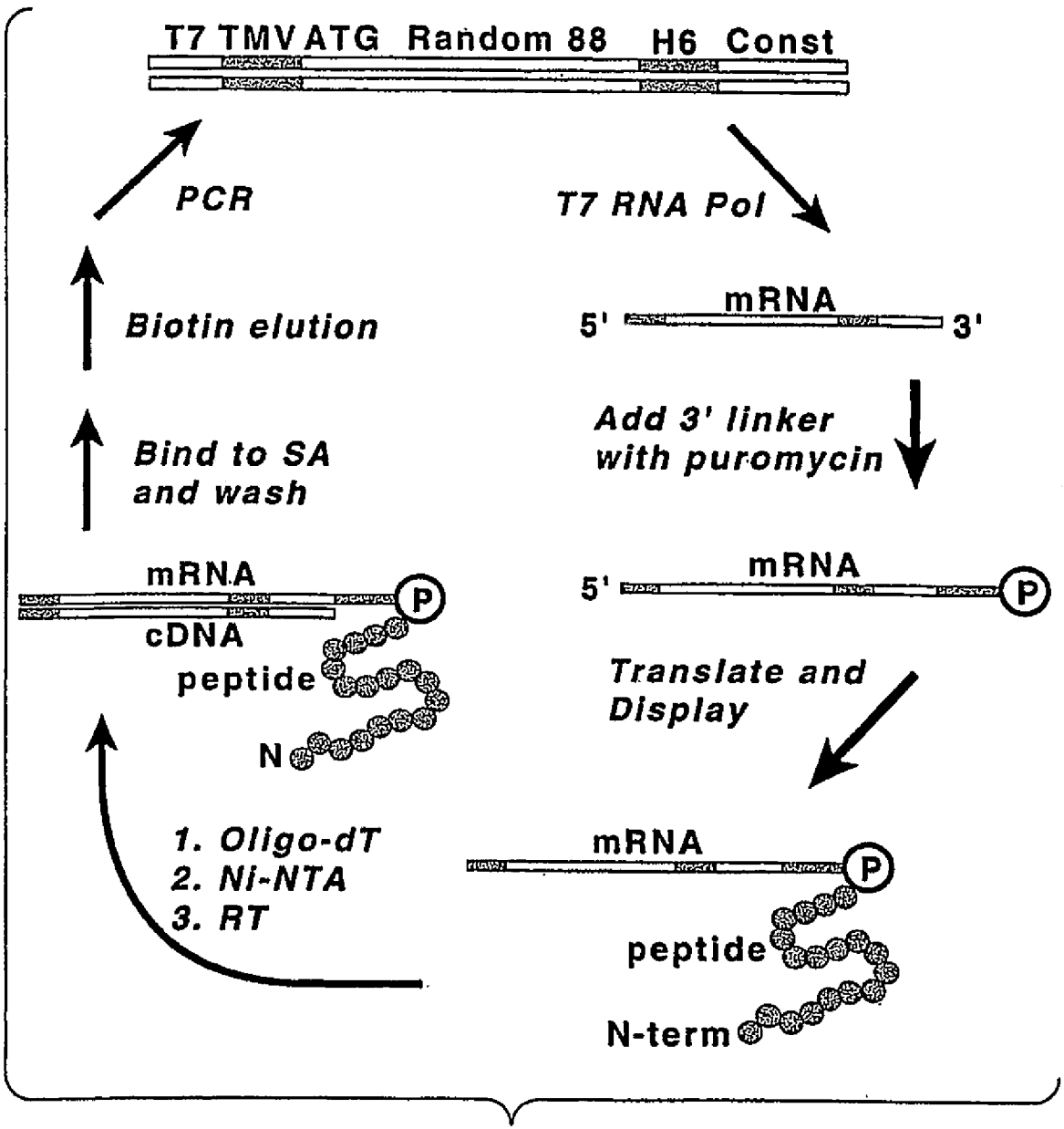

A DNA library encoding polypeptides of 108 amino acids was synthesized as described (Cho et al., supra). The library consisted of short cassettes concatamerized together. Each cassette encoded a random peptide with a pattern of polar versus non-polar amino acid side chains compatible with forming an amphipathic α-helix or β-strand (Cho et al., supra). The random region was 88 amino acids long, followed by a C-terminal invariant region containing a hexahistidine tag (FIG. 1A).

The library had a complexity of $2.4 \times 10^{14}$ at the DNA level. It was transcribed using T7 RNA polymerase (FIG. 1A), after which a "linker" oligonucleotide was added to the 3' end using T4 DNA ligase as described (Liu et al., supra; Cho et al., supra). The linker consisted of a 21 nucleotide long dA stretch, followed by a polyethylene glycol linker, followed by the sequence dA-dC-dC-puromycin (Liu et al., supra).

This puromycin-terminated mRNA was translated in vitro, using the Ambion (Austin, Tex.) in vitro translation kit under standard conditions for capped mRNA. The 10 mL reaction mixture was supplemented with 2 mCi $^{35}$S-methionine and a total methionine concentration of 10 μM. The reaction mixture also included 300 nM of the library of puromycin-linked mRNA molecules. After 1 hour at 30° C., $MgCl_2$ and KCl were added to 20 and 710 mM, respectively, and the reaction mixture was further incubated at room temperature for five minutes to increase the yield of displayed peptides. This in vitro translation produced $1.2 \times 10^{14}$ polypeptides linked via the puromycin moiety to their encoding mRNAs.

These mRNA displayed peptides were then purified on oligo-dT cellulose (which binds to the oligo-dA sequence in the linker) to remove polypeptides not fused to mRNA. For this purification procedure, the reaction mixture was diluted 10-fold into oligo-dT-binding buffer (1M NaCl, 50 mM HEPES, 10 mM EDTA, 0.25% Triton X-100, and 5 mM 2-mercaptoethanol at pH 7.9) and 80 mg oligo-dT cellulose (type 7, Amersham-Pharmacia, Piscataway, N.J.) and incubated with agitation at 4° C. for 30 minutes. The mixture was applied to a column (Poly-Prep chromatography column, Biorad, Hercules, Calif.), drained, washed with 10 mL oligo-dT-binding buffer, washed with 10 mL oligo-dT-wash buffer (300 mM NaCl, 20 mM HEPES, 1 mM EDTA, 0.25% Triton X-100, and 5 mM 2-mercaptoethanol at pH 7.9), and washed with 1 mL of 0.5× oligo-dT-wash buffer. The mRNA-displayed peptides were eluted with 4.5 mL water plus 5 mM 2-mercaptoethanol into tubes containing Triton X-100 and bovine serum albumin (BSA, New England Biolabs, Beverly, Mass.) at final concentrations of 0.15% and 15 µg/mL, respectively.

The mRNA-displayed peptides that eluted from the oligo-dT cellulose column were further purified on Ni-NTA agarose, which binds to the hexahistidine tags on the polypeptides, to remove any mRNA not fused to polypeptides. The eluted fractions from the oligo-dT cellulose purification were exposed to 0.5 mL Ni-NTA-agarose (Qiagen, Valencia, Calif.) in Ni-binding buffer [6 M guanidinium chloride, 0.5 M NaCl, 100 mM sodium phosphate, 10 mM Tris(hydroxymethyl)aminomethane, 0.1% Triton X-100, 5 mM 2-mercaptoethanol, 4 µg/mL tRNA (Boehringer-Mannheim, Indianapolis, Ind.), and 5 µg/mL BSA at pH 8.0)] and incubated for 30 minutes at room temperature. The matrix was then drained, washed with 12 column volumes Ni-binding buffer, and eluted with the same buffer plus 100 mM imidazole. Eluted fractions were combined and de-salted using two successive NAP columns (Amersham-Pharmacia, Piscataway, N.J.) equilibrated in 1 mM Tris(hydroxymethyl)aminomethane, 0.01% Triton X-100, 50 µM EDTA, 0.5 mM 2-mercaptoethanol, 0.5 µg/mL tRNA (Boehringer-Mannheim, Indianapolis, Ind.), and 50 µg/mL BSA at pH 7.6).

The mRNA portion was then reverse transcribed using Superscript II (Gibco BRL, Rockville, Md.) according to the manufacturers instructions, except that the mRNA concentration was about 5 nM and the enzyme concentration was 1 U/µL. To ensure a high yield in the reaction, a mixture of two primers were used: 1 µM of "splint" from the splinted ligation (Cho et al., supra), and 1 µM of the 3' PCR primer. After 30 minutes at 42° C., the temperature of the reaction mixture was raised to 50° for 2 minutes, and then cooled over 5 minutes to room temperature to allow gradual peptide folding. Finally, the contents were de-salted using NAP columns and subjected to scintillation counting. By comparing the $^{35}$S counts of the purified, reverse transcribed mRNA-peptide fusions to the $^{35}$S-methionine stock and taking into consideration the total methionine concentration in the translation reaction (10 µM), the number of displayed peptides in this sample was determined to be $6.7 \times 10^{12}$. This number also represents the complexity of the library, since it contained virtually no redundancy (the complexity of puromycin-linker template used in the translation exceeds the number of recovered displayed peptides by a factor of about 35).

Figure 1B:
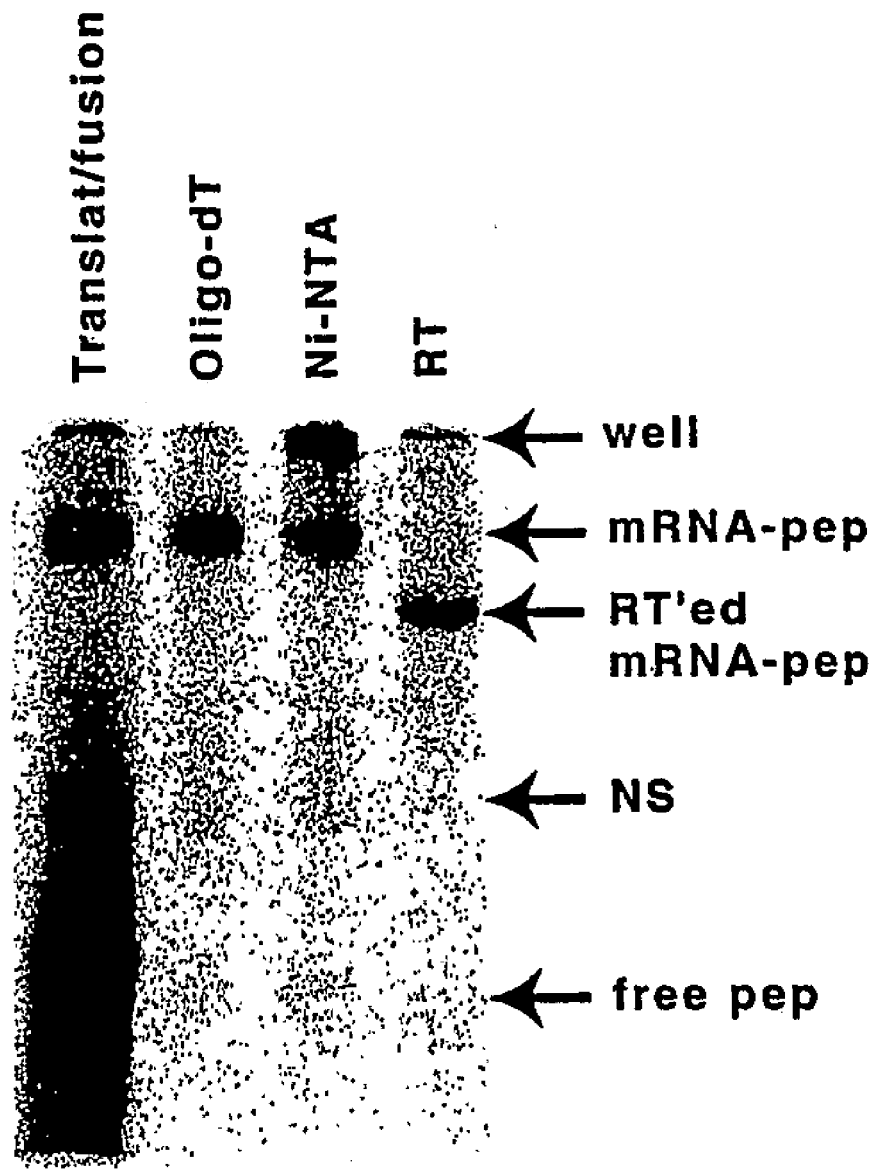

Samples from the synthesis and purification of the mRNA displayed peptides were run on an SDS-PAGE gel, as shown in FIG. 1B.

Selection of Streptavidin-Binding Peptides

For selection of peptides with high affinity for streptavidin, the above mRNA displayed peptide library was incubated with immobilized streptavidin (Ultralink immobilized streptavidin plus, about 4 mg/mL; Pierce, Rockford, Ill.) in streptavidin-binding buffer under reducing conditions (40 mM Tris(hydroxymethyl)aminomethane, 300 mM KCl, 2 mM EDTA, 0.1% Triton X-100, 5 mM 2-mercaptoethanol, 100 µg/mL BSA, and 1 µg/mL tRNA at pH 7.4). The amount of gel used was 0.5 mL in a total volume of 5.5 mL. After incubating for 20 minutes at room temperature, the contents were loaded onto a disposable chromatography column, drained, washed with 14 column volumes of streptavidin-binding buffer, and eluted with five successive aliquots, at 10 minutes intervals, of streptavidin-binding buffer plus 2 mM D-biotin (Sigma, St. Louis, Mo.) (FIG. 1A). The fraction of the library that survived this purification was 0.08%. Elution fractions were combined, de-salted on NAP columns, and then PCR-amplified to regenerate the double-stranded DNA library using the described conditions and primers in a 8 mL reaction mixture (Cho et al., supra).

Figure 2A:
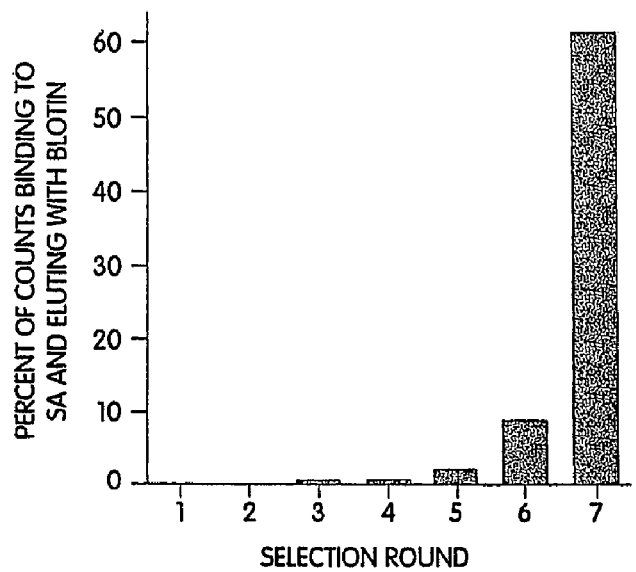

This concluded the first round of selection, and the remaining six rounds followed the same protocol except that the translation was scaled down 10-fold, and the number of column volumes for washing the streptavidin column was increased (32 volumes for round 2; 40 volumes for rounds 3, 4 and 6; and 25 volumes for rounds 5 and 7). The streptavidin-binding selection for rounds 5 and 7 was performed directly on the streptavidin-column eluate from the preceding selection rounds, without intervening amplification (the biotin was removed by three successive passages through NAP columns). PCR products amplified after the seventh selection round were cloned using the TOPO TA cloning kit (Invitrogen, Carlsbad, Calif.), following the manufacture's protocol. The fraction of the library that bound and eluted from the streptavidin column increased in each round, reaching 61% at round seven (FIG. 2A).

Characterization of the Selected Library

Figure 2B:
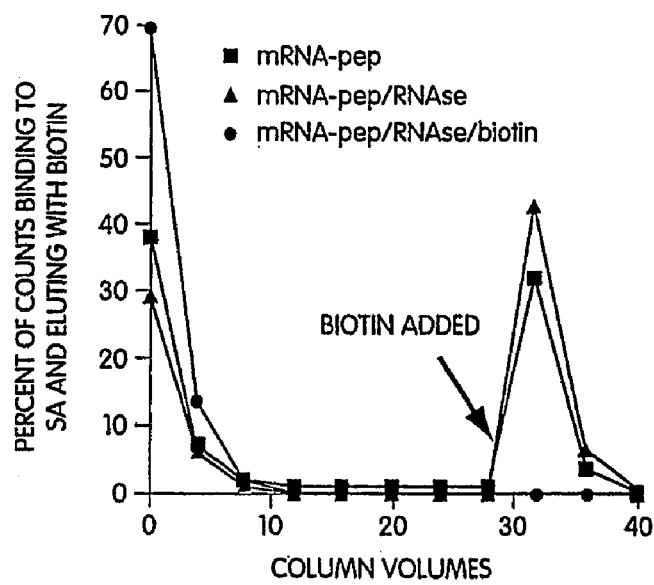

The eluate from the seventh round of selection was amplified by PCR. The resulting PCR DNA was used to synthesize a library of displayed peptides to confirm that the displayed peptides, rather than the RNA or DNA portion of the library constructs, were responsible for the interaction with streptavidin. Treatment of the library with RNAse A did not reduce the extent of binding/elution from the matrix (FIG. 2B). Also, biotin-saturated streptavidin showed no binding to the peptide library (FIG. 2B). These results demonstrated that the interaction of the selected peptides with the streptavidin matrix was specific for the unligated protein, rather than for any other component of the matrix.

Sequence Analysis of Selected Peptides

Thirty-three randomly chosen clones from the PCR DNA from round seven were chosen for sequencing. Twenty different sequences were observed (FIG. 3). Surprisingly, all 20 sequences were frame-shifted from the intended frame (frame 1) to frame 3 by deletion of two nucleotides or addition of one nucleotide. The designed pattern of polar and non-polar residues was therefore discarded, leaving an unpatterned, essentially random sequence. Prior to the selection, about half of the library members were in frame 1 throughout their entire open reading frames (Cho et al., supra). Frame 3 appears to have been enriched over frame 1 due to the increased frequency of the sequence HPQ. Frame 1 has a low incidence (1:45,000 library members) of the sequence HPQ due to the designed polar/non-polar pattern. By contrast, frame 3 had a much higher expected incidence of the HPQ sequence (1:64), similar in frequency to that of a library of the same length and with equal mixtures of all four nucleotides at each position (1:193). Also, frame 3 was rich in histidine, thus allowing retention on the Ni-NTA column. The Ni-NTA purification protocol was intended to eliminate library mRNA molecules not displaying peptide, but was not performed under sufficiently stringent conditions so as to eliminate peptides with small numbers of histidines. Frame 2 had a high incidence of stop codons.

Nineteen of the 20 clones had at least one HPQ motif, and five clones contained two such motifs (Table 1). The clones were organized according to the number of times the HPQ and related tripeptide motifs occur (Table 1). The number of amino acids between the two motifs, when present, ranged from four to 74.

Binding Affinities of Peptides

To rapidly assay each of the 20 selected peptides to determine their affinity for streptavidin, a new method for preparing, tagging and purifying the peptides was employed. For generation of the DNA-tagged peptides, plasmids containing single inserts were used as templates for PCR-amplification using the same 5' PCR primer as described for the library construction (Cho et al., supra), and a new 3' primer (5'-ATAGCCGGTGCCAAGCTTGCAGCCGCCA-GACCAGT-3'; SEQ ID No. 30), which altered the 3' RNA sequence to ACUGGUCUGGCGGCUGCAAGCUUG-GCACCGGCUAU (SEQ ID No. 31). This sequence was designed to anneal to the photo-crosslinking linker, which has the sequence 5'-psoralen-TAGCCGGTG-A17-CC-puromycin-3', in which the underlined bases are 3'-methoxy nucleotides and the remaining bases are deoxynucleotides (the oligonucleotide was synthesized using reagents from Glen Research, Sterling, Va.). This new primer changed the constant C-terminal peptide sequence from WSGGCHHHHHHSSA (SEQ ID No. 32) to WSGGCKLGTGY (SEQ ID No. 33), of which the last three amino acids may not be translated because they are annealed to the linker. Each DNA template was transcribed and gel purified as described (Cho et al., supra), and then incubated with the psoralen linker under the following conditions: 2 µM mRNA, 4 µM linker, 50 mM Tris(hydroxymethyl) aminomethane, 200 mM KCl, and 10 mM spermidine at pH 7.4 and 70° C. for 2 minutes, and then cooled to 4° C. over 5 minutes. Samples were then placed in the cold room in a 96 well plate (50 µL/well), one inch above which was suspended a UV lamp (366 nm, Ultraviolet Products, Inc., San Gabriel, Calif., model number UVL-21) for 15 minutes. Then, the reactions mixtures were de-salted using a G-50 Sephadex spin column (Boehringer Mannheim, Indianapolis, Ind.). The translation/display reactions and oligo-dT-purification were carried out as above. Finally, RNase A (200 ng/mL, 10 minutes, room temperature) was added to degrade the mRNA, leaving peptides fused to a short DNA oligonucleotide. Complete degradation was confirmed by SDS-PAGE analysis.

The resulting purified DNA-tagged peptides (DTP) were analyzed in a streptavidin column-binding assay, in which ~500 pM $^{35}$S-labeled DTP were mixed with 50 µL of the streptavidin matrix in streptavidin-binding buffer, in a total volume of 300 µL, and incubated for 10 minutes at room temperature with agitation. Then, the contents were loaded onto a chromatography column. The column was drained and washed with 80 column volumes of streptavidin-binding buffer, and then eluted with three consecutive aliquots (3 column volumes each) of streptavidin-binding buffer plus 2 mM biotin over a 15 minute period. All fractions (flow-through, washes, elutions, and irreversibly bound counts) were analyzed by scintillation counting to determine the fraction of DTP that bound streptavidin and eluted with biotin (Table 1). The non-selected clone in which two HPQ motifs (separated by 19 amino acids) were introduced encoded the sequence M DEAHPQAGPVDQADARLVQQGA LQHHPQGDRMMSGGCKLGTGY (SEQ ID No. 34), in which the underlined portions are identical the HPQ regions of clone SB2.

The results of this analysis are shown in Table 1. For comparison, two HPQ motifs, separated by 19 residues, were introduced into a control, unselected member of the library. The low percentage of this control peptide that specifically eluted from the streptavidin column (0.16%) indicated that the presence of two HPQ motifs was not sufficient for high affinity binding. In contrast, a greater percentage of the selected peptides (8.3 to 88%) was retained on the column during the washing step and then specifically eluted with biotin.

The dissociation constants of the selected peptides for streptavidin were measuring using an electrophoretic mobility shift assay (EMSA). In this assay, DTP's were incubated with varying amounts of pure streptavidin (Pierce Immunopure Streptavidin, Rockford, Ill.) in streptavidin-binding buffer plus 5% glycerol to increase the density of the solution so that it could collect at the bottom of the gel well. After incubating at room temperature for 20 minutes, the reactions mixtures were moved into the cold room, where they remained for 10 minutes before being carefully loaded onto a 10% polyacrylamide:bisacrylamide (37.5:1, National Diagnostics, Atlanta, Ga.) gel (thickness 0.7 mm, height 16 cm, width 18 cm) containing 2X TBE, 0.1% Triton X-100 and 5% glycerol. The gel, which had been pre-run for 30 minutes at 13 watts, and the running buffer were pre-cooled to 4° C. Then, the gel was run in the cold room at 13 watts, which increased the temperature of the gel to about 20° C. The gel was run for 45 to 120 minutes, depending on the mobility of the particular DTP. Then, the gel was fixed in 10% acetic acid and 10% methanol for 15 minutes, transferred to electrophoresis paper (Ahlstrom, Mt. Holly Springs, Pa.), dried, and analyzed using a PhosphorImager (Molecular Dynamics, Sunnyvale, Calif.).

The short DNA oligonucleotide tag on the DTP's allowed them to migrate in a native gel, and the addition of unlabeled ligand (i.e., streptavidin) caused a mobility shift for several of the clones. The concentration of DTPs was less than 1 nM in each titration, and thus the dissociation constant ($K_D$) can be approximated by the concentration of streptavidin that results in half of the DTP being mobility-shifted. To determine the $K_D$, several different measurements were taken in the range of 25–75% of DTP bound (values outside of this range were unreliable due to background and close proximity of the bound and unbound bands in the gel). The $K_D$ was determined using the equation $K_D=[streptavidin]*R$, where R is the ratio of unbound to bound DTP (ratio of unshifted to shifted band). Independent measurements on gels prepared at different times were used for each clone (the number of different measurements, n, is shown in Table 1). Streptavidin concentrations were measured by $UV_{282}$, using the molar extinction coefficient of 57,000 per monomer.

Figure 4A:
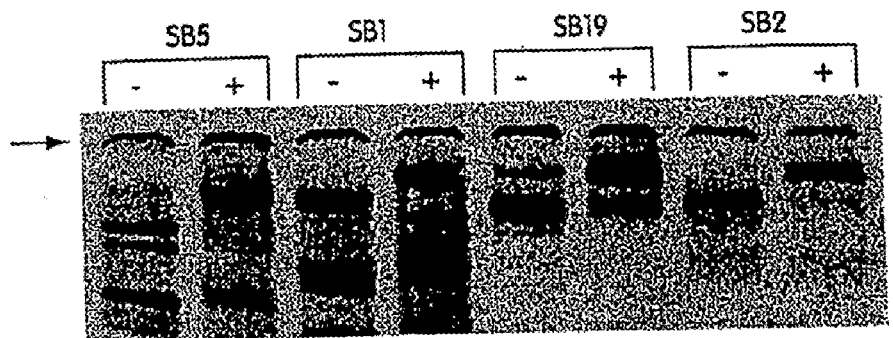
Figure 4B:
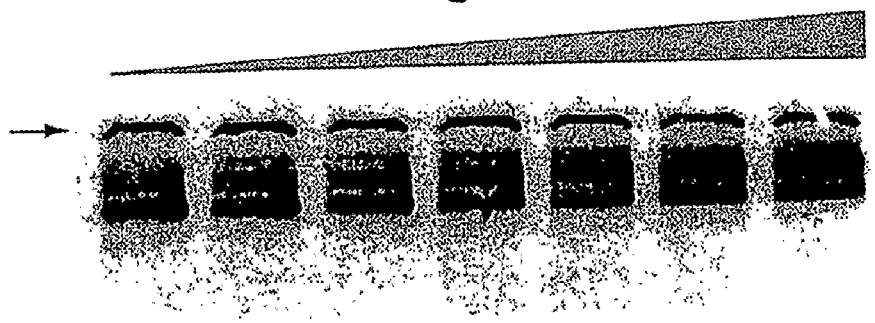
Figure 4C:
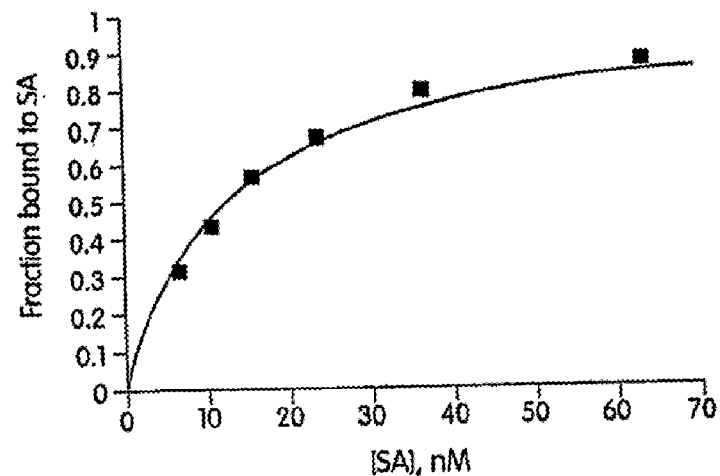

Examples of these mobility shifts in the presence of streptavidin are shown in FIG. 4A. Some clones showed either no shift or poorly defined bands, suggesting that the lifetime of these complexes was too short for detection using this method. We chose five of the most well behaved clones and quantitatively examined their mobility shifts in response to a range of streptavidin concentrations. An example of a streptavidin titration experiment for peptide SB19 is shown in FIG. 4B, and the data is graphed in FIG. 4C. The dissociation constants for the clones ranged from 110 nM to less than 5 nM (Table 1). These surprisingly high affinities were comparable to those for monoclonal antibody-antigen interactions, demonstrating that even random, non-constrained peptide libraries can be a source of avid ligands to proteins that do not normally function in peptide binding.

Dissection of Clone SB19

Clone SB19 possessed only one HPQ motif, bound to 85% in the column binding assay, and had a $K_D$ for streptavidin of 10 nM (Table 1). A series of C-terminal truncation constructs (C1–C4) were constructed and assayed in the streptavidin column-binding assay (FIG. 5). C-terminal truncation analysis of clone SB19 was performed using standard methods by amplifying the clone with the original 5' primer and a series of 3' primers that truncated the sequence at various positions and also replaced two codons (encoding Asp and Trp) in the C-terminal constant region with methionine codons to increase the $^{35}$S-incorporation. Analogous primers were used for the N-terminal truncation analysis, except that no change was made in the N-terminal constant sequence.

Deletion of up to 56 residues had no observable effect on the binding strength. Peptide SB19-C4 retained only the first 38 residues from the selected construct (plus the C-terminal MMSGGCKLG sequence, SEQ ID No. 36). Mutating the HPQ motif to HGA reduced the activity by three orders of magnitude (compare construct C4 to M1). Results from the N-terminal truncation constructs (N1–N3) suggested that binding determinants were spread throughout the N-terminal 38 residues of peptide SB19. Of the peptides tested, SB19-C4 was therefore the minimal peptide retaining full activity in this assay. EMSA analysis of peptide SB19-C4 confirmed high affinity streptavidin-binding, but a fraction (13%) of the peptide was inactive even at streptavidin concentrations >1 μM. The majority (87%), however, had an apparent $K_D$ of 4.9 nM after correction for the amount of inactive peptide.

Purification of Fusion Protein Containing Streptavidin-Binding Peptide

Figure 6:
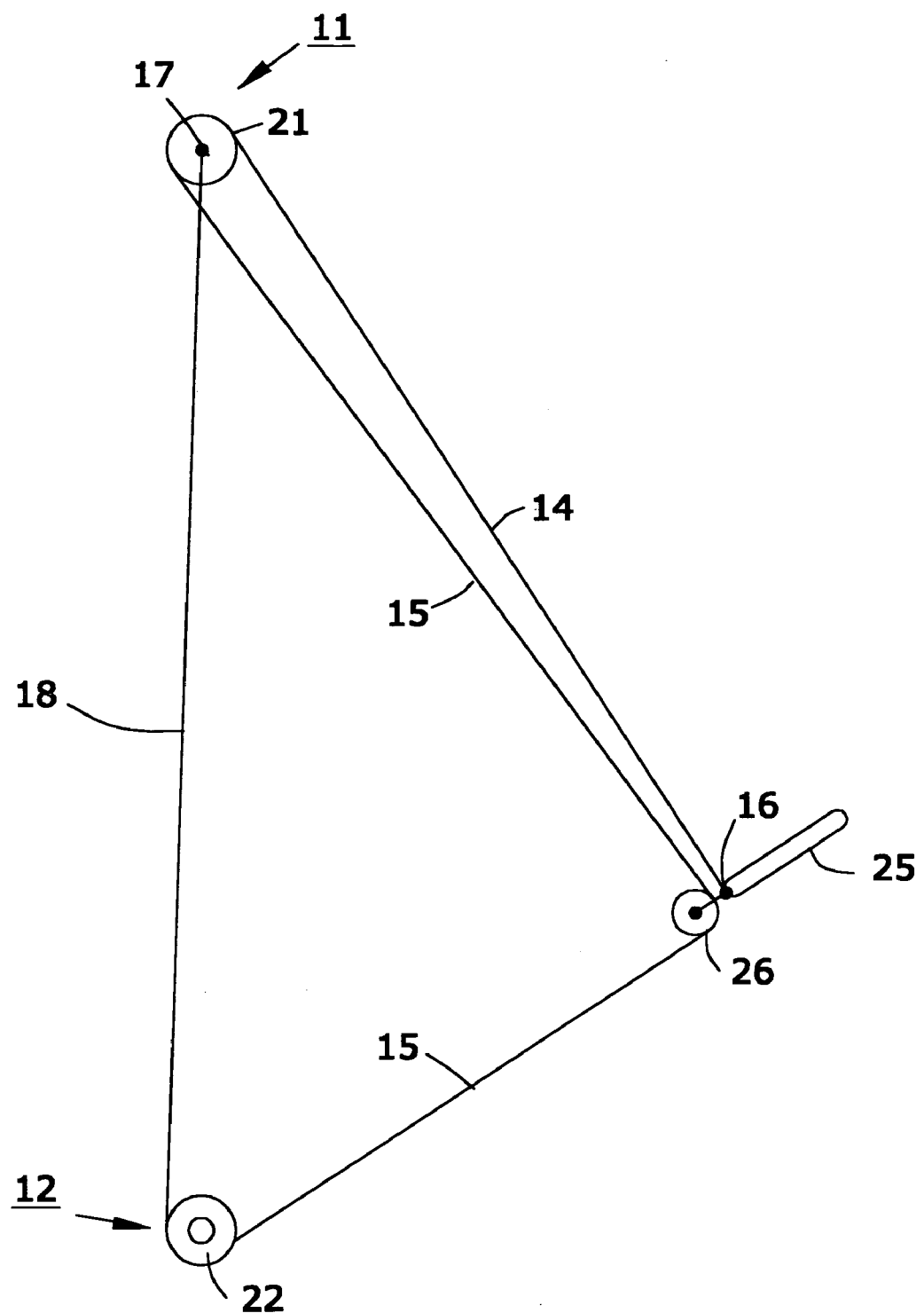
FIG. 6A is the nucleotide sequence of the plasmid used for expression of a fusion protein containing a streptavidin-binding peptide (SEQ ID No.: 37).
FIG. 6B is the amino acid sequence of the encoded protein (SEQ ID No.: 38) which contains, from the amino- to carboxy-terminus, maltose-binding protein, a streptavidin-binding peptide (SEQ ID No.: 35, FIG. 7A), a hexahistidine tag, and another peptide called 2r18-19dN.
FIG. 6C is the amino acid sequence of 2r18-19dN (SEQ ID No.: 39).
Figure 7:
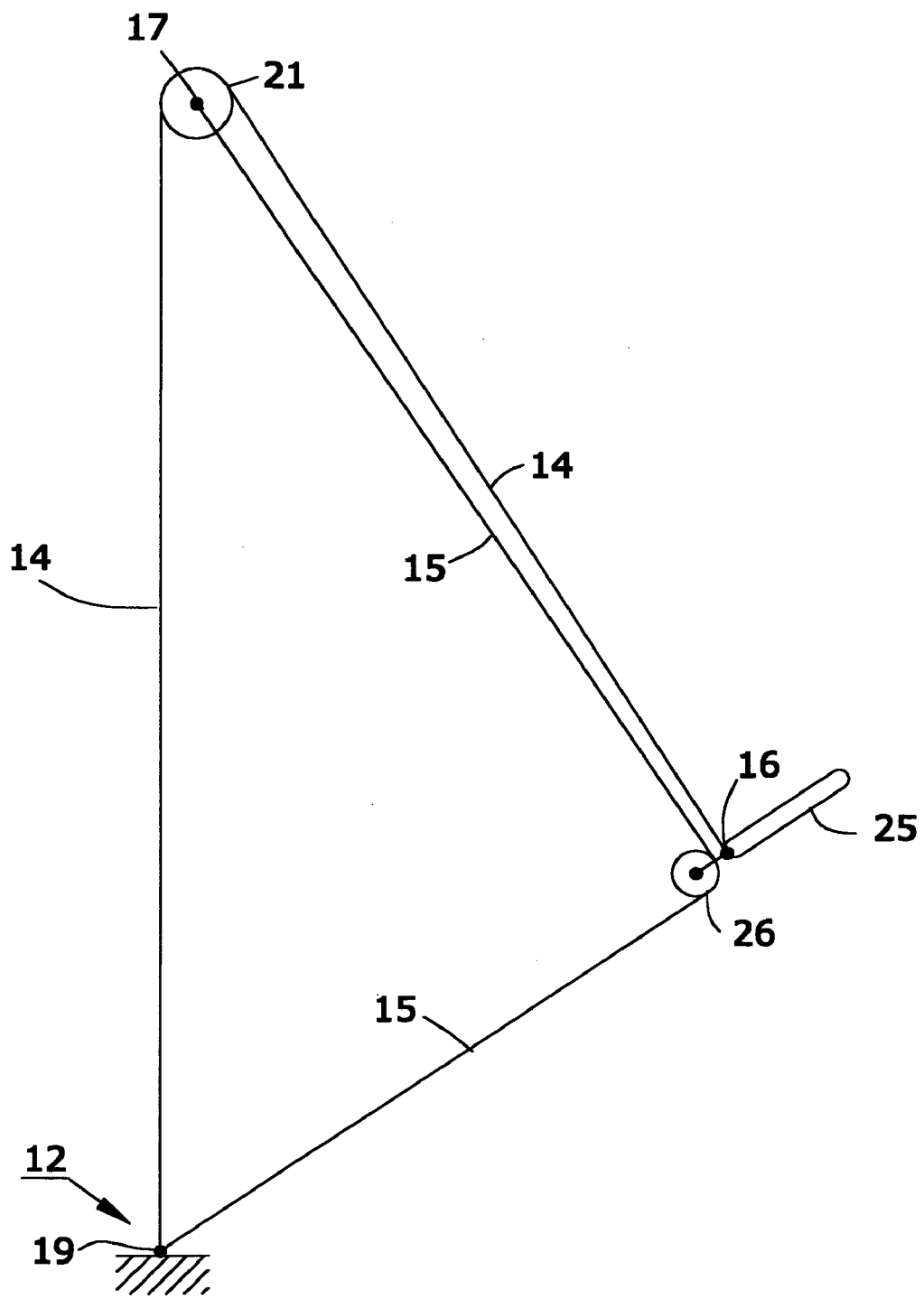
FIG. 7A is the amino acid sequence of the streptavidin-binding peptide (SEQ ID No.: 35) used as an affinity tag for the purification of the fusion protein listed in FIG. 6B. This peptide contains the first 38 amino acids of the SB19-C4 peptide (FIG. 5).
FIG. 7B is a picture of an SDS-PAGE gel showing the purity of the fusion protein after elution from the streptavidin column (lane 2) compared to the purity of the E. coli lysate that was applied to the column (lane 1).
Figure 11:
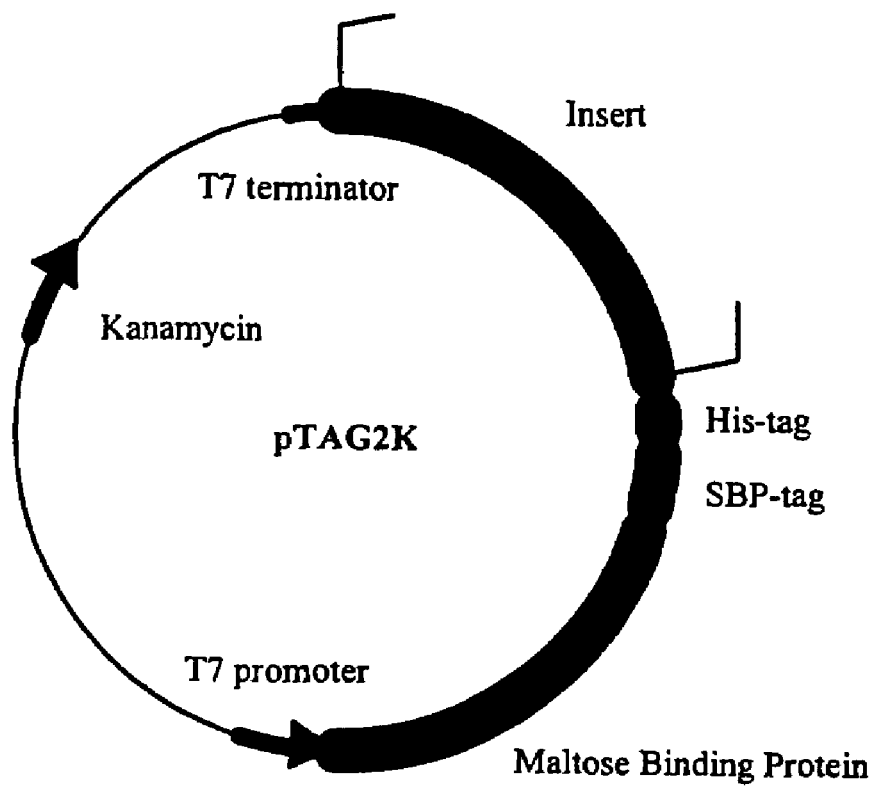
FIG. 11 is a map of the pTAG2K vector indicating the order of the domains in the multiply-tagged fusion protein it encodes.

A fusion protein containing the first 38 amino acids of the SB19-C4 streptavidin-binding peptide (FIG. 7A) was expressed in *E. coli* and then purified from the cell lysate. For the expression of the fusion protein, BL21 (DE3) cells were transformed with a plasmid containing a Maltose Binding Protein—Streptavidin-binding Peptide—His$_6$-Protein of Interest insert (FIG. 11) which encodes a fusion protein containing, from the amino- to carboxy-terminus, maltose-binding protein, the first 38 residues of the SB19-C4 sequence, a hexahistidine tag, and another peptide called 2r18-19dN (FIGS. 6A–6C). This insert was constructed using standard molecular biology techniques (see, for example, Ausubel et al., supra). Each of these domains of the fusion protein is separated by a few amino acids to allow proper folding of the domains.

A kanamycin-resistant colony was selected and grown overnight in 10 ml LB media with 50 mg/liter kanamycin at 37° C. This starter culture was diluted 100-fold into 1000 ml LB with 50 mg/liter kanamycin, and the culture was grown at 37° C. to OD$_{600}$ of 1.6–1.8 at 37° C. Expression of the fusion protein was induced by addition of 1 mM IPTG, and the culture was grown for another two hours. The cells were pelleted by centrifugation at 3000–5000×g for 20 minutes. The pelleted cells were resuspended in 5% of the original volume of a buffer appropriate for the subsequent affinity purification method. For purification on an amylose column the cells were resuspended in 1 mM EDTA and MBP buffer (10 mM HEPES.HCl, 10 mM HEPES.Na$^+$, 200 mM KCl, 0.25% w/w Triton X-100, and 10 mM BME at pH 7.4) and frozen slowly at −20° C. overnight. The sample was thawed in the morning and sonicated on ice. The cell lysate was obtained by collection of the supernatant after centrifugation at 14,000×g for 20 minutes at 4° C.

Figures 7A, 7B:
Figure 10A:
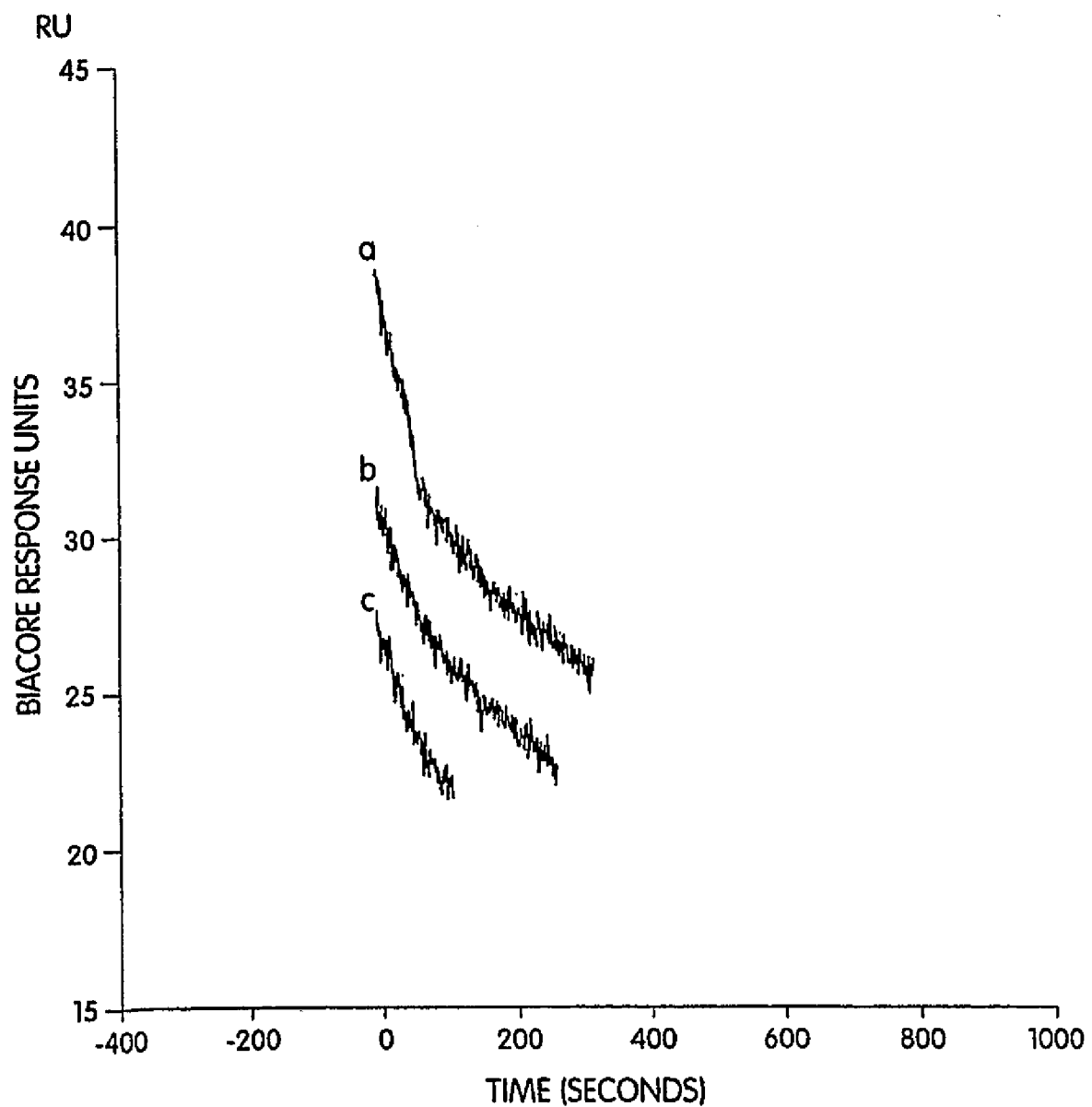
Figure 10B:
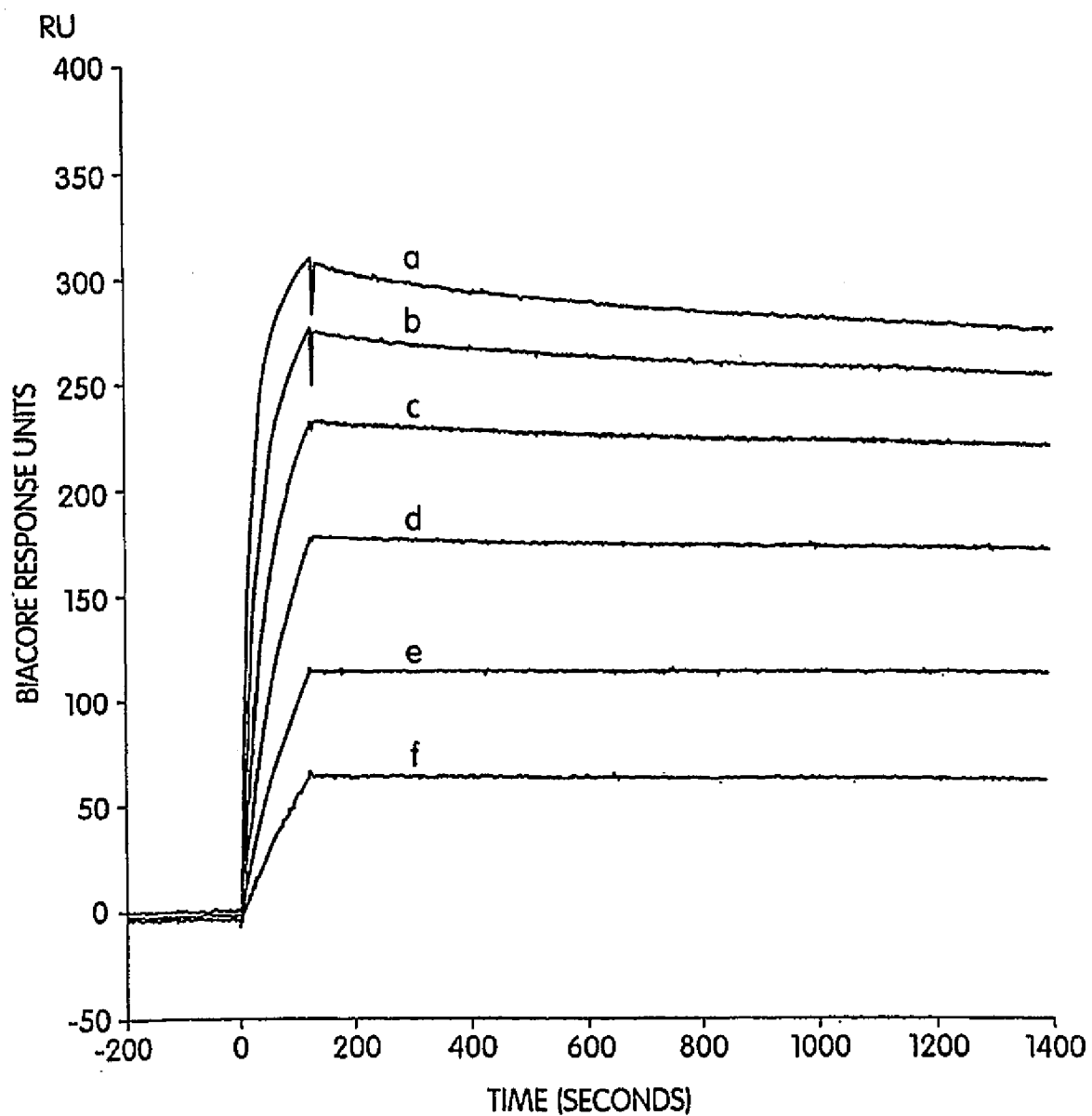
Figure 11:
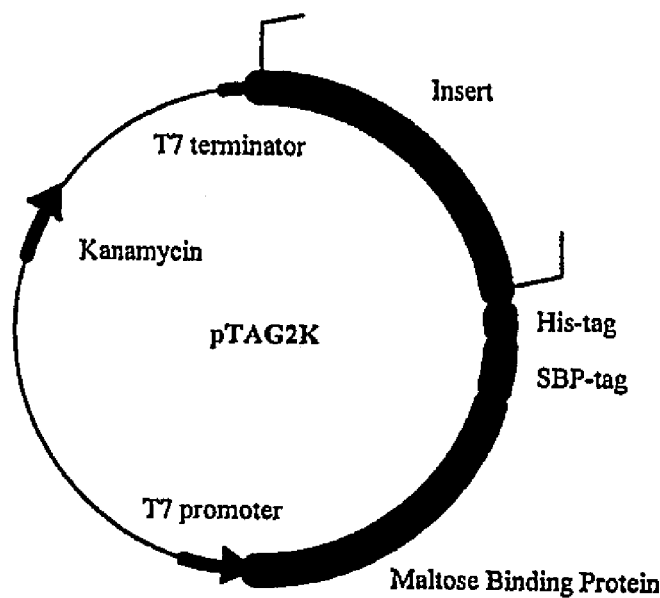
Figure 12:
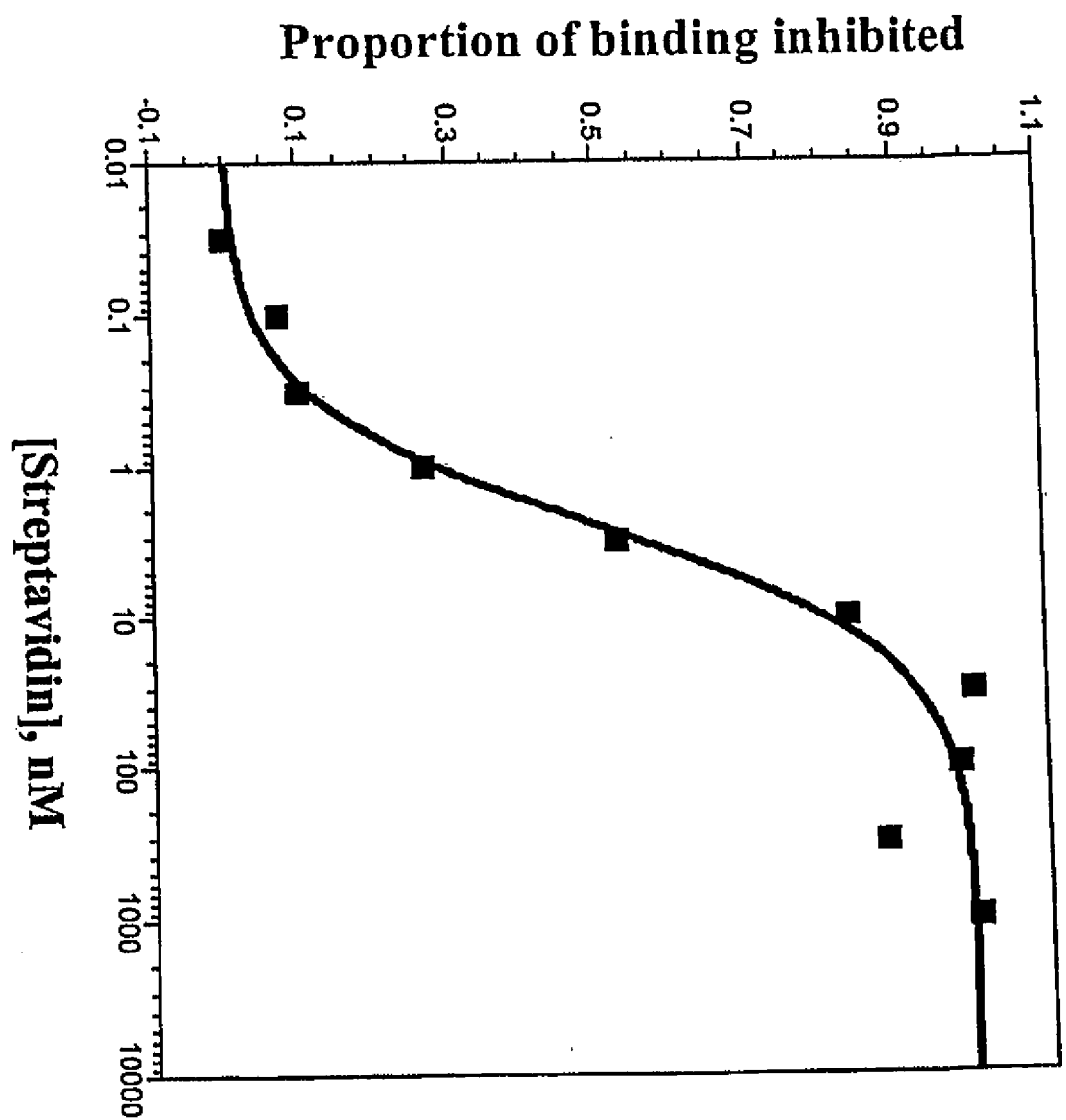
Figure 13:
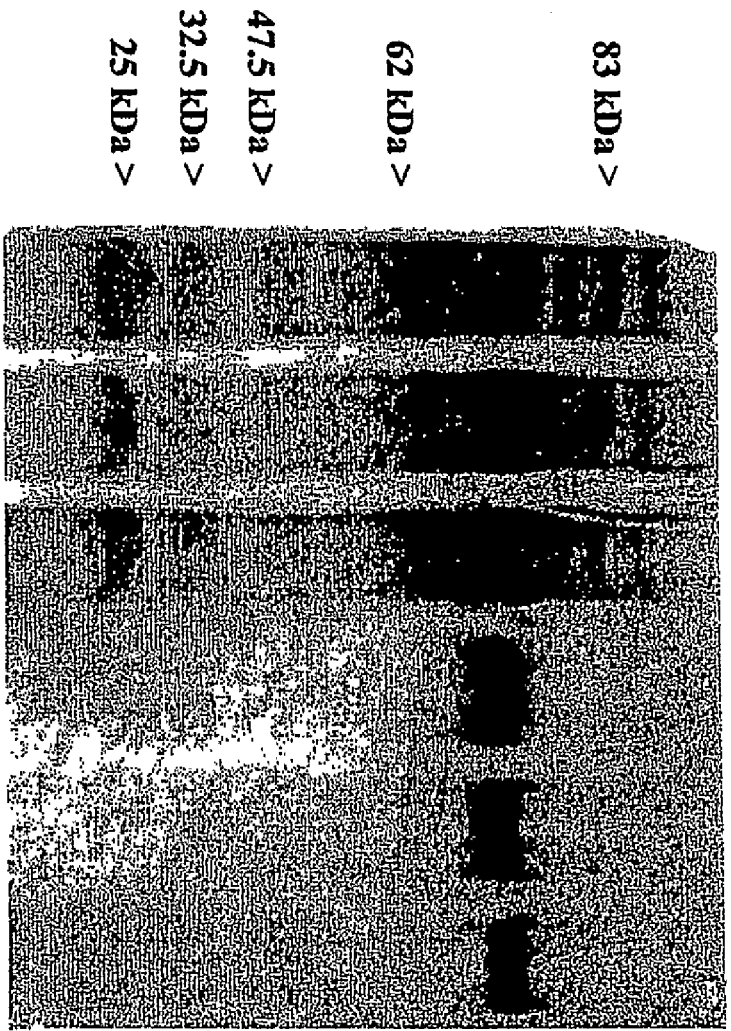
Figure 14:
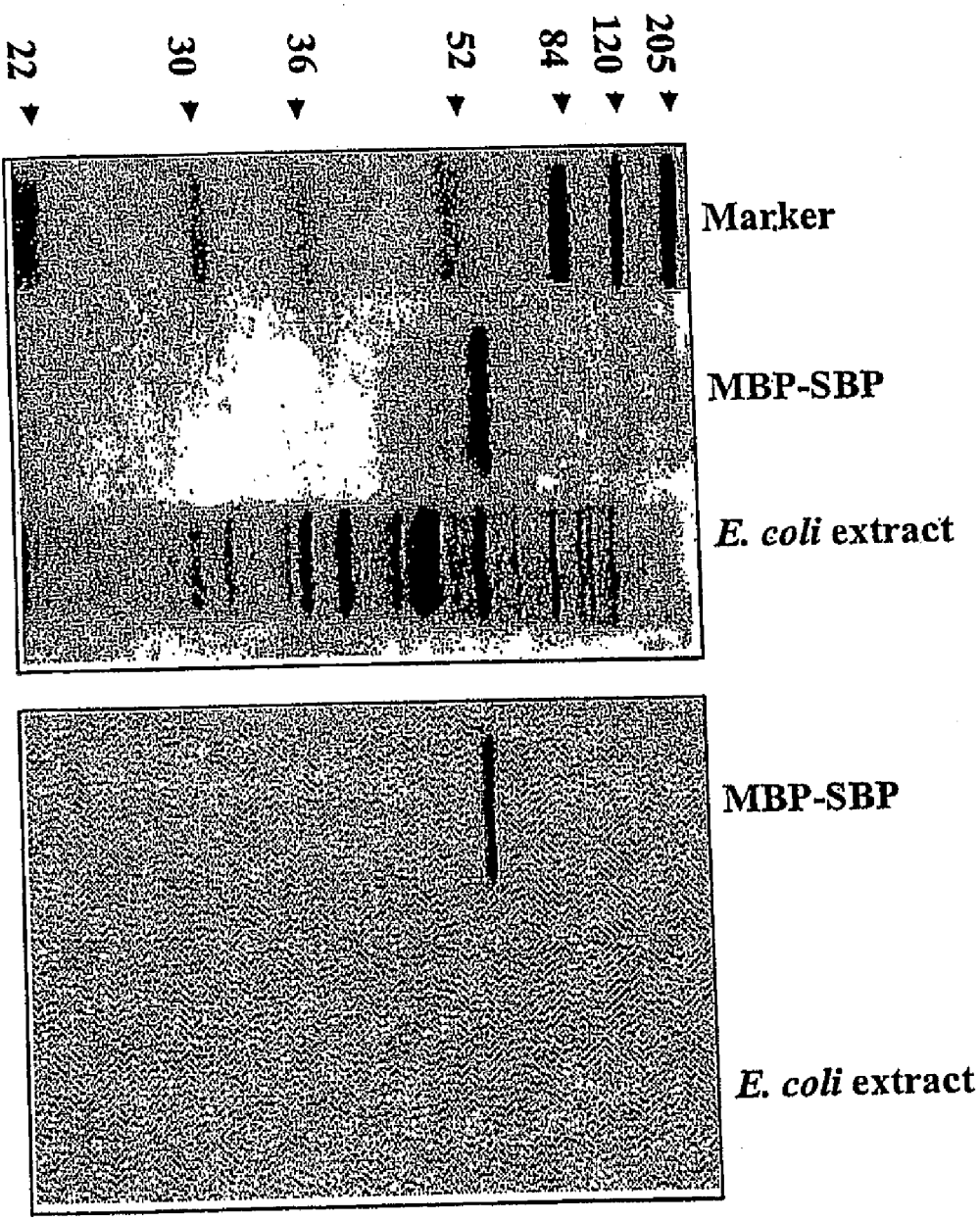
Figure 15:
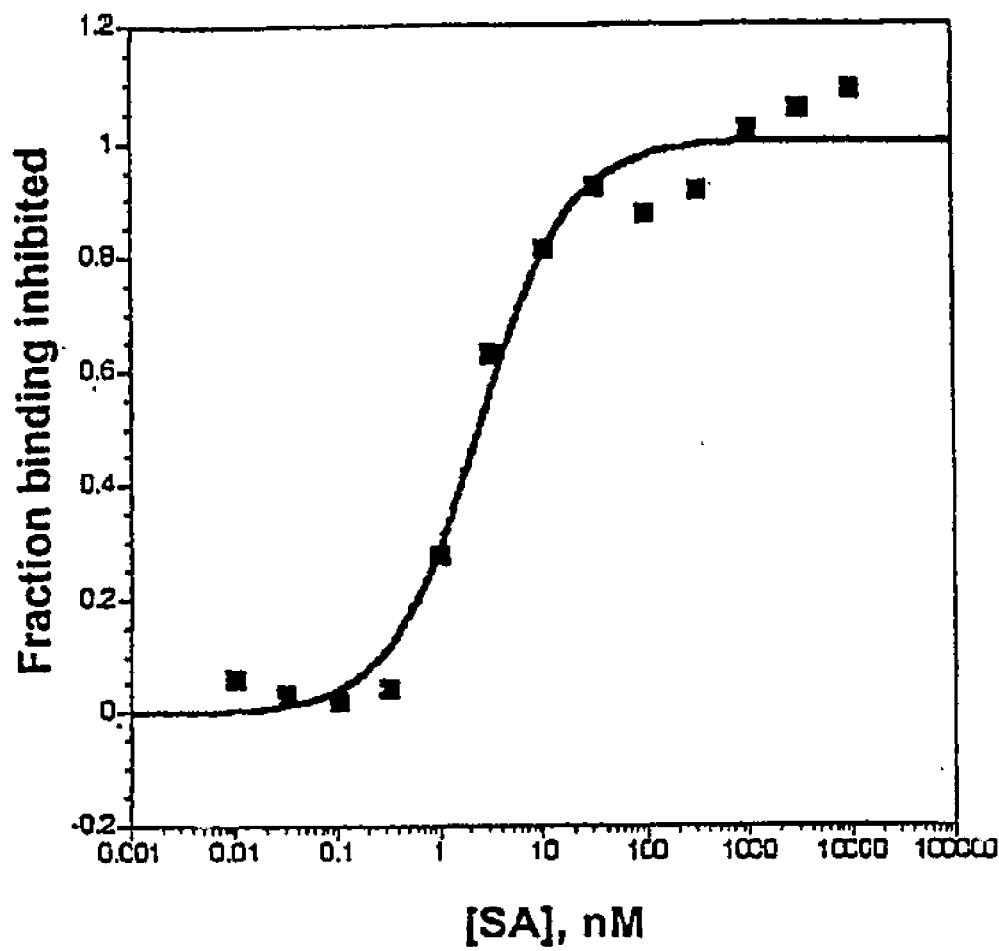

To purify the fusion protein, the cell lysate was applied to a column containing immobilized streptavidin, with a capacity of about 1 mg/ml, that had been washed with eight column volumes of MBP buffer. Then, the column was washed with 12 column volumes of MBP buffer. The fusion protein was eluted with MBP buffer containing 2 mM biotin. Samples of the cell lysate and eluted protein were analyzed by SDS-PAGE on an 8% gel (FIG. 7B). The lane containing the purified protein had a band of the expected size. No other bands were observed, except for a faint band of slightly higher mobility (FIG. 7B). This band was probably a degradation product of the fusion protein that was missing a few amino acids from either the amino- or carboxy-terminus but retained the streptavidin-binding peptide and thus retained the ability to bind the streptavidin column. Thirty percent of the fusion protein loaded onto a column containing immobilized streptavidin was recovered after washing the column with 12 column volumes of buffer. Thus, the high affinity of the fusion protein for streptavidin allowed extensive washing of the column to remove contaminating proteins, while retaining a significant amount of the desired fusion protein.

More stringent conditions eliminated the contaminating protein of higher molecular weight. The soluble fraction of lysed induced cells was prepared in Streptavidin-binding buffer (SBB: 300 mM KCl, 40 mM Tris(hydroxymethyl) amino methane, 5 mM 2-mercaptoethanol, 2 mM EDTA, 0.1% Triton-X 100, pH 7.4) as described above. This sample (e.g., 79 mg net weight cells in 1 ml SBB) was applied directly to the immobilized streptavidin matrix (e.g., column volume 100 μl; Ultralink Immobilized Streptavidin Plus, Pierce, Rockford Ill.) and then incubated at 4° C. for 30 minutes. The matrix was then washed with 40 column volumes of SBB and then eluted with 3 successive 2 column volume aliquots of SBB containing 2 mM biotin for 10 minutes each. Samples of each of the lysed uninduced and lysed induced cells, the soluble fraction, and the elution fraction were then analyzed on an 8% SDS-Tricine PAGE gel, and then stained with Coomassie Brilliant Blue. In a typical experiment, 1 ml of the soluble fraction of lysed induced cells was loaded onto 0.1 ml of the affinity matrix.

Purification using the His-tag was also carried out in an analogous manner to the streptavidin binding peptide-tag procedure with the same amounts of cells and in the same volumes. The soluble fraction was prepared in His-tag binding buffer (300 mM NaCl, 50 mM sodium phosphate, 0.25% Triton X-100, 10 mM imidazole, pH 8.0). The sample was applied directly to the Ni-column (Ni-NTA, Qiagen, Valencia Calif.) and then incubated at 4° C. for 30 minutes. The matrix was then washed with 40 column volumes of the same buffer containing 20 mM imidazole and then eluted with 3 successive 2 column volume aliquots of the same buffer containing 250 mM imidazole for 10 minutes each. Samples were analyzed as described above.

Purification using the maltose-binding protein sequence was carried out in an analogous manner to the streptavidin binding peptide-tag procedure with the same amounts of cells and in the same volumes. The soluble fraction was prepared in maltose-binding protein binding buffer (200 mM KCl, 20 mM HEPES, 10 mM 2-mercaptoethanol, 0.25% Triton X-100, pH 7.4). The sample was applied directly to the amylose column (New England Biolabs, Beverly Mass.) and then incubated at 4° C. for 30 minutes. The matrix was then washed with 40 column volumes of the same buffer and then eluted with 3 successive 2 column volume aliquots of the same buffer containing 10 mM maltose for 10 minutes each.

Figure 13:
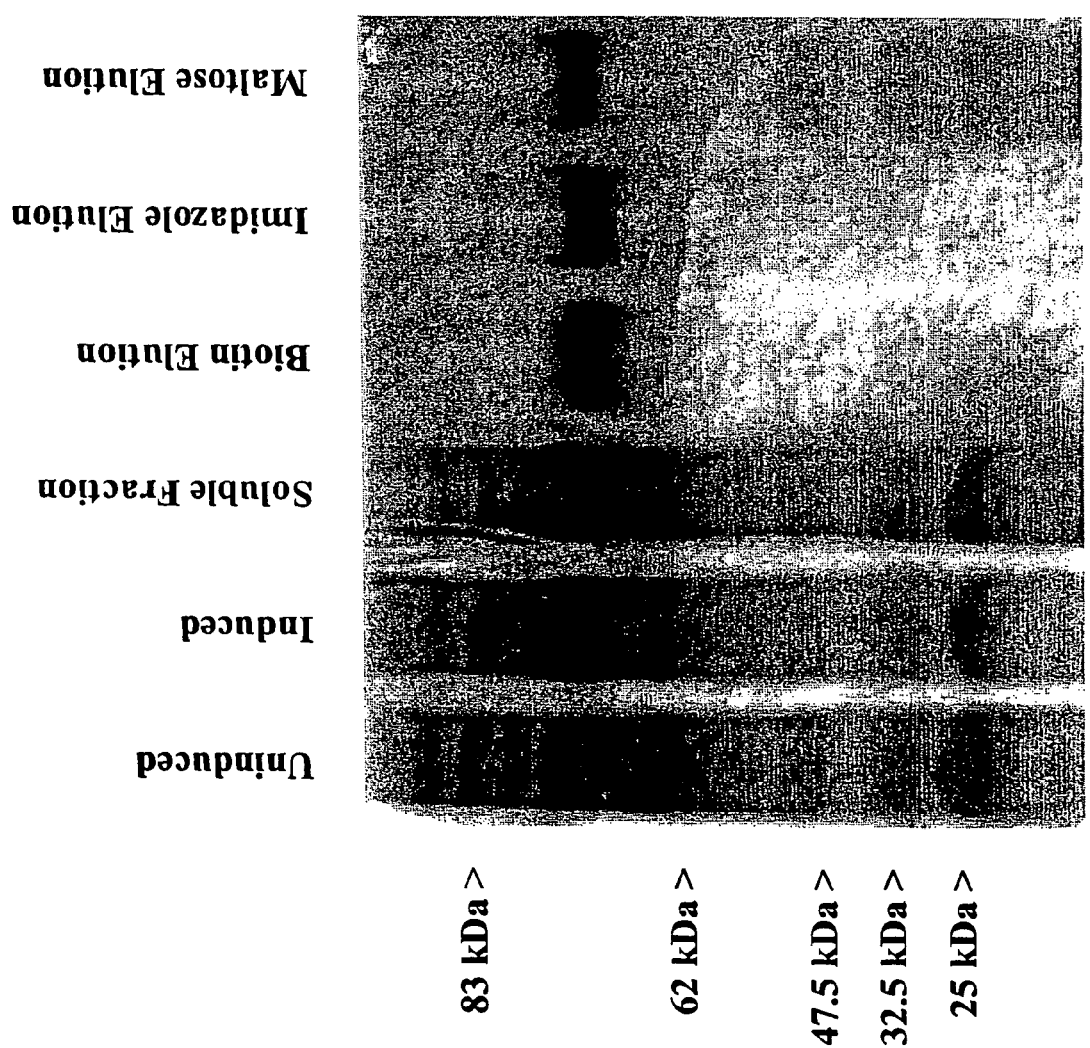
FIG. 13 is a purity assay for a single-step purification of streptavidin binding peptide-tagged (multiply-tagged) protein from lysed cells. Purity is compared to samples processed upon the basis of the His-tag or the maltose-binding protein sequences contained in the same protein. Lanes 1 and 2 show lysed E. coli prior to and after IPTG-induction, respectively. Lane 3 shows the soluble fraction of E. coli lysate in streptavidin-binding buffer. Lanes 4 through 6 show approximately equal amounts of purified proteins from the elution fractions of the streptavidin binding peptide-tag purification, the His-tag purification, and the maltose-binding protein purification, respectively.

For detection, ten picomoles of the loaded and eluted samples from the immobilized streptavidin column, the Ni-column, and the amylose column was loaded onto a 12% SDS-Tricine PAGE gel. In the adjacent lane, a whole bacterial extract from BL21 (DE3) cells was loaded. The whole cell extract was prepared by growing the cells to saturation in LB, removing the media by centrifugation, and re-suspending them in 10% of the original culture volume with the SDS-PAGE protein-loading buffer. Six microliters of this extract was run on the gel. These two samples and a molecular weight marker were run side by side on the gel in duplicate. After running the gel, it was stained with Coomassie Brilliant Blue This gel is shown in FIG. 13. A band of the correct size was purified using each of the three columns. Purification on immobilized streptavidin gave the highest purity sample. No other bands were visible by Coomassie Brilliant Blue-stained SDS-Tricine PAGE gel analysis. At least one impurity was detected in the Ni-NTA-purified sample, and several contaminants were apparent in the amylose-purified sample. These results suggest that the streptavidin binding peptide-tag provides superior purity after a single purification step from lysed induced cells.

Detection of Fusion Proteins Containing Streptavidin Binding Peptides Using Streptavidin-Derived Reagents Recombinant proteins containing streptavidin affinity tags may also be detected using reagents that bind to these affinity tags. A wide range of streptavidin-derivatized reagents is commercially available, and as a consequence the streptavidin binding peptide-tag provides a versatile detection tool. To demonstrate the utility of this interaction, an experiment was performed in which a recombinant protein was probed with streptavidin-derivatized horseradish peroxidase.

In this experiment the multiply-tagged protein was purified on the streptavidin column. The purified protein and an E. coli cell lysate were electrophoresed in adjacent lanes of a SDS-Tricine PAGE gel as described above. The protein on the gel was transferred to nitrocellulose (Trans-blot transfer medium, 0.2 μm, Biorad catalog number 162-0112) at 10 V for 30 minutes using the manufacturer's instructions (Trans-blot semi-dry transfer cell, Biorad catalog number 170-3940). Efficient protein transfer was confirmed by the presence of the pre-stained molecular weight markers on the nitrocellulose.

After transfer, the nitrocellulose was incubated in TBS (25 mM TrisHCl, 138 mM NaCl, 2.68 mM KCl, pH 7.4) plus 0.05% Polyoxyethylene-sorbitan monolaurate (Tween-20) and 3% BSA for 1 hour at room temperature. The blot was then briefly rinsed with the same buffer without BSA, and then a streptavidin-derivatized horseradish peroxidase conjugate (Amersham-Pharmacia, product number RPN1231) was added at a 1,000-fold dilution in TBS/0.05% Tween-20/3% BSA, and allowed to incubate for 1 hour at room temperature. The blot was then washed 3 times with TBS/ 0.05% Tween-20, and then one time with TBS. The HRP substrate (3,3',5,5'-tetramethylbenzidene, Promega catalog number W4121) was then added according to the manufacturers instructions, and the blot was developed for approximately 1 minute.

Figure 14:
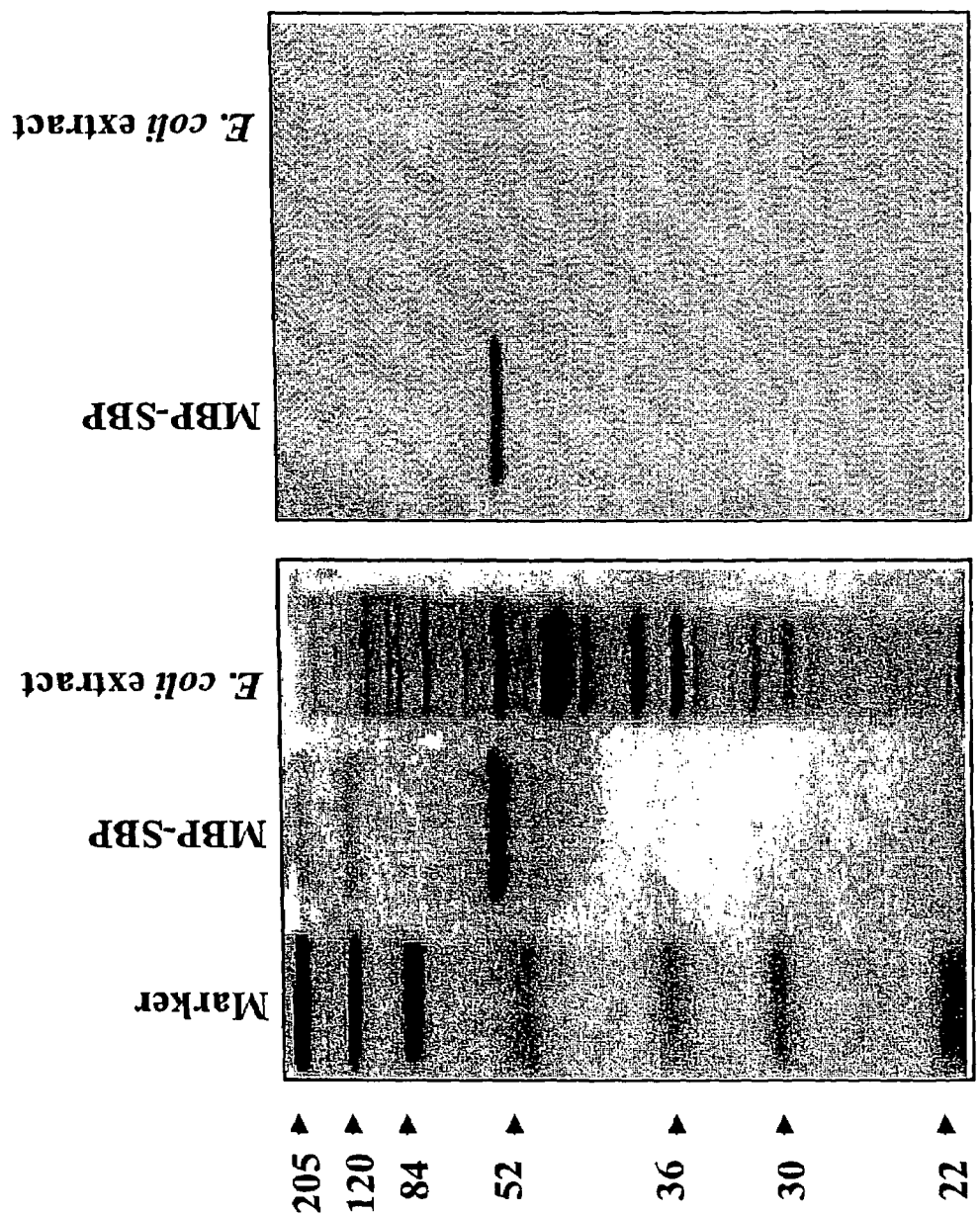
FIG. 14 illustrates a detection of a streptavidin binding peptide-tagged protein with streptavidin-derivatized horseradish peroxidase. The left-hand panel shows the Coomassie Brilliant Blue staining of an SDS-Tricine PAGE gel of the purified streptavidin binding peptide-tagged (multiply-tagged) protein and an E. coli extract. These same samples were also run on a different portion of the same gel and then transferred to a nitrocellulose membrane. The right-hand panel shows the result of the probing of this membrane with streptavidin-derivatized horseradish peroxidase. The only observed signal is for the streptavidin binding peptide-tagged protein, with no staining of other proteins in the extract.

These results are shown in FIG. 14. The streptavidin binding peptide-tagged protein is readily observed, and no proteins from the E. coli lysate are labeled, thus indicating the specificity of this interaction. Streptavidin-derivatized horseradish peroxidase and other streptavidin-derivatized reagents therefore provide many alternative methods of detecting streptavidin binding peptide-tagged proteins on membranes, plates, tissue sections, et cetera.

Yield of Fusion Proteins Containing Streptavidin-Binding Peptides

When scaling up protein expression to one milligram and above, the capacity and expense of the affinity matrix often begins to become important. To measure the capacity of the three matrices described above for their respective tag sequences, each matrix was overloaded with the multiply-tagged protein. Cells over-expressing this protein were split into three aliquots and re-suspended in different buffers according to the matrix that was to be used. The sample applied to immobilized streptavidin was extracted into streptavidin-binding buffer, and the samples for the other two purifications were extracted into the buffers recommended by the manufacturers of the two matrices, as described above.

The amount of protein in the flow-throughs, washes, and elution fractions was measured using the Bradford assay. We confirmed that each column was overloaded by observing the multiply-tagged protein in the flow-through fractions from each column. Purification using Ni-NTA agarose (His-tag/imidazole) yielded 12 mg of protein per ml of matrix. The amylose column yielded 4.4 mg of protein per ml of matrix. The immobilized streptavidin column yielded 0.5 mg of protein per ml of matrix (0.53 mg/ml with a standard deviation of 0.07 mg/ml, n=4). The overall capacity of immobilized streptavidin for the streptavidin binding peptide-tag was therefore lower than that of the Ni-NTA agarose or amylose matrices for their respective tags, but significantly greater than that of immobilized antibody matrices for purifying proteins upon the basis of epitope tags.

Biacore Analysis of the Affinity of a Fusion Protein for Streptavidin

Figure 9:
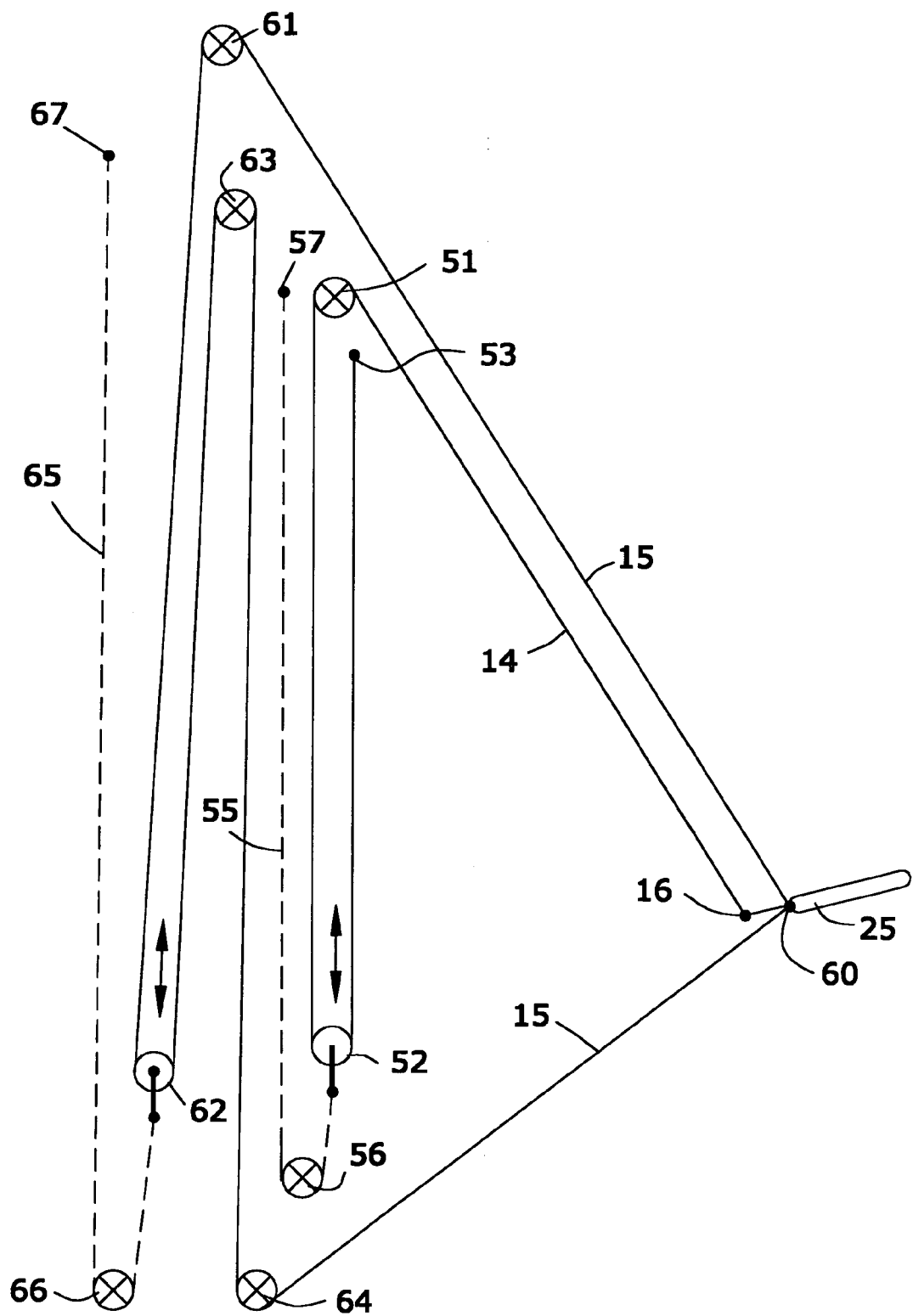
FIG. 9A is the polynucleotide sequence of the vector encoding a fusion protein containing maltose-binding protein, a streptavidin-binding peptide (SEQ ID No.: 35, FIG. 7A), and a hexahistidine tag.
FIG. 9B is the amino acid sequence of the encoded fusion protein. The sequence of the streptavidin-binding peptide which contains the first 38 amino acids of the SB19-C4 peptide is underlined.

The SB19-C4 streptavidin-binding fusion protein was expressed and purified from E. coli. This fusion protein contained, from the amino- to carboxy-terminus, maltose-binding protein, the first 38 amino acids of the SB19-C4 sequence, and a hexahistidine tag (FIG. 9B, SEQ ID No. 41). The plasmid (FIG. 9A, SEQ ID No. 40) encoding this fusion protein was constructed using standard molecular biology techniques and used to express the fusion protein in E. coli, as described above. This fusion protein was purified from the E. coli extract using amylose resin to bind the maltose-binding protein portion of the fusion protein and then Ni-NTA resin to bind the hexahistidine tag.

To measure the affinity of the fusion protein for streptavidin, the fusion protein was immobilized on a biacore chip through the crosslinking of free amino groups in the fusion protein to the biacore chip. Buffer containing streptavidin was washed over the chip, allowing streptavidin to bind the immobilized fusion protein (FIG. 10B). This resulted in an increase in the biacore response units which are proportional to the amount of streptavidin adhering to the biacore chip.

Figure 10A:
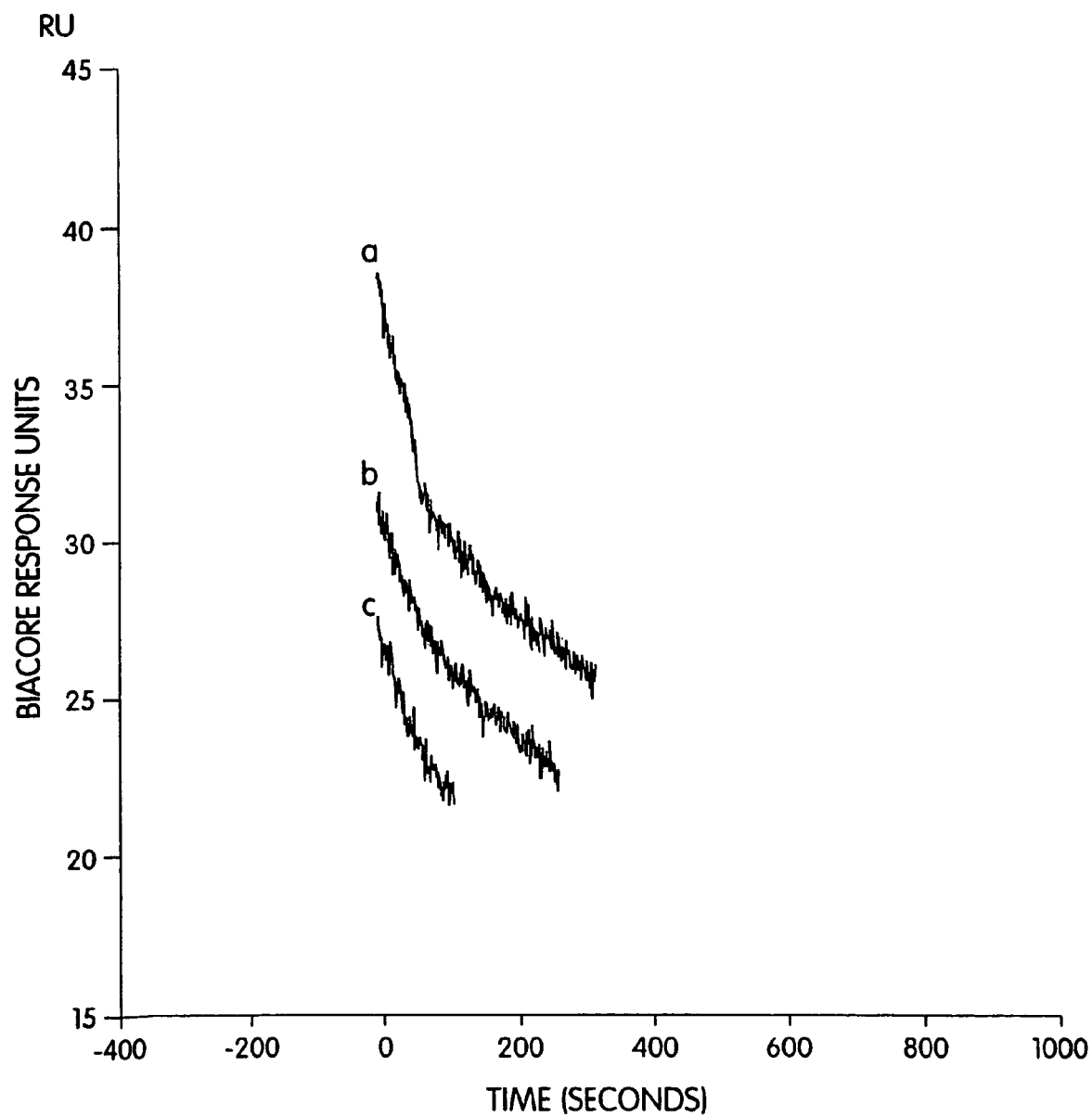
FIG. 10A is a graph of the Biacore (Surface Plasmon Resonance) response units over various lengths of time for the dissociation of streptavidin from the fusion protein listed in FIG. 9B immobilized on a biacore chip. For line "a," the streptavidin concentration is 23 µM; for line "b," the concentration is 11.5 µM, and for line "c," the concentration is 5.75 µM. This data was used to calculate an upper limit of $2 \times 10^{-3}/S$ for the dissociation rate, $K_D$
Figure 10B:
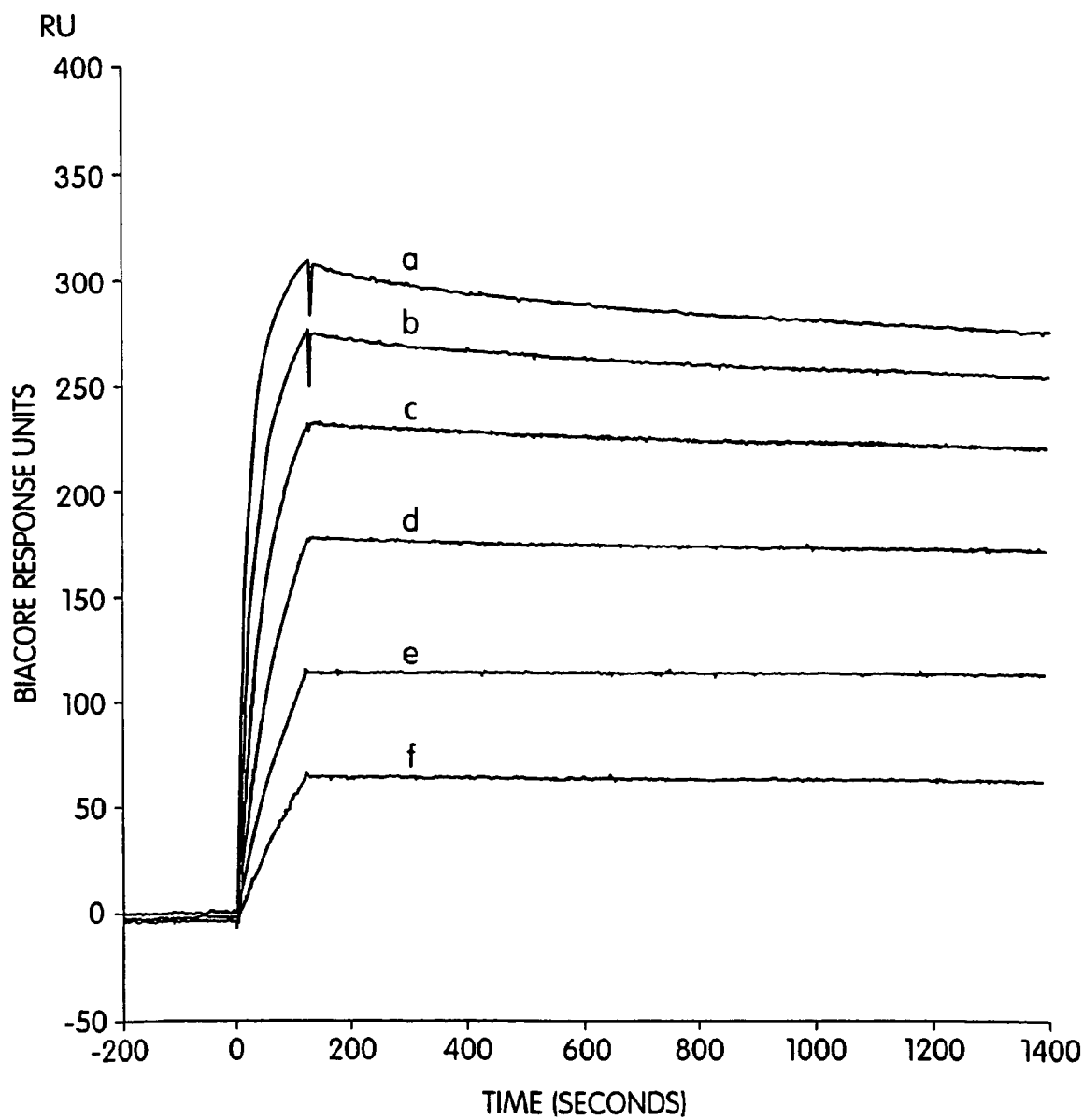
FIG. 10B is a graph showing the association and subsequent dissociation of streptavidin from the immobilized fusion protein. For lines "a" through "f," the streptavidin concentrations are 1.6, 0.8, 0.4, 0.2, 0.1, and 0.05 µM, respectively. This data was used to calculate an association rate, $k_a$, of $5 \times 10^4/M/s$.

Then buffer without streptavidin was washed over the chip, and the biacore response units decreased as streptavidin dissociated from the immobilized fusion protein (FIGS. 10A and 10B). To measure the association rate for the binding of streptavidin to the fusion protein, streptavidin concentrations of 1.6, 0.8, 0.4, 0.2, 0.1, or 0.05 μM, (lines "a" to "f" in FIG. 10B, respectively) were washed over the biacore chip. The buffer also contained 40 mM Tris(hydroxymethyl) aminomethane, 300 mM KCl, 2 mM EDTA, 0.1% w/v Triton X-100, and 5 mM 2-mercaptoethanol at pH 7.4. This data was used to calculate an association rate, $k_a$, of $5 \times 10^4$/M/s, as described previously (BIACORE X Instrument Handbook, version AA, Biacore AB, Uppsala Sweden, 1997). To measure the dissociation rate, a pulse of 23, 11.5, or 5.75 μM streptavidin in the buffer described above was administered, and then buffer without streptavidin was washed over the chip (FIG. 10A). This data was used to calculate an upper limit of $2 \times 10^{-3}$/S for the dissociation rate, $K_D$ (BIACORE X Instrument Handbook, supra). Based on these calculated association and dissociation rates, the dissociation constant, $K_D$, for the binding of streptavidin by this fusion protein was less than 40 nM. This result confirms the high affinity binding of the SB19-C4 peptide for streptavidin that was observed in the streptavidin column-binding assay and the EMSA assay (Table 1). Additionally, this result demonstrates that this peptide maintains its high affinity for streptavidin when expressed as part of a fusion protein.

Spin-Filter Binding Inhibition Assay Analysis of the Affinity of a Fusion Protein for Streptavidin To measure the $K_D$ of the peptide described above, a second and more general method, termed a Spin-filter Binding Inhibition Assay (SBIA), was also utilized. This method is especially appropriate for cases in which numerous proteins or peptides are derived from in vitro selection techniques using immobilized targets such as phage display (Smith, G. P. et al. *Chem. Rev.* 97:391–410, 1997), mRNA display (Roberts et al. *Proc. Natl. Acad. Sci.* USA 94:12297–12302, 1997; Liu et al. *Methods Enzymol.* 318: 268–293, 2000; Keefe et al. *Current Protocols in Molecular Biology* 2001; Keefe et al. *Nature* 410:715–718, 2001) or ribosome display (Jermutus et al. *Curr. Opin. Biotechnol.* 9:391–410, 1998). The principal benefit of this method is that it allows the affinities and specificities of interacting proteins to be assayed before investing the time required to over-express and purify them in the quantities required for conventional affinity determinations.

In general, SBIA utilizes low concentrations (<$K_D$) of $^{35}$S-labeled protein generated in a cell-free translation system. The labeled protein is exposed to the bead-immobilized target (in this case immobilized streptavidin), and then the flow-through is collected by centrifugation in a 0.2 μm Durapore® spin-filter. The fraction of counts that pass through the filter (and therefore did not bind to the column) indicates the fraction of labeled peptide that did not bind to the matrix. To determine the affinity of the interaction, the labeled protein is first exposed to a range of concentrations of non-immobilized target. After this mixture has reached equilibrium, it is briefly (1 minute) exposed to the bead-immobilized target, and then spin-filtered as above. The initial incubation with the soluble target will compete with the binding of the radio-labeled protein to the immobilized target. The amount of inhibition is directly related to the fraction of labeled protein that was bound to the free target before this mixture was exposed to the immobilized target. By plotting the immobilized target-binding inhibition against the concentration of the free target, the $K_D$ can easily be derived.

Because this titration is based on the interaction of the protein with the free (not immobilized) target, it may be more accurate than methods that quantify peptide binding to immobilized targets. However, SBIA may underestimate the affinity if there is significant dissociation of the complex during the brief incubation with immobilized target. The $K_D$ corresponds to the concentration of free target that half-inhibits the binding to the immobilized target. As long as the concentration of the labeled binder is significantly lower than the $K_D$, the concentration of free target may be approximated as the total concentration of added target. This method may be generally useful for the determination of $K_D$ values for protein-protein, protein-peptide, and protein-small molecule complexes.

To measure the $K_D$ of the SB19-C4 peptide, this peptide was fused to a FLAG-tag (streptavidin binding peptide-FLAG) (Wilson et al. *Proc. Natl. Acad. Sci.* USA 98:3750–3755, 2001). Streptavidin binding peptide-FLAG was then translated in the presence of $^{35}$S-labeled methionine by in vitro translation in reticulocyte lysate according to the manufacturer's instructions (Red Nova, Novagen, Madison, Wis.) using a template concentration of 400 nM, 1 mM extra $MgCl_2$ and 100 mM extra KCl. This mixture was then purified successively upon the basis of the FLAG-tag and then the His-tag (using the manufacturer's instructions; denaturing conditions were used for the Ni-NTA purification). The resultant purified peptide was then dialyzed into streptavidin-binding buffer (SBB: 300 mM KCl, 40 mM Tris(hydroxymethyl) amino methane, 5 mM 2-mercaptoethanol, 2 mM EDTA, 0.1% Triton-X 100, pH 7.4). The peptide was then diluted into the same buffer and mixed with a range of different streptavidin concentrations to give a set of 50 μl samples in which the SB19-FLAG peptide was at 200 pM and the streptavidin concentration ranged from 30 pM to 1 μM. Each of these samples was then incubated for 2 hours at 0° C. and then subsequently incubated for 1 minute with 10 μl samples of the washed and dried immobilized streptavidin matrix (Ultralink Immobilized Streptavidin Plus, Pierce, Rockford Ill.). The flow-throughs were then immediately collected by centrifugation in a 0.2 μm Durapore® spin-filter (Millipore, Bedford Mass.), and these were counted in a scintillation counter. These data were iteratively fitted to the following equation $y=b+c(K_D/(K_D+x))$ in which y was the number of radioactive decompositions detected per minute in each flow-through, $K_D$ is the dissociation constant of the complex, x was the concentration of free streptavidin, b was the number of counts per minute not competent to bind the matrix under the assay conditions, and c was the number of counts per minute competent to bind the matrix under the assay conditions. $K_D$, b, and c were iteratively determined using the program Deltagraph 4.0 (SPSS, Chicago Ill.).

Figure 12:
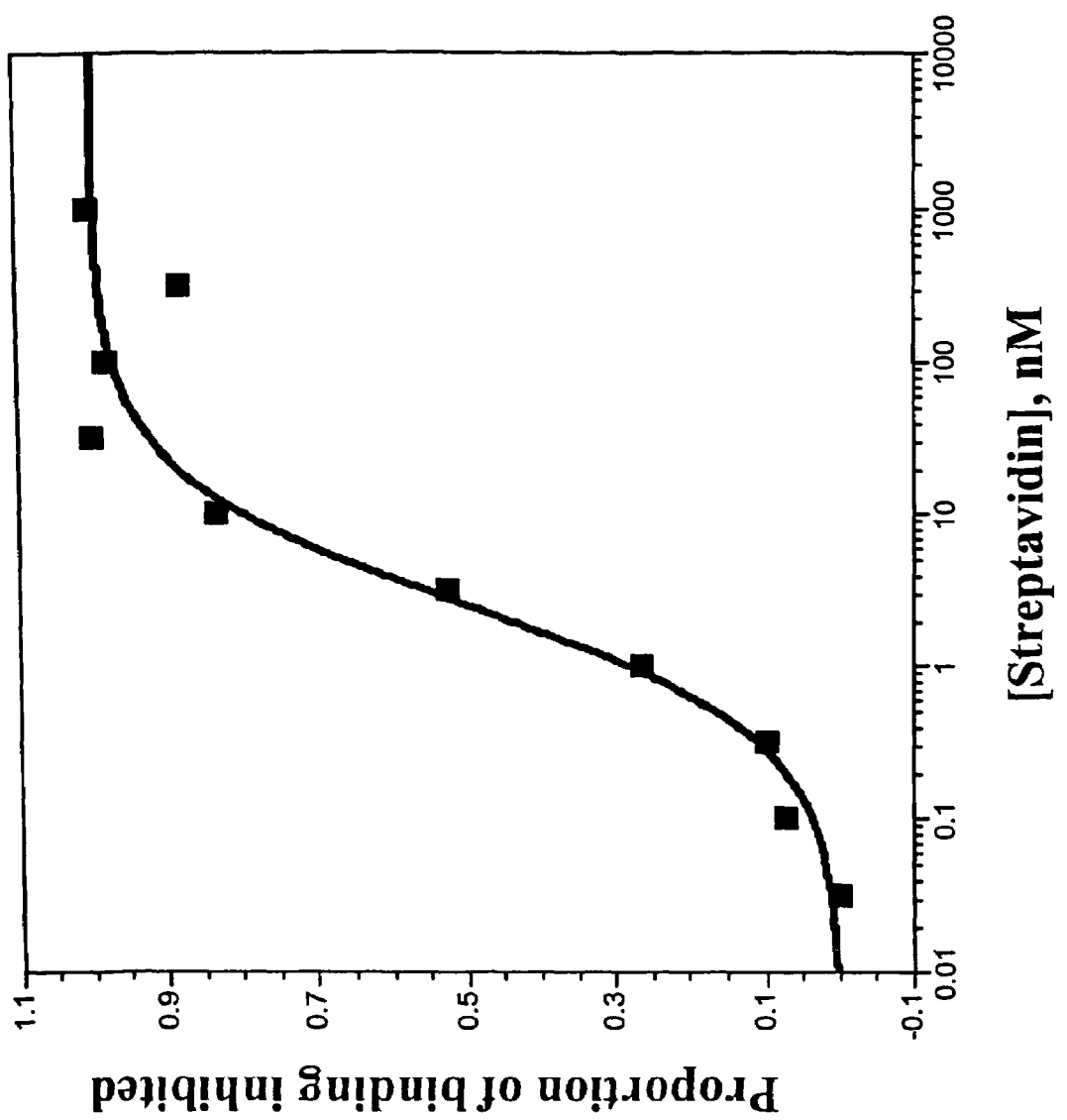
FIG. 12 is a graph showing a $K_D$ determination of the streptavidin binding peptides-streptavidin interaction using the Spin-filter Binding Inhibition Assay (SBIA). The labeled streptavidin binding peptide-tagged peptide was incubated with a range of streptavidin concentrations and the amount not complexed was then determined after a short incubation with immobilized streptavidin. This analysis gave a $K_D$ of 2.5 nM for the interaction of the streptavidin binding peptide sequence with streptavidin.
Figure 15:
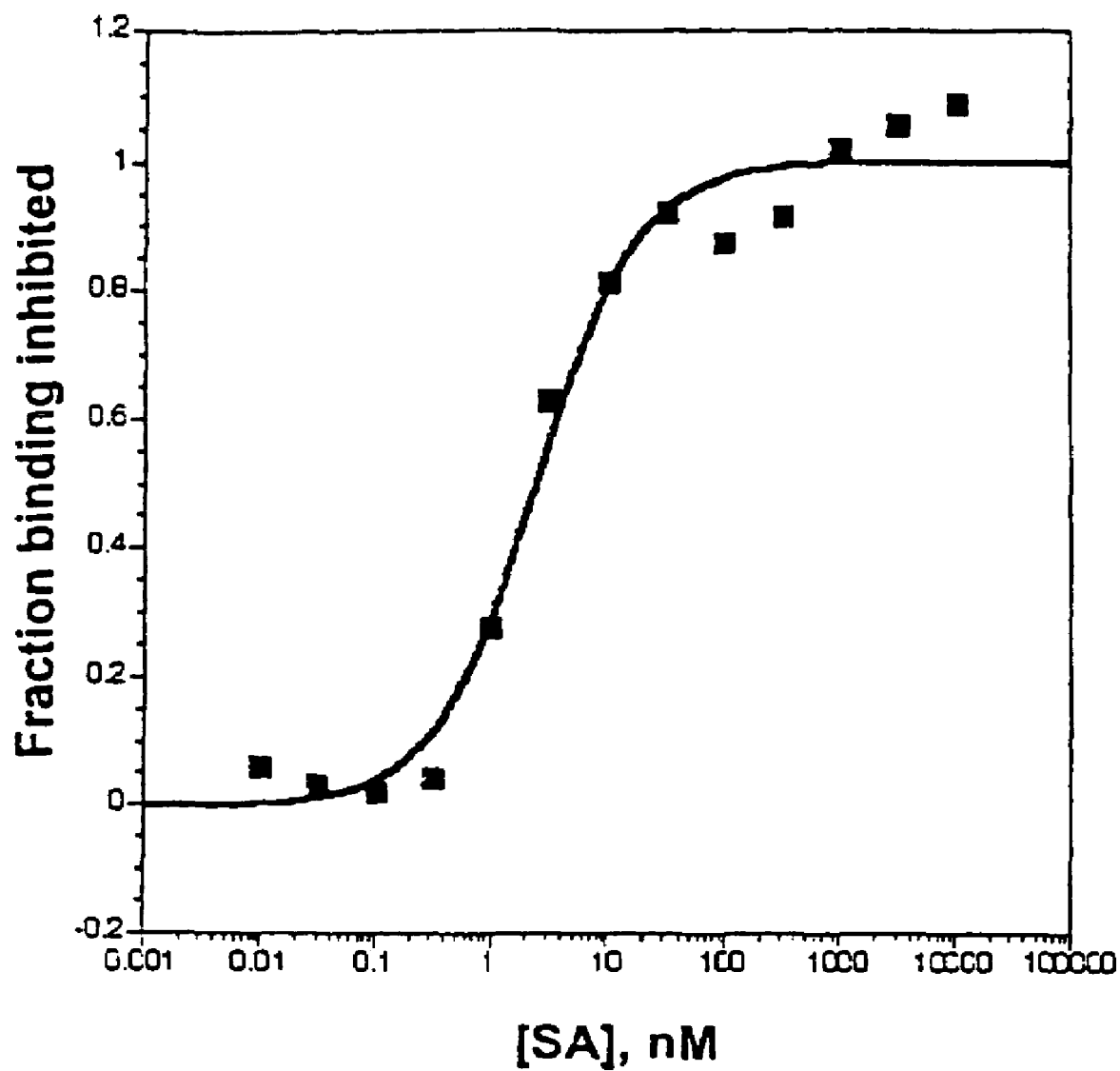
FIG. 15 is a graph showing a $K_D$ determination of a streptavidin binding peptide-streptavidin interaction. The y axis shows the fraction of surface-bound peptide that is competed by the free streptavidin. This analysis gave a $K_D$ of 2.4 nM for the interaction of the streptavidin binding peptide sequence with streptavidin.

In this experiment, the binding of labeled streptavidin binding peptide-tagged peptide was inhibited by pre-incubation with free streptavidin (FIG. 12). In this experiment 48% of the counts bound to immobilized streptavidin in the 1 minute slurry incubation in the absence of free streptavidin competitor, and this binding was completely inhibited by high concentrations (>100 nM) of streptavidin. Analysis of the binding curve gave a $K_D$ of 2.5 nM, which compared very favorably with the $K_D$ determined by other methods. For example, the same peptide was purified on a FLAG-affinity matrix, then bound to streptavidin immobilized on a microtiter plate. The labeled streptavidin binding peptide-tagged peptide was incubated with a range of streptavidin concentrations for 1 hour before being transferred to a streptavidin-coated plate and incubated for five minutes. The labeled peptide not bound to the plate was pipetted off. The binding affinity was measured by competition with varying concentrations of streptavidin. Analysis of the binding curve gave a Kd of 2.4+/−0.1 nM. (FIG. 15)(2.4 nM; Wilson et al. *Proc. Natl. Acad. Sci.* USA 98:3750–3755, 2001). The streptavidin binding peptide-tag therefore bound to streptavidin with a ~5,000-fold higher affinity than does the Strep-tag II (Schmidt et al. *J. Mol. Biol.* 255:753–66, 1996). This higher affinity accounts for the fact that, after extensive washing (with 80 column volumes), the yield of retained peptide using the streptavidin binding peptide-tag was 2,200-fold higher than the yield using the Strep-tag II (Wilson et al. *Proc. Natl. Acad. Sci.* USA 98:3750–3755, 2001). Both the streptavidin binding peptide-tag and the Strep-tag II contain the tripeptide motif HPQ, but the flanking sequence in the streptavidin binding peptide-tag presumably provides additional favorable contacts with streptavidin.

Other Embodiments

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

What is claimed is:

1. A purified nucleic acid encoding a peptide that binds streptavidin with a dissociation constant less than 10 µM and comprises an amino acid sequence having at least 80% identity to the first 38 amino acids of SEQ ID NO:25, wherein said peptide is not disulfide bonded or cyclized.

2. A purified nucleic acid encoding a peptide that binds streptavidin with a dissociation constant less than 10 µM and comprises an amino acid sequence having at least 80% identity to the first 38 amino acids of SEQ ID NO:25, wherein the amino acid sequence of said peptide does not contain a Histidine-Proline-Glutamine (HPQ), Histidine-Proline-Methionine (HPM), Histidine-Proline-Asparagine (HPN), or Histidine-Glutamine-Proline (HQP) motif.

3. A purified nucleic acid encoding a peptide that binds streptavidin with a dissociation constant less than 23 nM and comprises an amino acid sequence having at least 80% identity to the first 38 amino acids of SEQ ID NO:25.

4. The nucleic acid of claim 1 or 2, wherein said dissociation constant is less than 5 µM.

5. The nucleic acid of claim 1 or 2, wherein said dissociation constant is less than 1 µM.

6. The nucleic acid of claim 5, wherein said dissociation constant is less than 100 nM.

7. The nucleic acid of claim 6, wherein said dissociation constant is less than 50 nM.

8. The nucleic acid of claim 3, wherein said dissociation constant is less than 10 nM.

9. The nucleic acid of claim 8, wherein said dissociation constant is less than 5 nM.

10. The nucleic acid of claim 1, wherein said peptide comprises an amino acid sequence having at least 90% sequence identity to the first 38 amino acids of SEQ ID NO:25.

11. The nucleic acid of claim 10, wherein said peptide comprises an amino acid sequence having at least 95% sequence identity to the first 38 amino acids of SEQ ID NO:25.

12. The nucleic acid of claim 11, wherein said peptide comprises the amino acid sequence of at least the first 38 amino acids of SEQ ID NO:25.

13. The nucleic acid of claim 2, wherein said peptide comprises an amino acid sequence having at least 90% sequence identity to the first 38 amino acids of SEQ ID NO:25.

14. The nucleic acid of claim 2, wherein said peptide comprises an amino acid sequence having at least 95% sequence identity to the first 38 amino acids of SEQ ID NO:25.

15. The nucleic acid of claim 3, wherein said peptide comprises an amino acid sequence having at least 90% sequence identity to the first 38 amino acids of SEQ ID NO:25.

16. The nucleic acid of claim 3, wherein said peptide comprises an amino acid sequence having at least 95% sequence identity to the first 38 amino acids of SEQ ID NO:25.

17. A vector comprising a nucleic acid of any of claims 1–3.

18. A nucleic acid encoding a fusion protein comprising a protein of interest covalently linked to:
  (a) a peptide which binds streptavidin with a dissociation constant less than 10 μM and comprises an amino acid sequence having at least 80% identity to the first 38 amino acids of SEQ ID NO:25, wherein said peptide is not disulfide bonded or cyclized;
  (b) a peptide which binds streptavidin with a dissociation constant less than 10 μM and comprises an amino acid sequence having at least 80% identity to the first 38 amino acids of SEQ ID NO:25, wherein said peptide does not contain an HPQ, HPM, HPN, or HQP motif; or
  (c) a peptide which binds streptavidin with a dissociation constant less than 23 nM and comprises an amino acid sequence having at least 80% identity to the first 38 amino acids of SEQ ID NO:25.

19. The nucleic acid of claim 18, wherein said peptide is attached to the amino terminus or the carboxy terminus of said protein of interest, or wherein said peptide is positioned between the amino and carboxy termini of said protein of interest.

20. The nucleic acid of claim 18, wherein said peptide is linked to said protein of interest by a linker comprising a protease-sensitive site.

21. The nucleic acid of claim 18, wherein said peptide of (a), (b), or (c) comprises an amino acid sequence having at least 90% sequence identity to the first 38 amino acids of SEQ ID NO:25.

22. The nucleic acid of claim 21, wherein said peptide of (a), (b), or (c) comprises an amino acid sequence having at least 95% sequence identity to the first 38 amino acids of SEQ ID NO:25.

23. The nucleic acid of claim 22, wherein said peptide of (a), (b), or (c) comprises the amino acid sequence of the first 38 amino acids of SEQ ID NO:25.

24. A vector comprising a nucleic acid of claim 18.

25. A method of producing a streptavidin-binding fusion protein, said method comprising the steps of:
  (a) expressing in a host cell, a gene encoding a fusion protein of claim 18; and
  (b) culturing said host cell under conditions appropriate for production of said fusion protein; and
  (c) purifying said fusion protein from said cell.

* * * * *

UNITED STATES PATENT AND TRADEMARK OFFICE
CERTIFICATE OF CORRECTION

PATENT NO. : 7,138,253 B2  Page 1 of 1
APPLICATION NO. : 10/975582
DATED : November 21, 2006
INVENTOR(S) : Szostak et al.

It is certified that error appears in the above-identified patent and that said Letters Patent is hereby corrected as shown below:

Column 4, Line 1, replace "coumpound" with --compound--.

Column 23, Line 7, replace "Kd" with --$K_D$--.

Signed and Sealed this

Third Day of July, 2007

JON W. DUDAS
*Director of the United States Patent and Trademark Office*

UNITED STATES PATENT AND TRADEMARK OFFICE
CERTIFICATE OF CORRECTION

PATENT NO.       : 7,138,253 B2
APPLICATION NO.  : 10/975582
DATED            : November 21, 2006
INVENTOR(S)      : Szostak et al.

It is certified that error appears in the above-identified patent and that said Letters Patent is hereby corrected as shown below:

Delete drawing sheets 1-17, and substitute therfor drawing sheets 1-22. (attached)

Signed and Sealed this

Fourth Day of December, 2007

JON W. DUDAS
*Director of the United States Patent and Trademark Office*

| name | # | | SEQ ID NO: |
|---|---|---|---|
| SB1 | 3 | MDEKTHCTISMNGAVPLVPHHRPQGDLRLLHRPQPALLVRHHPQGDLVALVEHHEGVDRGLVALPELHAEELGEPVGDLVQGPVEQVQGRVVDALVWRLPPS | 1 |
| SB2 | 2 | MDEKTHCFHRGDHLVRLVEELQALAEGLQRQGGRQPHRLPRRRPHHLQLLLDEAHPQAGPLRERAHQVDGRLLLQHHPQGDHPLRLVWRLPPS | 2 |
| SB3 | 4 | MTRRPTASSSSCVRHLLRQGEHGHQALEDRDKARHRHVRLVEGDVEVLGGLDLRARARHEALHPQAGLVHLPLHGGDLRLVLRAAHPQGDRLGLAVHHH | 3 |
| SB4 | 1 | MDEKTHWGISTWRGEPLLHHEPQAGRLPLDRRARHRRLLGAEPGGWDHGLRLELLDDHRPLVPDHRPQRGPLQRGDLPQVVPLVRLRHAHVLGLGLAAATTT | 4 |
| SB5 | 3 | MDEKTHWANVYHPQGDLLVRGHGHDVRALHDQGLHQLLLDLLVPPEEVVRALRGEVLGGLRRLVPLDEPQGERALDQARQRPQHLLELHHRALPPALLVWRLPPS | 5 |
| SB6 | 1 | MDEKTHWLANPFEELLARLDGLREGEDHPLVLHEHPQGDLLGRHRALDGEVREGDRPLDQGGEEDLGALVDDGEVLDGLVANGVHVHDPLVCGCHHH | 6 |
| SB7 | 1 | MDEKTHWFGTLNSFPTHWMSAVGNGKIDCSFNNMLSLNHWLSSGHPDGALLDDQPLGRHRALDDGEVREGDRPLDQGGEEDLGALVDDDGEVLDGLVANGVHVHDPLVCGCHHH | 7 |
| SB8 | 1 | MDEKTHWFGTLNSFFTHWKLHHHPQGDALLDDGVRPHHPLADEGGGLDQGLGHRRGVVAERLARRDPEVLEGLVERHRGLVPRLRNGGERHAEPLVWRLPPS | 8 |
| SB9 | 1 | MDEKTHCNTGLYDGAADCFNELNKDVAPLVEGRHDLVEGLLLRHHEGDPLVAHRQLVHHPLLGRERHRRALVPQQEHQPHRLQPVVDLGRRRLVWRLPPS | 9 |
| SB10 | 1 | MDEKTHWHERAQELVGGLLLHDHPQRLLLEPRGPRLRGLVHERGHQPQPLAGRVEEADGGLLRDQGGELEPLVREGEDHLRPLDDELDAGRGLVWRLPHHH | 10 |
| SB11 | 1 | MDEKTPHWHERVHHLADGLEQHPQGQRRPLVERHRQVPRGLVRELQHRGEPLEHPAGVHVTRLHQGDDRDVDEGLVDHGRDVRGLERRVGDGPHRLVWRLPPS | 11 |
| SB12 | 4 | MDKDPLLEELEELRERLVHHPGGLLPLRGQVGHDAERLGAEVDDLRGGLLDEPQRAVAGLHHVPRHVGQRLVHEVRELDEGLLDQRDDLRQLVWRLPPS | 12 |
| SB13 | 2 | MEREDPLDEQLRELREALVDHFPQGGAQALHRHDGGEEHVPLRRVQHRLQPGLQHLEFQPLGLLGELQARLQPLAGEHHEGDCAGLQRVPGHQGRRLVWRLPPS | 13 |
| SB14 | 1 | MDEKFERTLSVSLSFNDWLAGQTKACWRLVEGGLHGHPQGLVREHEVDVLPLAEEVQQVVGGLADGVREQPFGGGLLHRAQRVDHPLPDHAGQVLGRLVWRLPPS | 14 |
| SB15 | 1 | MDEKTHWLEDLKGVLKDCLKDLMDFTKDCRSPRVQPQPLLHHDRGEPVLPLLHEAGRDLGGLGPRAPRKQARPLHHGRHDLHEPLVLQDHPQGGPLVCGCHHH | 15 |
| SB16 | 1 | MDEKTHWVLQLHPQGRELGPRHGGDDVRLVGQGEGVLEGLDGRPRRRHRLPREDEHRVRALVDQVRDLAERLVEEVDGGVRALRHLGLPQDEPRSGGCHHH | 16 |
| SB17 | 2 | MDEKTHWVGDLQEPLGPLHGGVEVPGGIVLRHHPQRDRLVDGVPHRGALARRPHRVVEGLHHLLQRGGERLPPDGPRQLGLLGGELDRADPALVWRLPPS | 17 |
| SB18 | 1 | MDEKTHCAVANWVGLTFWCHRVAHLQPLDPHPQGGDHRLRLEPLGHALVDPLVGGVEEVVRPLQLDVGVQDRVALVEQVARVGEGLDHEACQAHGALVWRLPPS | 18 |
| SB19 | 1 | MDEKTFGWRGCHVVEGLAGELEQLRARLEHHPQGGQRPLVQEVEDVDEGLVQDLHGVVAGLLDPVEKLLTDWFKKFKNVSKDCKMTFYLEMYDWSGGCHHH | 19 |
| SB20 | 1 | MNEKTHCKLNPFKVNIADWLAEFHGGGQGLLGRRDGSVVQRLVDGVQERVERLRDPGLGDLRLELHHRDHRLRLGGEHLLRDHPLEPDDHLVGGLVWRLPPS | 20 |

Fig. 3

```
                                                                        % binding  SEQ ID NO:
F1  MDEKTTGWRGGHVVEGLAGELEQLRARLEHHPQGQREPLVQEVEDVDEGLVQDLHGVVAGLLDPVEKLLTDWFKKFKNVSKDCKMTFYLEMYDWSGGCKLG  85  21
C1  MDEKTTGWRGGHVVEGLAGELEQLRARLEHHPQGQREPLVQEVEDVDEGLVQDLHGVVAGLLDPVEKLLTDWFKKFKNVS              87  22
C2  MDEKTTGWRGGHVVEGLAGELEQLRARLEHHPQGQREPLVQEVEDVDEGLVQDLHGVVAGLLDPVE                           88  23
C3  MDEKTTGWRGGHVVEGLAGELEQLRARLEHHPQGQREPLVQEVEDVDEGLVQ                                          89  24
C4  MDEKTTGWRGGHVVEGLAGELEQLRARLEHHPQGQREPLVQEVEDVDEGLVQ                           MMSGGCKLG     88  25
M1  MDEKTTGWRGGHVVEGLAGELEQLRARLEHHPQGQREP                                         MMSGGCKLG     69  26
N1  MDEKTTGWRGGHVVEGLAGELEQLRARLEHHPQGQREP                                         MMSGGCKLG  0.065  27
M2  MD                GHVVEGLAGELEQLRARLEHHPQGQREP                                 MMSGGCKLG     30  28
N2  MD                 EGLAGELEQLRARLEHHPQGQREPLVQEVEDVDEGLVQDLHGVVAGLLDPVEKLLTDWFKKFKNVSKDCKMTFYLEMYDWSGGCKLG  0.058  29
N3  M                  ELEQLRARLEHHPQGQREP                                                     
```

Fig. 5

(SEQ ID No.: 37)

```
ATCCGGATATAGTTCCTCCTTTCAGCAAAAAACCCCTCAAGACCCCGTTTAGAGGCCCCAAGGGGTTATGCTAGTTATTGC
TCAGCGGTGGCAGCAGCCAACTCAGCTTCCTTTCGGCTTGTTGTTAGCAGCCGGATCTCAGTGGTGGTGTGGTGCTC
GAGTGCGGCCCGCAAGCTTTAGTCGTCATGATGAAGTGTCTCCCCCGATATCAATGCTATTGTTAAAGCAGGTCT
TACACATGTTATAGATCCTCAAATGCTTGTCTTCACCTTCCGGGAGCCACCTTGCATTCACACAAGGTCC
ATGCTACCTCGGGGTACCAAGAATTCGTGATGATGGTGACCAGTCCTTCAACAACGTGTCCAACCAGTGTCTTCT
CTCCAGTCGTGCACGAAGTTGTTCAAGTTCCCCAGCTCGAATTAGTCTGCGCGTCTTTCAGGGCTTCATCGACAGTCTGACGACCG
CGTCCATCCTGAGCCGCTACCTCCTGAGCTCGAATACGCACGGCATACCAGAAAAGCGGACATCTGCGGGATGTTCGGCATGATTTCACCTTT
CTGGCGGCGTTGATCACCGCAGTAGTGGCGCCAATACGTGGATCTTCGCCAACTTCAGCGTTTCGAGGAACTCTTTGCCAGCTCTTTG
GCGGGTTTGTCTTTATTAACCGCTTCCAGACCTTTCATCAGTCAGCAGATAGTTTCGATGGTTTGACCCTGAAGGTCGGCAGTAC
TTCGACTGGCGCGTTAATACCTGCGCTCAGCACCGCCAACGAACGTTTGATGGTTGACCCCTTGACCATCGCTGTTTCGCCTT
CGTTACACCATAATTCACTTTGCTGGTGTCGATGGAGTAATCGGTCTGCATTCATTCATGTGTTGTACTTGCCGTTTCATACTGAACGCATAACC
TATTAAAGGCAGCTTTCGCGCCAGCGTTATCGGCCAGTGAAGTACGGTTCTTGCAGTTGAACATCAGCGCCTCTTACCTTTCGTTTCA
AGACCCGTCAGCAGCAATCAGCGCCGGGATCTCTTCCAGGTTTTTGGCGGGTTCGGCAGCAGATCTTTGTTATAAATCAGCGATAAC
GTTCTTTATCCAGCGCCGGTAAGCAATCAGCTTGCCGTTGTAACGTACGGCATCCAGTTGTAAACGGATACAGCTTGTCCTG
GCTTCAACAGCGATCGGTAAGGGGTGATTTCAGCCAACCTGTGGGAATTTCTCTTCCAGTTTATCCGGATGCTCAACGGTGACTTTAATT
GAACGCTTTGTCCGGGGTGATTTGCCGCAACCTGTGCCGGAATTCTTACGCCGAGACCGTTATAGCCTTTATCGCCGTTAATCCAGATTACCAGTTT
TGTCAGGGCCATCGCCAGTTGCCGCAATTCTTACCGACTTCAGCGAGACCGTTATAGCCTTTATCGCCGTTAATCCAGATTACCAGTTT
CCGGTATCTTTCGATTCCCATGGTAGTCGTATTATTAATTCGCGGATCGAGATCTGATCCTCTACCGCGATGGGAAGATCGGGCTGCGCACTTCGGCT
ACCTTCTTTCGATTCCCATGGTAGTCGTATTAATTTCGCGGATCGAGATCTGATCCTCTACCGCGATGGGAAGATCGGGCTGCGCACTTCGGCT
AATTCCCGGCCACAGGTGCCGGTTCGGCGGTATGTGGCAGGCCCGTGGCGGGGACTGTTGGCCATCTCCTTGCATGCAC
ACCGGCGCCACAGGTGCCGGTTGCCGGGTATGTGGCAGGCCCGTGGCGGGGACTGTTGGCCCATCTCCTTGCATGGAG
CATGAGCGCTTTGTTTGCGGCGGTCTCAACGGCCCTCAACCTACTACGGTCCGGCTGTGTCCTAATGCAGGAGTCGCATAAGGAGAG
CATTCTTGCGGGCGGACACCATCCAGTAACCAGTTATACGATGTCGCAGAGATGTCCCGGTTCTCTTATCAGACCGTTTCCGCGTG
CGTCGAGATCCCGGACACCATCCAGTAACCAGTTATACGATGTCGCAGAGATGTCCCGGTTCTCTTATCAGACCGTTTCCGCGTG
GGGTGGTGAATGTGAAACCAGCCACGTTTCTGCGAAAAACGCCGGAAAAGTGAAGCGGCGATGGCGGAGCTGAATTACATTCCAA
GTAACCAGGCCACAACAACTGGCGGCAAACAGTCGTTGCTGATTGGCGTTGCCACCTCCAGTCTGCCACGCGCCGT
```

Fig. 6A

```
GCTCACGCTGTAGGTATCTCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCGAACCCGGTAAGACACGACTTATCGCCACTGGCAGCAGCCAC
TGGTAACAGAGATTAGCAGAGCGAGGTAGCGGTGCTACAGAGTTCTTGAAGTGGTGGCCTAACTACGGCTACACTA
GAAGGACAGTATTTGGTATCTGCGCTCTGCTGAAGCCAGTTACCTTCGGAAAAAGAGTTGGTAGCTCTTGATCCGGCAAA
CAAACCGCTGGTAGCGGTGGTTTTTTGTTTGCAAGCAGCAGATTACGCCAGAAAAAAGGATCTCAAGAAGATCC
TTTGATCTTTTCTACGGGGTCTGACGCTCAGTGGAACGAAAACTCACGTTAAGGGATTTTGGTCATGAACAATAAAACTG
TCTGCTTACATAATGGAGTCGATGCTGATTTATATGGAGTGTTATGAGCCATATTCAACGGGAAACGTCTTGCTCTAGGCCGGATTAAA
TTCCAACATGGATGCTGATTTATATGGGTATAAAATGGGCTCGGCGATAATGTCGGGCAATCAGGTGCGACAATCTATCGAT
TGTATGGGAAGCCCGATGCCGCCAGAGTTGTTTCTGAAACATGGCAAAGGTAGCGTTGCCAATGATGTTACAGATGAGATG
GTCAGACTAAACTGGCTGACGGAATTTATGCCCTCTTCCGACCATCAAGCATTTTATCCGTACTCCTGATGATGCATGTT
ACTCACCACTGCGATCCCCGGGAAAACAGCATTCGATTCGATTCCTGTTTGTAATTGTCCTTTTAACAGCGATCGCGTATTCGTCTC
CGCTGGCAGTGTTCCTGCGCCGGTTGCATTGAATAACGGTTTGGTTGATGCGAGTGATTTGATGACGAGCGTAATGGCTGGCCTGTTGA
GCTCAGGCGCAATCACGAATGAATAAACTTTTGCCATTCTCACCGGATTCAGTCGTCACTCATGGTGATTTCTCACTTGATA
ACAAGTCTGGAAAGAAATCACGAGGGAAATTAATAGGTTGTATTGATGTTGACGAGTCGGAATCGCAGACCGATACCAGGATCTT
ACCTTATTTTGACGAGGGAACTGCCTCGGTGAGTTTTCTCCTTCATTACAGAAACGGCTTTTTCAAAAATATGGTATTGATAATCC
GCCATCCTATGGAACTGCCTATGCAGTTTCATTTGATGCTCGATGAGTTTTCTAAGAATTAATTCATGAGCGGATACATATTTGAA
TGATATGAATAAATGCAGTTGCATTTGATGCTCGATGAGTTTCCGCACATTCCCCGAAAAGTGCCACCTGAAATTGTAAACGTTAATAT
TGTATTTAGAAAAATAAACAAATAAGGGTTCCGCGCACATTCATTTTTAAATCAGCTCATTTTAACCAATAGGCCGAAATCCCTTATA
TTTGTTAAATTCGCGTTAAATTTGTTAAATCAGCTCATTGTTCCAGTTGGAACAAGAGTCCACTATTAAAGAACGTGGACTCC
AATCAAAAGAATAGACCGAGATAGGGTTGAGTGTTGTTCCAGTTTGGAACAAGAGTCCACCATCACCCTAATCAAGTTTTTGGGTC
AACGTCAAAGGGCGAAAAACCGTCTATCAGGGCGATGCCGGGAAATAGACGGTTTAGAGCTTGACGGGGAAAGCCGGCGAACGTGG
GAGGTGCCGTAAAGCACTAAATCGGAACCCTAAAGGGAGCCCCCCGATTTAGAGCTTGACGGGGAAAGCCGGCGAACGTGG
CGAGAAAGGAAGGGAAGAAAGCGAAAGGAGCGGGCGCTAGGGCGCTGGCAAGTGTAGCGGTCACGCTGCGCGTAACCACC
ACACCCCGCCGCTTAATGCCGCCTACAGGGCGCGTCCCATTCGCCA
```

Fig. 6A (continued)

(SEQ ID No.:38)

MGIEEGKLVIWINGDKGYNGLAEVGKKFEKDTGIKVTVEHPDKLEEKFPQVAATGDGPDIIFWAHDRFGGYAQSGLLAEI
TPDKAFQDKLYPFTWDAVRYNGKLIAYPIAVEALSLIYNKDLLPNPPKTWEEIPALDKELKAKGKSALMFNLQEPYFTWP
LIAADGGYAFKYENGKYDIKDVGVDNAGAKAGLTFLVDLIKNKHMNADTDYSIAEAAFNKGETAMTINGPWAWSNIDTSK
VNYGVTVLPTFKGQPSKPFVGVLSAGINAASPNKELAKEFLENYLLTDEGLEAVNKDKPLGAVALKSYEEELAKDPRIAA
TMENAQKGEIMPNIPQMSAFWYAVRTAVINAASGRQTVDEALKDAQTNSSSGGSGSGMDEKTTGWRGGHVVEGLAGELEQ
LRARLEHHPQGQREPGSGHHHHHHEFLVPRGSMDPCVKCKVAPRNWKVKNKHLRIYNMCKTCFNNSIDIGDDTYHGHDD

Fig. 6B (SEQ ID No.:39)

MDPCVKCKVAPRNWKVKNKHLRIYNMCKTCFNNSIDIGDDTYHGHDD

Fig. 6C

MDEKTTGWRGGHVVEGLAGELEQLRARLEHHPQGQREP

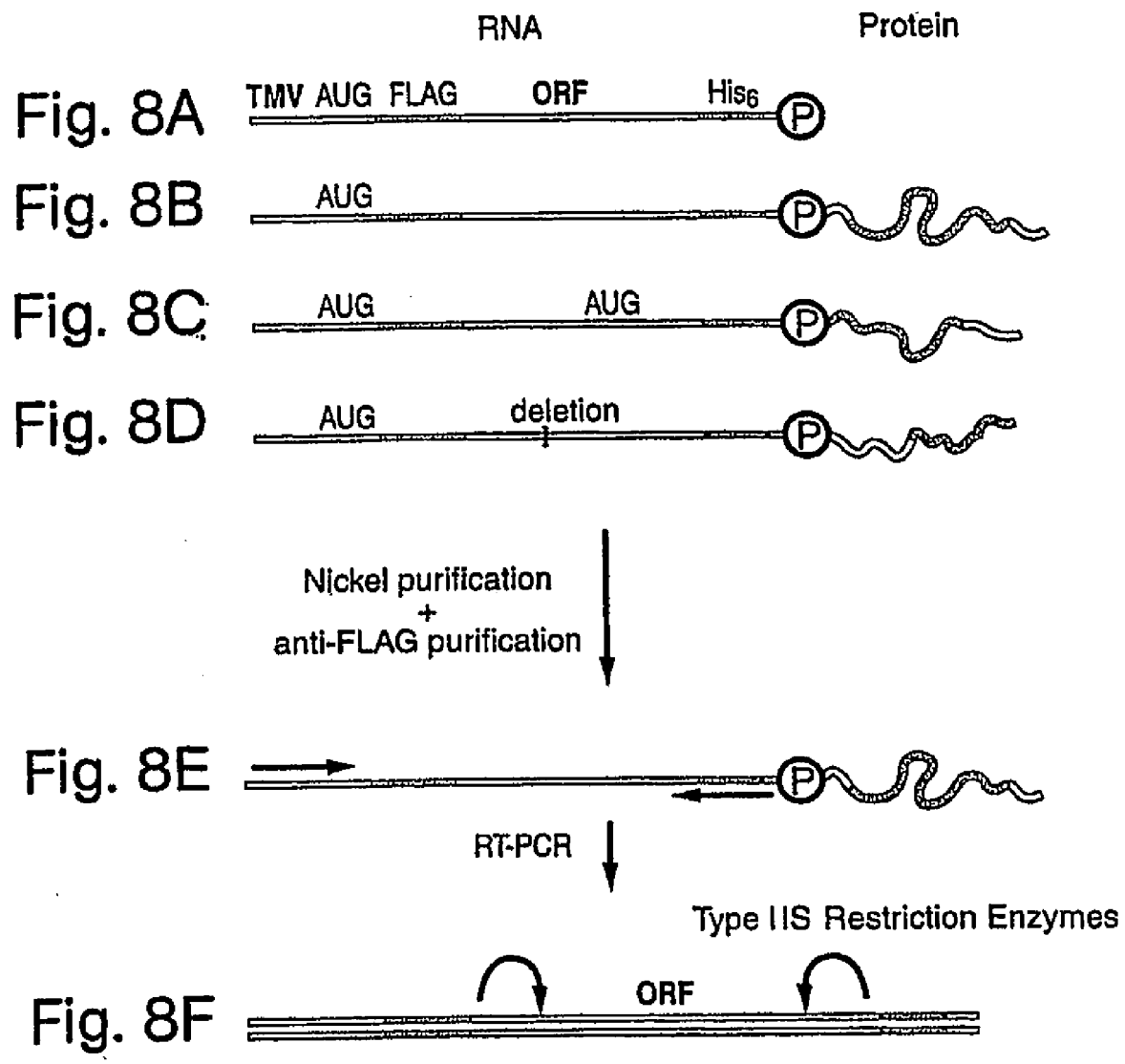

(SEQ ID No.:40)

ATCCGGATATAGTTCCTCCTTTCAGCAAAAACCCCTCAAGACCCGTTTAGAGGCCCCAAGGGGTTATGCTAGTTATTGC
TCAGGGTGGCAGCAGCCAACTCAGCTTCTTTCGGGCTTCTTGTTAGCAGCCGATTCAGTGGTGGTGGTGGTGGTGCTC
GAGTGCGGCCGCAAGCTTCAGCTGCGAAGCTTATTAGAATTCGTGATGATGGTGACCGGATCCTGGTTCACGTT
GACCTTGTGGGTGATGCTCCAGTCGTGCACGAAGTTGTTCAAGTTCCCAGCCAGTCCTTCAACGTGCCACCTCGC
CAACCAGTGGTCTTCTCGTTCCATCCCTGAGCCGTACCTCCTGAGCTCGACACGGCATACCAGAAAGCGACATCTGCAGGCTTCATC
GACAGTCTGACGACCGCTGGCGGCGTTGATCACCGCAGTACGACCAGCAATACGTGGATCTTTCGCCAACTCTTCCTCGTAAGACTTC
GCATGATTCACCTTCGTCTTGGGCGTTTGTCTTTATTAGTGGCGGCAATACCGGTTCATCAGCAGATAGTTTCGAGGAACTC
AGCGCTACGGCCAGCGGTTTGTCTTTATTAACCGCTTCAGACCTTCATCAGCAGAACGGTTTGGATGGTTGACCCT
TTTTGCCAGTCTCTTTGTTCGGACTGGCAGTTAATACCTTGCTGGGGCTTAATACCTTGCTGTGTGATGTTGGACATGCCACGGCCGTTGATGGTC
TGAAGGTCGGCAGTACCGTTATTAAAGGCAGCTTCGGCAGCCGCTTCCGCAGCAATCAGCTCTTTAATGTCGTACTGCCGTTTCAT
ATCGTGTTTCGCCTTTATTATGGAGCAGCTTCGCGCAGCAATCAGCGGCGTTATCCACCGCCACAGTCGTATCCGGTTAATCGTGTTTCAT
GTCAACCAGGAAGGTCAGACCCCGTTCGCGCAGCAATCAGCGCCGGGATCTCTTCCCAGGTGAAGTACGGTCTTGCAGGTTGAACATCAGCGCGCTC
ACTTGAACGCATAACCCCGTCAGTCTTTATCCAGCGCCGGGATCTTCTTCCCCAGGTTTTTGCCGTTCGCAGCAGATCTTTGTT
TTACCTTTCGCTTTCAGTTCTTTATCAACAGCGATAACGCTTCAACACGCGATGGGTAAGCAATCAGCTTGCCGTTGTAACGTACGGCATCCAGTAAACG
ATAAATCAGCGATAACGCTTCAACACGCGATGGGTAAGCAATCAGCTTGCCGTTGTAACGTACGGCATCCAGTAAACGGTCG
GATACAGCTTGTCCTGGAACGTTGTCCGGCCATCGCCAGTTGCCCAACCTGTGGGGAATTTCTCTTCCAGTTTATCCGATGCTC
TGTGCCCAGAAGATAATGTCAGGGCTATCTTCTGATTcccatgTATATCCCTCTTCTTAAGTTAAACAAAATTATTTCTAGAGGGA
AACGGTGACTTAATTCCGGTATCTTCTTCGATTcccatgTAGTGAGTCGTATTAATTCGCGGGATGAGATCTCGATCCTCTACGCCGGACG
TCCAGATTACCAGTTTACCTTCTCACAATTCCCCTATAGTGAGTCGTATTAATTCGCGCGCTATATCCGACATCACCGATGGGGAAGATCGGG
ATTGTTATCCGCTCACAATTCCCCTATAGTGAGTCGTATTAATTCGCGCGCTATATCCGACATCACCGATGGGGAAGATCGGG
CATCGTGGCCGGCATCAGCCGGACACCGCCATGCATGGGTATGGTCAGGCCCCGTGGCCGGGGACTGTTGGGCGCC
CTCGCCACTTCGGGCTCATGACCATTCCTTGCGGGCGTCGAGATCCCTGTTCGGCCGCGGTGCAGGCTGGCTGCTTCCTAATGCAGGA
ATCTCCTTGCATGCACCATTCCTTGCGGGCGTCGAGATCCCTGGAACATCCGGCAAATCCTTCGCGGTATGGCATGATGAGCCCG
GTCGCATAAGGCGAGAGCGTCGAGATCCCGGAACATCCGGCAAATCCTTCGCGGTATGGCATGATGAGCCCG
GAAGAGAGTCAATTCAGGGTGGTGAATGTGAAACCAGTTATACGATGTCGCAGAGTATGCCGGTGTCTCTTATCA
GACCGTTCCGGTGGTGAACCAGCCAGCGCCCACGTCTTCTGCGAAAACGCGGGAAAAGTGGAAGCGGGCGATGCGGAGC
TGAATTACATTCCCAACGCGTGGCACAACAACTGCGGGCGATTAAATCTCGCGCAAACAGTCGTTGCGATTGGCGTTGGTGTCTG
GCCCTGCACGCGCCGTCGCCGCAAATTGTCGCGGCGATTAAATCTCGCGCAACAGCCGTTGCGATTGGCGGTGTCTG
GGTAGAACGAAGCGGTCGAAGCCTGTCACAATCTTCTCGCCAACGCCGGTGCAACGCCGTCAGTGGGCGTGATCATTA

Fig. 9A

```
ACTATCCGCTGGATGACCAGGATGCCATTGCTGTGGAAGCTGCCTGCACTAATGTTCCGGCGTTATTTCTTGATGTCTCT
GACCAGACACCCATCAACAGTATTATTTCTCCATGAAGACGGTACGCGACTGGGCGTCTGGAGCATCTGTTCGCATTGGG
TCACCAGCAAATCGCGCTCTGTTAGCCGGCCCATTAAGTTCTGTCTCGCGGCGTCTGCCTGCGTCTGGCTGCTGGCATAAATATC
TCACTCGCAATCAAATTCAGCCGATAGCGGAACGGAAGGCGACTGGAGTGCCATGTCCGGTTTCAACAAACCATGCAA
ATGCTGAATGAGGGCATCGTTCCCACTGCGATCGTCGGTGCCAAGATCAGATGCGAAGACAGCTCATGTTATATCCGC
CGAGTCCGGCGTTGGTGCCGTTCGCGATATCTCGGATACGAGCGTGGACCGCTTGCTGCAACTCTCTCAGGCCAG
CGTTAACCACCATCAAACAGGATTTTCGCCTGCTGGGCAAACCAGCTGACCACCCTGGCGCCCAATACGCAAACCGCCTC
GCGGGTGAAGGGCAATCAGCTGTTGCCCGGTCACTGGTGAAAAGAAACCACCCTGGCGAAAGCGGCAGTGAGCGCAACGCA
TCCCCGCGCGTTGGCGATTCATTAATGCAGCTGGCACGGATCTCGACGAGGTTCCCGACTGAAAGCGCGTTCAACCGCAGTCCTT
ATTAATGTAAGTTAGCTCACTCATTAGGCACCGGGATCGCGCCACTTATGACTGTCTTCTTTATCATGCAACTCGTAGGACAGGTCCGG
CCGGTGGGCGCGGGGCATGACTATCGCCGCACGCTTTTCGGAGGCGACGATGATCGGCCTGTCGCTTGCGTTATTCGA
CAGCGCTCTGGGTCATTTCGCTCAAGCCTTCGTCACTGGTCCCGCCACCAAACGTTCGGCGAGAAGCAGGCCATTATCGCCGG
ATCTTGCACGCCCCTCGCTCACGGGTGCCATGATCGTGCCAGCCAGCCGGCTAGGCTGGGCGGGTTGCCTTACTGGTT
CATGGCGGCCCCACGGGTGCCGATACGGAGCGAACGTGAAGCGAACTGCTCTGCAAAACGTCTGCGACCGAGCAACAACATGA
AGCAGAATGAATCACCGATACGCGAGCGAAGCTGAAGTCTGGTAAAGTCTGGAACGCGGAAGTCAGCGCCCTGCGAAGTCAGCGCCCTGCACCATTATGTTCCGGATCTGCAT
ATGGTCTTCGGTTTCCGTGTTTCGTAAAGTCTGGAACACCTACATCTGATTAACGAAGCGCTGCATTGACCCTGAGTGATTTTC
CGCAGGATGCTGCTGGCTACCCTGTGGAACGCCAGTTGTTTACCCTCACACGTTCCAGTAACAGACAGAAATCCCCTTACACGAGGCATCAGT
TCTGGTCCCGCCGCATCCATACCGCTCGTTTCATCGGTATCATTAACATGCCCGTTATCAGAACGTTCAGTGCCAGCTGCCTGCG
CGTATCGTGAGCAGTTCATGCGGATCGAAACCCCCTTATCGTGAATCGCTTCAGCAGTCTGTTGCGGGCAGCCATGAGCTTTACGGATGCCGGT
GACCAAACAGGAAAAAACCGCTCAGTGATGACGACGGTCACAGCTTCCAGTGAAGTCACACGTCCAGATGCCGGCGATA
AGCTGCGGATGATGACGTCAGGGCGTCAGGGCGCGTCAGGGCGCGTCAGGGGCGCGCGTGGCAGCAGATCTGTGACACAGGGGGCTGGATGCCGGG
CGTTTCCGTGATGACGATGACGTCAGGGCGTGATGAACAGGCAGACGAATCGCTGAATCGCTTGAATGCTTCACGTTCCTGCAGCTGCCTCGCG
AGCAGACAAGCCCGTCAGGGGCGTTAACTATGCCAGGCGCATCAGCAGCGCCTTCCGCCCTTCCTCGCTGCTCACTGACTCGCTGCCTCGGTCTTC
GCGGAGTGTATACTGCTTAACTATGCCATCAGGCGCATCAGCAGCGCCTTCCGCCCTTCCTCGCTGCTCACTGACTCGCTGCCTCGGTCTTC
GCACAGATGCGTAAGGAGAAAATACCGCATCAAGGCGCTCTTCCGCTCCTTATCCACAGAATCAGGGGATAACGCAGGAAAGAAC
GGCTGCGGCGAGCGGTATCAGCTCACTCAAAGGCGGTAATACGGTTATCCACAGAATCAGGGGATAACGCAGGAAAGAAC
ATGTGAGCAAAAGGCCAGCAAAGGCCAGGAACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGACAGGACTATAAAGATACCAGGCGTTTCCCC
CTGGAAGCTCCCTCGTGCGCTCTCCTGTTCCGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTGAGTCCAACCCGGTAAGACACGACTTATCGC
```

Fig. 9A (continued)

```
CACTGGCAGCAGCCACTGGTAACAGGATTAGCAGAGCGGAGGTATGTAGGCGGTGCTACAGAGTTCTTGAAGTGGTGGCCT
AACTACGGCTACACTAGAAGGACAGTATTGGTATCTGCGCTCTGCTGAAGCCAGTTACCTTCGGAAAAAGAGTTGGTAG
CTCTTGATCCGCAAACAAACCACCGCTGGTAGCGGTGTTTTTGTTGCAAGCAGCAGATTACGCGCAGAAAAAAG
GATCTCAAGAAGATCCTTTGATCTTTTCTACGGGTCTGACGCTCAGTGGAACGAAAACTCACGTTAAGGATTTGGTC
ATGAACAATAAAACTGTCTGCTTACATAAACAGTAATACAAGGGTGTTATGAGCCATATTCAACGGGAAACGTCTTGCT
CTAGGCCGCGATTAAATTCCAACATGGATGCTGATTTATATGGCTATAAATGGCTCGCGATAATGTCGGGCAATCAGGT
GCGACAATCTATCGATTGTATGGGAAGCCCGATGCGCCAGAGTTGTTTCTGAAACATGCAAAGTAGCGTTGCCAATGA
TGTTACAGATGAGATGGTCAGGACTAAACTGGCTGACGGAATTTATGCCTCTTCCGACCATCAAGCATTTTATCCGTACTC
CTGATGATGCATGGTTACTCACCACTGCAGTGTTCCTGCCGGATCCCCGGGAAAACAGCATTCCAGGTATTAGAAGAATATCCTGATTCAGGT
GAAAATATTGTTGATGCGCTGCCAGTTGCTCAGGCGCCAATCACGAATGAATAACGGTTTGGTTGATGCGAGTGATTTGTAATTGTCCTTTTAACAGCGA
TCGCGTATTTCGTCTCGCTGTTGAACAAGTCTGAAAGAAATGCATAAACTTTTGCCATTCTCACCGGATTCAGTCGTCACTCATGGT
ATGGCTGGCCCTGTTGATAACCTTATTTTGACGAGGGAAATAATGCCTCGGTAGTTTCTCCTTCATTACAGAAACGGCTTTTTCAAAAT
GATTTCTCACTTGATAACTCTGCCATCCTATGGAACTGCCTCGGTGAGTTTCATTGATGCTCGATGAGTTTTCTAAGAATTAATTCATGAG
CCGATACCAGGATCTTGCCATCCTGATATGAATAAATTGCAGTTTCATTCATTGATGCTCCGCCACATTCCCGCAAAAGTGCCACCTGAAA
ATGGTATTGATAATCCTGATATGAATAATTGCAGTTTCATTGATGCCCGCCACATTCCCGCAAAAGTGCCACCTGAAA
CGGATACATATTTGAATGTATTTAGAAAAATAAACAAATAGGGTTCCGCGACACATTCCCGCAAAAGTGCCACCTGAAA
TTGTAAACGTTAATATTTGTTAAATTTCGCGTTAAATTTTGTTAAATCAGCTCATTTTTAACCAATAGGCCGAAATC
GCCAAATCCCTTATAAATCAAAAGAATAGACCGAGATAGGGTTGAGTGTTGTTCCAGTTTGGAACAAGAGTCCACTATT
AAGAACGTGGACTCCAACGTCAAGGTGCCTAAAGCACTAAATCGGAACCTAAAGGGAGCCCCCGATTTAGAGCTTGACGGGGA
CAAGTTTTTGGGGTCGAGGTGCCGAGAAGGCGAAAGGCGAAAGGCGAAAGAAGCGAAAGGAGCGGGCGCTAGGGCGCTGGCAGCTGGCCAAGTGTAGCGGTCAC
AAGCCGGCGAACGTGGCGAGAAAGGAAGGGAAAGAAAGCGAAAGGAGCGGGCGCTAGGGCGCGCCATTGCCA
GCTGCCGCGTAACCACCACACCCGCCGCGCTTAATGCGCCGCTACAGGGCGCGTCCCATTCGCCA
```

Fig. 9A (continued)

(SEQ ID No.: 41)

MGIEEGKLVIWINGDKGYNGLAEVGKKFEKDTGIKVTVEHPDKLEEKFPQVAATGDGPDIIFWAHDRFGGYAQSGLLAEI
TPDKAFQDKLYPFTWDAVRYNGKLIAYPIAVEALSLIYNKDLLPNPKTWEEIPALDKELKAKGKSALMFNLQEPYFTWP
LIAADGGYAFKYENGKYDIKDVGVDNAGAKAGLTFLVDLIKNKHMNADTDYSIAEAAFNKGETAMTINGPWAWSNIDTSK
VNYGVTVLPTFKGQPSKPFVGVLSAGINAASPNKELAKEFLENYLLTDEGLEAVNKDKPLGAVALKSYEEELAKDPRIAA
TMENAQKGEIMPNIPQMSAFWYAVRTAVINAASGRQTVDEALKDAQTNSSGGSGSGMDEKTTGWRGGHVVEGLAGELEQ
LRARLEHHPGQREPGSGHHHHHHEF

Fig. 9B